US010385080B2

(12) United States Patent
McMurray et al.

(10) Patent No.: US 10,385,080 B2
(45) Date of Patent: Aug. 20, 2019

(54) STAT6 INHIBITORS

(71) Applicants: Board of Regents, The University of Texas System, Austin, TX (US); Baylor College of Medicine, Houston, TX (US)

(72) Inventors: John S. McMurray; Pijus Kumar Mandal, Sugar Land, TX (US); Pietro Morlacchi, Houston, TX (US); Morgan Knight, Houston, TX (US); David B. Corry, Houston, TX (US)

(73) Assignees: Board of Regents, The University of Texas System, Austin, TX (US); Baylor College of Medicine, Houston, TX (US)

( * ) Notice: Subject to any disclaimer, the term of this patent is extended or adjusted under 35 U.S.C. 154(b) by 0 days.

(21) Appl. No.: 15/678,127

(22) Filed: Aug. 16, 2017

(65) Prior Publication Data
US 2018/0222931 A1 Aug. 9, 2018

Related U.S. Application Data

(62) Division of application No. 14/889,802, filed as application No. PCT/US2014/037342 on May 8, 2014, now Pat. No. 9,765,099.

(60) Provisional application No. 61/821,181, filed on May 8, 2013.

(51) Int. Cl.
C07D 207/02 (2006.01)
C07F 9/6561 (2006.01)
C07F 9/572 (2006.01)
A61K 9/00 (2006.01)
A61K 45/06 (2006.01)
C07F 9/12 (2006.01)
C07F 9/553 (2006.01)
C07F 9/60 (2006.01)
C07F 9/62 (2006.01)
C07F 9/6533 (2006.01)
C07F 9/6558 (2006.01)
C07F 9/6509 (2006.01)
C07K 5/062 (2006.01)
C07K 5/078 (2006.01)

(52) U.S. Cl.
CPC .......... *C07F 9/6561* (2013.01); *A61K 9/0043* (2013.01); *A61K 9/0073* (2013.01); *A61K 45/06* (2013.01); *C07F 9/12* (2013.01); *C07F 9/5532* (2013.01); *C07F 9/5535* (2013.01); *C07F 9/572* (2013.01); *C07F 9/5728* (2013.01); *C07F 9/60* (2013.01); *C07F 9/62* (2013.01); *C07F 9/6533* (2013.01); *C07F 9/65583* (2013.01); *C07F 9/650952* (2013.01); *C07K 5/06034* (2013.01); *C07K 5/06139* (2013.01)

(58) Field of Classification Search
CPC .................................................. C07D 207/02
See application file for complete search history.

(56) References Cited

U.S. PATENT DOCUMENTS

| 6,426,331 | B1 | 7/2002 | McKinney et al. |
| 6,576,766 | B1 | 6/2003 | Weigele et al. |
| 2005/0272753 | A1 | 12/2005 | Nagashima et al. |
| 2007/0010428 | A1 | 1/2007 | McMurray et al. |
| 2008/0227784 | A1 | 9/2008 | Tokuyama et al. |
| 2011/0319362 | A1 | 12/2011 | Wang et al. |

FOREIGN PATENT DOCUMENTS

| JP | 2003-513290 | 4/2003 |
| JP | 2003-525862 | 9/2003 |
| JP | 2004-510732 | 4/2004 |
| JP | 2008-506674 | 3/2008 |
| JP | 2010-174027 | 8/2010 |
| WO | WO 1996/016079 | 5/1996 |
| WO | WO 1997-012903 | 4/1997 |
| WO | WO 1997-043307 | 11/1997 |
| WO | WO 1999-024442 | 5/1999 |
| WO | WO 2000-044774 | 8/2000 |
| WO | WO 2001-033243 | 5/2001 |
| WO | WO 2001/068655 | 9/2001 |
| WO | WO 2001/083517 | 11/2001 |
| WO | WO 2002-028378 | 4/2002 |
| WO | WO 2006-008437 | 1/2006 |
| WO | WO 2007-148711 | 12/2007 |
| WO | WO 2008-070833 | 6/2008 |
| WO | WO 2010-118241 | 10/2010 |
| WO | WO 2010/118309 | 10/2010 |
| WO | WO 2012-044999 | 4/2012 |

OTHER PUBLICATIONS

Auzenne et al., "A phosphopeptide mimetic prodrug targeting the SH2 domain of Stat3 inhibits tumor growth and angiogenesis," *Journal of Experimental Therapeutics & Oncology*, 10(2):155-162, 2012.

Blease, "Therapeutics targeting IL-13 for the treatment of pulmonary inflammation and airway remodeling," *Curr. Opin. Investig. Drugs*, 9:1180-1184, 2008.

CAPLUS Database Entry corresponding to PCT Publication No. WO 2001/068655.

Chiba et al., "A novel STAT6 inhibitor AS1517499 ameliorates antigen-induced bronchial hypercontractility in mice," *Am. J. Respir. Cell Mol. Biol.*, 41:516-524, 2009.

Darcan-Nicolaisen et al., "Small interfering RNA against transcription factor STAT6 inhibits allergic airway inflammation and hyperreactivity in mice," *J. Immunol.*, 182:7501-7508, 2009.

(Continued)

*Primary Examiner* — Bruck Kifle
(74) *Attorney, Agent, or Firm* — Parker Highlander PLLC

(57) ABSTRACT

The present disclosure provides compounds that are useful for inhibiting the STAT6 pathway. Also provided are related pharmaceutical compositions and methods of using the compounds. In some embodiments, the compounds may be used to treat a disease such as, e.g., an allergic lung disease, allergic rhinitis, chronic pulmonary obstructive disease, or a cancer.

22 Claims, 25 Drawing Sheets
Specification includes a Sequence Listing.

(56) References Cited

OTHER PUBLICATIONS

Dhanik et al., "Binding modes of peptidomimetics designed to inhibit STAT3," *PLOS ONE*, 7(12):e51603, 2012.

Extended European Search Report issued in European Application No. 14794359.1, dated Jan. 5, 2017.

Fletcher et al., "Molecular approaches towards the inhibition of the signal transducer and activator of transcription 3 (Stat3) protein," *Chem Med Chem*, 3(8):1159-1168, 2008.

Kasaian et al., "IL-13 as a therapeutic target for respiratory disease," *Biochem. Pharmacol.*, 76:147-155, 2008.

Kheradmand et al., "A protease-activated pathway underlying Th cell type 2 activation and allergic lung disease," *J. Immunol.*, 169:5904-5911, 2002.

Mandal et al., "Conformationally constrained peptidomimetic inhibitors of signal transducer and activator of transcription 3: evaluation and molecular modeling," *J. Med. Chem.*, 52(8):2429-2442, 2009.

Mandal et al., "Potent and Selective Phosphopeptide Mimetic Prodrugs Targeted to the Src Homology 2 (SH2) Domain of Signal Transducer and Activator of Transcription 3," *J. Med. Chem.*, 54:3549-5463, 2011.

Mandal et al., "Solid-phase synthesis of Stat3 inhibitors incorporating O-carbamoylserine and O-carbamoylthreonine as glutamine mimics," *Bioorganic & Medicinal Chemistry Letters*, 17(3):654-656, 2007.

Mandal et al., "Structure-activity studies of phosphopeptidomimetic prodrugs targeting the Src homology 2 (SH2) domain of signal transducer and activator of transcription 3 (Stat3)," *International Journal of Peptide Research and Therapeutics*, 19(1):3-12, 2013.

Mandal et al., "Structure-affinity relationships of glutamine mimics incorporated into phosphopeptides targeted to the SH2 domain of signal transducer and activator of transcription 3," *J. Med. Chem.*, 52(19):6126-6141, 2009.

Mandal et al., "Synthesis of phosphatase-stable, cell-permeable peptidomimetic prodrugs that target the SH2 domain of Stat3," *Org. Lett.*, 11:3394-3397, 2009.

McCusker et al., "Inhibition of Experimental Allergic Airways Disease by Local Application of a Cell-Penetrating Dominant-Negative STAT-6 Peptide," *J. Immunol.*, 179:2556-2564, 2007.

Nagashima et al., "Identification of 4-benzylamino-2-[(4-morpholin-4-ylphenyl)amino]pyrimidine-5-carboxamide derivatives as potent and orally bioavailable STAT6 inhibitors," *Bioorg. Med. Chem.*, 16:6509-6521, 2008.

Nagashima et al., "Novel 7H-pyrrolo[2,3-d]pyrimidine derivatives as potent and orally active STAT6 inhibitors," *Bioorg. Med. Chem.*, 17:6926-6936, 2009.

Nagashima et al., "Synthesis and evaluation of 2-{[2-(4-hydroxyphenyl)-ethyl]amino}pyrimidine-5-carboxamide derivatives as novel STAT6 inhibitors," *Bioorg. Med. Chem.*, 15:1044-1055, 2007.

Nguyen et al., "Beta2-adrenoceptor signaling is required for the development of an asthma phenotype in a murine model," *Proc Natl Acad Sci U S A*, 106:2435-2440, 2009.

Oh et al., "Investigational therapeutics targeting the IL-4/IL-13/STAT-6 pathway for the treatment of asthma," *Eur. Respir. Rev.*, 19:46-54, 2010.

Ohga et al., "YM-341619 suppresses the differentiation of spleen T cells into Th2 cells in vitro, eosinophilia, and airway hyperresponsiveness in rat allergic models," *Eur. J. Pharmacol.*, 590:409-416, 2008.

PCT International Preliminary Report on Patentability issued in International Application No. PCT/US2014/037342, dated Nov. 10, 2015.

PCT International Search Report and Written Opinion issued in International Application No. PCT/US2014/037342, dated Dec. 2, 2014.

Polikepahad et al., "A reversible, non-invasive method for airway resistance measurements and bronchoalveolar lavage fluid sampling in mice," *J. Vis. Exp.*, 38, 2010.

Popescu, "New asthma drugs acting on gene expression," *J. Cell. Mol. Med.*, 7:475-486, 2003.

PubChem, Compound Summary for CID 53248592, retrieved from https://pubchem.ncbi.nlm.nih.gov/summary/summary.cgi?cid=53248592, created Jul. 18, 2011, retrieved Aug. 26, 2014.

PubChem, Compound Summary for CID 9896629, retrieved from https://pubchem.ncbi.nlm.nih.gov/summary/summary.cgi?cid=9896629, created Oct. 25, 2006, retrieved Aug. 27, 2014.

Shaw et al. "IL-33-Responsive Innate Lymphoid Cells Are an Important Source of IL-13 in Chronic Rhinosinusitis with Nasal Polyps," *Am. J. Respir. & Crit. Care Med.*, 188:432-439, 2013.

Stolzenberger et al., "Specific inhibition of interleukin-4-dependent Stat6 activation by an intracellularly delivered peptide," *Eur. J. Biochem.*, 268:4809-4814, 2001.

Walford and Doherty, "STAT6 and lung inflammation," *JAK-STAT*, 2(4):e25301, pp. 1-11, 2013.

Walsh, "An update on emerging drugs for asthma," *Expert Opin. Emerg. Drugs*, 17:37-42, 2012.

Wang et al., "Effective treatment of experimental ragweed-induced asthma with STAT-6-IP, a topically delivered cell-penetrating peptide," *Clin. Exp. Allergy*, 41:1622-1630, 2011.

Wu et al., "A high-throughput STAT binding assay using fluorescence polarization," *Anal. Biochem.*, 249:29-36, 1997.

Coleman et al., "Investigation of the binding determinants of phosphopeptides targeted to the SRC homology 2 domain of the signal transducer and activator of transcription 3. Development of a high-affinity peptide inhibitor," *J. Med Chem.*, 48(21):6661-6670, 2005.

Office Action issued in Japanese Applications No. 2016-513077, and English language translation thereof, dated Mar. 12, 2018.

Shahripour et al., "Novel phosphotyrosine mimetics in the design of peptide ligands for pp60$^{src}$ SH2 domain," *Bioorganic & Medicinal Chemistry Letters*, 6(11):1209-1214, 1996.

Zhang et al., "Identification and characterization of small molecule inhibitors of signal transducer and activator of transcription 3 (STAT3) signaling pathway by virtual screening," *Bioorganic & Medicinal Chemistry Letters*, 23(7):2225-2229, 2013.

Pacofsky et al., "Potent dipeptide inhibitors of the pp60$^{c-src}$ SH2 domain," *J. Med. Chem.*, 41:1894-1908, 1998.

FROM STOLZENBERGER ET AL. (2001)

AP/Stat6BP  GASSGEEG*YKPFQDLC-CRQIKIWFQNRRMKWKK (SEQ ID NO: 1)

AP/Stat6CP  GASSGEEGYKPFQDLC-CRQIKIWFQNRRMKWKK (SEQ ID NO: 2)

GASSGEEGXKPFQDLC-CRQIKIWFQNRRMKWKK (SEQ ID NO: 3)

FROM MCCUSKER ET AL. (2007) AND WANG ET AL. (2011)

STAT-6-IP   YARAAARQARAGRG*YVSTT (SEQ ID NO: 4)

STAT-6-CP   YARAAARQARAGRGFVSTT (SEQ ID NO: 5)

*Y = PHOSPHOTYROSINE, X = PHOSPHONOMETHYLPHENYLALANINE

FIG. 3

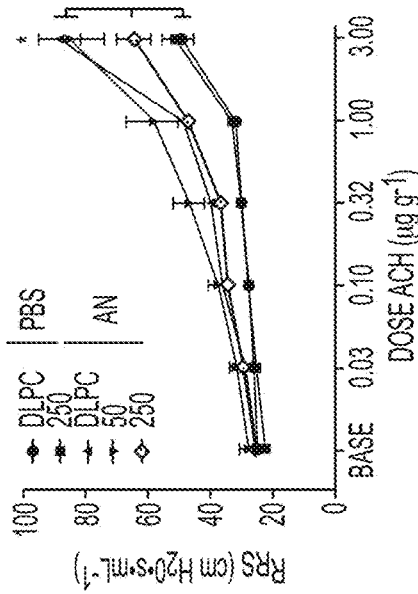
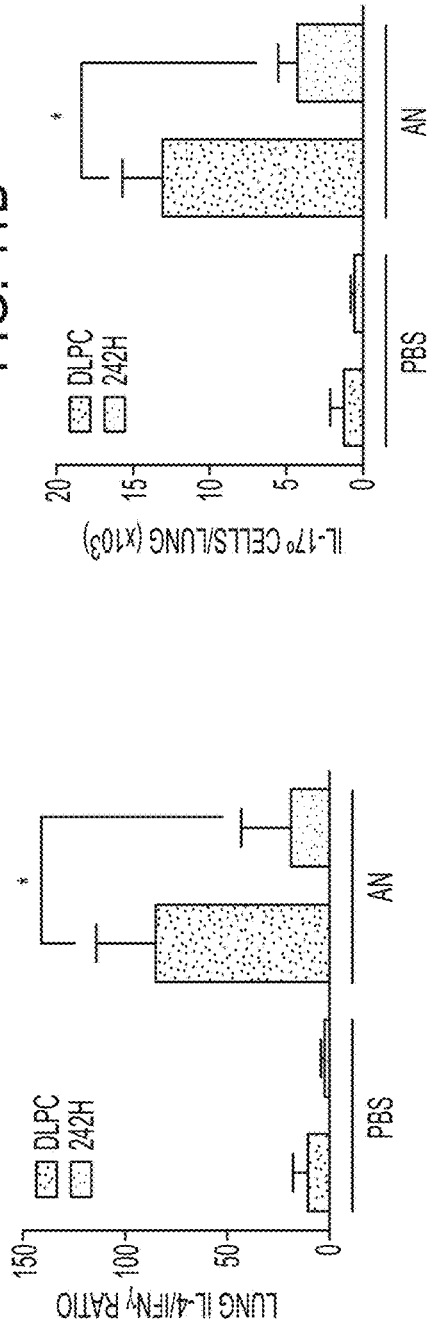
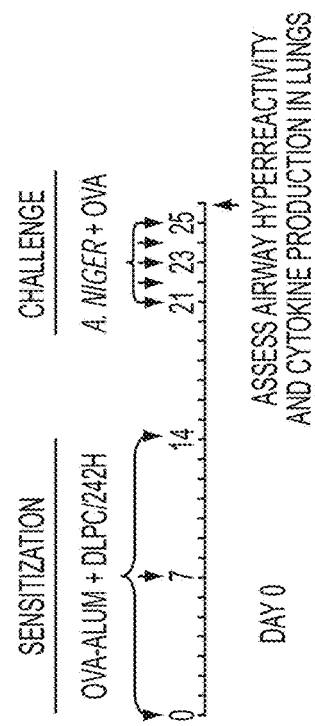
FIG. 11A
FIG. 11B
FIG. 11C
FIG. 11D

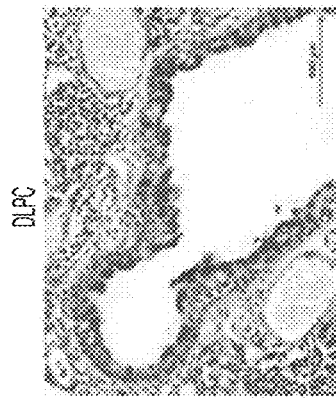
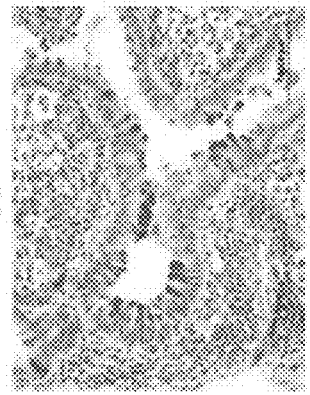
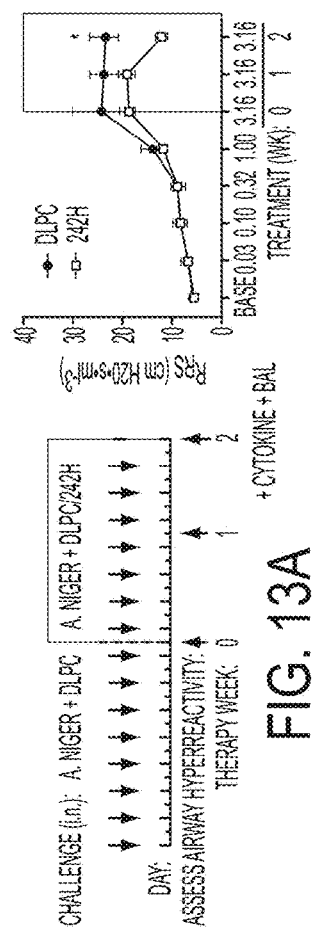
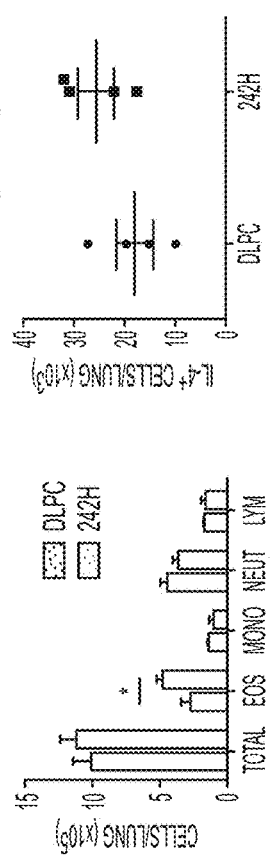
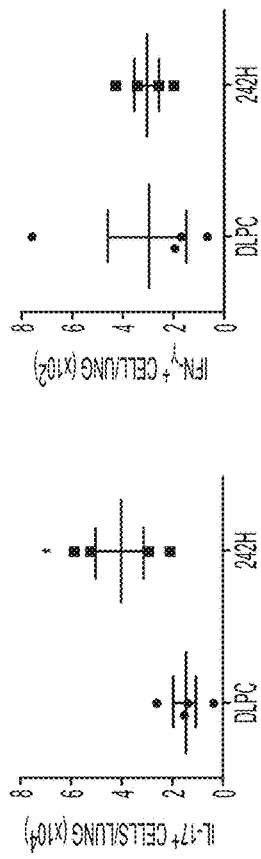

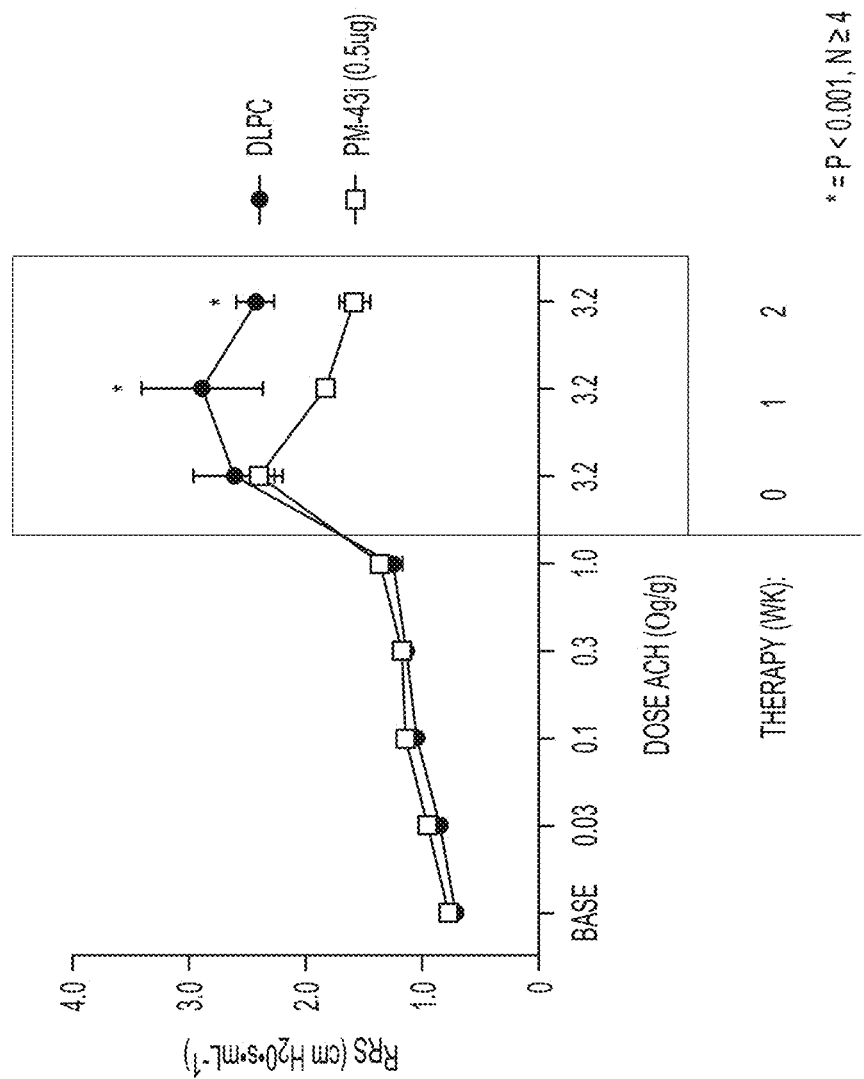

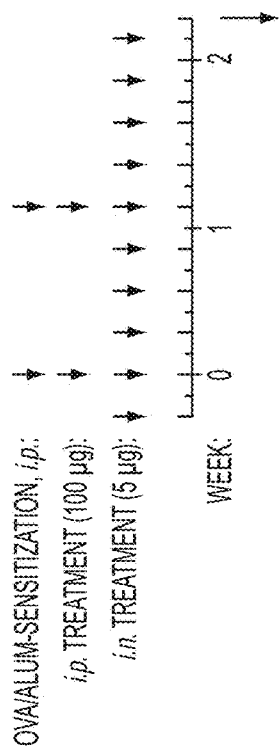
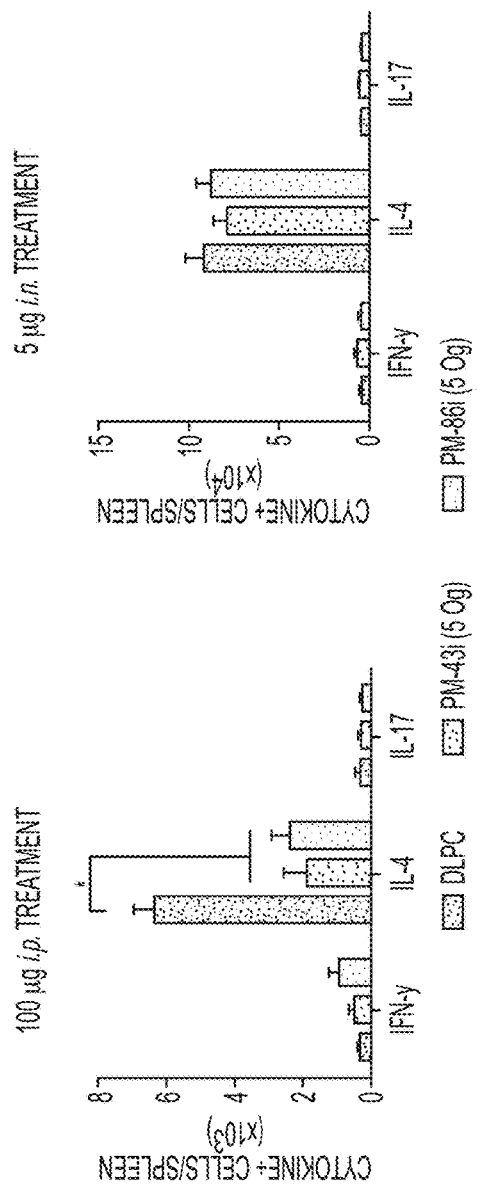

SEQUENCE LISTING

<160> NUMBER OF SEQ ID NOS: 5

<210> SEQ ID NO 1
<211> LENGTH: 33
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: X = phosphotyrosine

<400> SEQUENCE: 1

Gly Ala Ser Ser Gly Glu Glu Gly Xaa Lys Pro Phe Gln Asp Leu Cys
1               5                   10                  15

Cys Arg Gln Ile Lys Ile Trp Phe Gln Asn Arg Arg Met Lys Trp Lys
            20                  25                  30

Lys

<210> SEQ ID NO 2
<211> LENGTH: 33
<212> TYPE: PRT
<213> ORGANISM: Artificial sequence
<220> FEATURE:
<223> OTHER INFORMATION: Synthetic peptide

<400> SEQUENCE: 2

Gly Ala Ser Ser Gly Glu Glu Gly Tyr Lys Pro Phe Gln Asp Leu Cys
1               5                   10                  15

Cys Arg Gln Ile Lys Ile Trp Phe Gln Asn Arg Arg Met Lys Trp Lys
            20                  25                  30

Lys

<210> SEQ ID NO 3
<211> LENGTH: 33
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: X = phosphonomethylphenylalanine

<400> SEQUENCE: 3

Gly Ala Ser Ser Gly Glu Glu Gly Xaa Lys Pro Phe Gln Asp Leu Cys
1               5                   10                  15

Cys Arg Gln Ile Lys Ile Trp Phe Gln Asn Arg Arg Met Lys Trp Lys
            20                  25                  30

Lys

<210> SEQ ID NO 4
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (15)..(15)
<223> OTHER INFORMATION: X = phosphotyrosine

<400> SEQUENCE: 4

Tyr Ala Arg Ala Ala Ala Arg Gln Ala Arg Ala Gly Arg Gly Xaa Val

```
1               5              10              15
Ser Thr Thr

<210> SEQ ID NO 5
<211> LENGTH: 19
<212> TYPE: PRT
<213> ORGANISM: Artificial sequence
<220> FEATURE:
<223> OTHER INFORMATION: Synthetic peptide

<400> SEQUENCE: 5

Tyr Ala Arg Ala Ala Ala Arg Gln Ala Arg Ala Gly Arg Gly Phe Val
1               5                   10                  15
Ser Thr Thr
```

STAT6 INHIBITORS

This application is a divisional of U.S. application Ser. No. 14/889,802, filed Nov. 6, 2015, which is national phase application under 35 U.S.C. § 371 of International Application No. PCT/US2014/037342, filed May 8, 2014, which claims the benefit of U.S. Provisional Patent Application No. 61/821,181, filed May 8, 2013, the entirety of each of which is incorporated herein by reference.

BACKGROUND OF THE INVENTION

1. Field of the Invention

The present invention relates generally to the field of medicinal chemistry and medicine. More particularly, it concerns STAT6 inhibitors.

2. Description of Related Art

Asthma patients have elevated levels of the cytokines interleukin 4 (IL-4) and IL-13 in their airways, which result in mucus production, airway hyperresponsiveness (AHR), eosinophil recruitment, T-Helper cell 2 (Th2) activation, resulting in immunoglobulin class switching to IgE, and inflammation (reviews 1-3). These two cytokines signal through a common receptor, the alpha chain of the IL-4 receptor (IL-4Rα). On cytokine binding, tyrosine residues on the receptor are phosphorylated by JAK1, JAK3, or Tyk2. Signal transducer and activator of transcription 6 (STAT6), via its Src homology 2 (SH2) domain, is recruited to the phosphotyrosine residues and is then phosphorylated on Tyr641. STAT6 then dimerizes via reciprocal SH2 domain-pTyr641 interactions, translocates to the nucleus, and participates in the expression of genes leading to asthma and airway hyperresponsiveness (AHR). Elevated STAT6 levels have been found in the bronchial epithelium of asthma patients (Mullings et al. 2001). Stat6 knockout mice do not develop airway hyperresponsiveness (AHR) or lung pathology associated with asthma regardless of the asthmatic stimuli applied (Darcan-Nicolaisen et al. 2009). Taken together, these results support the hypothesis that inhibiting the activity of STAT6 is a beneficial modality for asthma treatment (Kasaian, M. T. et al. 2008; Popescu, F. D. 2003; Chiba, Y. et al. 2009; McCusker, C. T. et al. 2007; Nagashima, S. et al. 2009; Nagashima, S. et al. 2008; Nagashima, S. et al. 2007; Ohga, K. et al. 2008; Stolzenberger, S. et al. 2001; Oh, C. K. et al. 2010).

STAT6 activity has been inhibited by small molecules (Nagashima, S. et al. 2009; Nagashima, S. et al. 2008; Nagashima, S. et al. 2007; Ohga, K. et al. 2008; Chiba, Y. et al. 2009), siRNA (Darcan-Nicolaisen, Y. et al. 2009), decoy oligonucleotides,[15] and antibodies (Walsh, G. M. 2012; Blease, K. 2008). Nagashima et al. identified a small molecule hit by screening a company library for the ability to inhibit a STAT6 reporter gene (Nagashima, S. et al. 2007), an assay that drove lead optimization leading to AS 1571499 (FIG. 2). Further development led to AS 1617612, also known as YM 341619 (Nagashima, S. et al. 2008), and then to AS 1810722 (Nagashima et al. 2009). Zhou et al. screened libraries and identified (R)-76 and its synthetic derivative (R)-84 that bind to STAT6 and prevent phosphorylation on Tyr641 (FIG. 2). To date, none of these materials have proved to be effective at treating STAT6-mediated diseases.

A number of potential phosphopeptide compounds have been prepared but few have the potential to advance to a clinical drug candidate. Stolzenberger et al.; Stolzenberger, S. et al. 2001, prepared a phosphopeptide derived from Tyr631 of IL-4Rα, a docking site for STAT6, coupled to the antennapedia cell penetration sequence (AP/STAT6BP) (FIG. 3). IL-4 stimulation of STAT6 phosphorylation in RAMOS cells was inhibited at 5 and 10 M, but recovered at 30 min. McCusker, et. al. (2007), reported that STAT-6-IP, a phosphopeptide derived from the phosphorylation site of STAT6, Tyr641, attached to a cell penetration sequence from TAT PT4 protein transduction domain (STAT-6-IP), inhibited in vitro IL-4 and IL-13 expression from splenocytes from mice challenged with ovalbumin (OVA) (FIG. 3). Importantly, in vivo intranasal administration inhibited OVA-induced lung inflammation and mucus production, eosinophil migration and AHR. The same group recently reported that intranasal administration of STAT-6-IP inhibited the same symptoms in a mouse asthma model induced by ragweed pollen (Wang, Y. et al. 2011). However, these materials are not likely to become commercial products for the treatment of asthma.

A few potential small molecular peptide mimetics have been explored that showed promise as potential STAT6 inhibitors. Small molecule peptide mimetics that target the SH2 domain of STAT6 have been reported in U.S. Pat. No. 6,426,331 and PCT Patent Application WO2001/083517. Although extensive structure-affinity relationship studies were reported, the synthesis of only one compound which was effective to inhibit STAT6 phosphorylation in intact cells was described (PM-241H, our nomenclature, FIG. 4). However, the synthesis of the compound was complicated and resulted in poor yields. Furthermore, that compound was not tested for any biological activity relating to STAT6. Clearly, there is a need for new STAT6 inhibitors.

SUMMARY OF THE INVENTION

The present invention overcomes limitations in the prior art by providing in some aspects compounds that can inhibit STAT6 and/or STAT5. In some embodiments, one or more of the compounds may be included in a pharmaceutical composition and used to treat a disease such as, e.g., asthma, airway hyperresponsiveness (AHR), an allergic disease, an allergic lung disease, allergic rhinitis, or chronic rhinosinusitis. In some embodiments, a STAT6 inhibitor of the present invention may be used to selectively inhibit STAT6 in a mammalian subject, such as a human, to treat an allergic lung disease. In some embodiments, a compound of the present invention may be used to treat a cancer.

An aspect of the present invention relates to a compound of the formula:

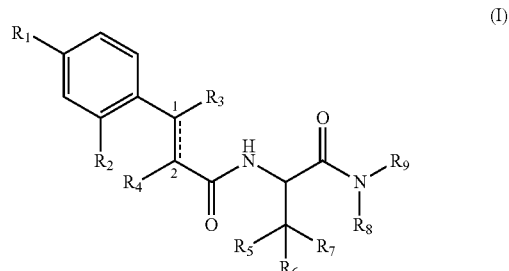

wherein: the bond between carbons 1 and 2 is a single or double bond; $R_1$ is phosphate, $-OP(O)(OR_{10})(OR_{10'})$, -alkyl$_{(C \le 6)}$-P(O)(OR$_{10}$)(OR$_{10'}$), or a substituted version of any of these groups; wherein $R_{10}$ and $R_{10'}$ are each independently hydrogen, alkyl$_{(C\leq 6)}$, aryl$_{(C\leq 8)}$, aralkyl$_{(C\leq 12)}$, -alkyl$_{(C\leq 6)}$-O—C(O)-alkyl$_{(C\leq 6)}$, -alkyl$_{(C\leq 6)}$-O—C(O)-aryl$_{(C\leq 8)}$, or

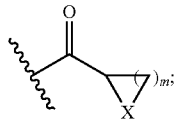

wherein m=0-8; wherein X is —CH$_2$—, —O—, —S—, or —NH—; provided that R$_{10}$ and R$_{10'}$ are not both hydrogen; R$_2$ is hydrogen or R$_2$ is taken together with R$_{11}$ as provided below; R$_3$, R$_5$, R$_6$, and R$_7$ are each independently hydrogen, unsubstituted alkyl$_{(C\leq 6)}$, or substituted alkyl$_{(C\leq 6)}$, or (R$_7$ and R$_8$) are taken together as provided below, or (R$_7$, R$_8$, and R$_9$) are taken together as provided below; R$_4$ is hydrogen or —N(R$_{11}$)R$_{12}$; wherein: R$_{11}$ is hydrogen, alkyl$_{(C\leq 6)}$, aryl$_{(C\leq 8)}$, acyl$_{(C\leq 6)}$, or a substituted version of any of these groups, or R$_{11}$ is taken together with R$_2$ as provided, below; R$_{12}$ is hydrogen, alkyl$_{(C\leq 6)}$, acyl$_{(C\leq 6)}$, or R$_{12}$ is taken together with R$_{11}$ as provided below; R$_8$ is hydrogen, unsubstituted alkyl$_{(C\leq 6)}$, substituted alkyl$_{(C\leq 6)}$, unsubstituted aryl$_{(C\leq 8)}$, substituted aryl$_{(C\leq 8)}$, an amino acid, -alkanediyl$_{(C\leq 6)}$-C(O)NX$_1$X$_2$, —CH$_2$—C(O)NX$_1$X$_2$, wherein X$_1$ and X$_2$ are each independently alkyl$_{(C\leq 6)}$, aryl$_{(C\leq 12)}$, or a substituted version of either of these groups,

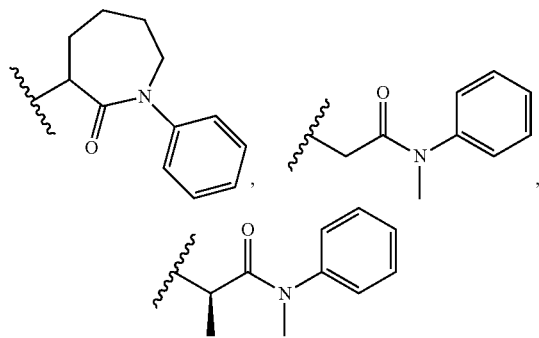

Nor R$_8$ is taken together with R$_7$ as provided below, or R$_8$ is taken together with R$_7$ and R$_9$ as provided below, or R$_8$ is taken together with R$_9$ as provided below; R$_9$ is hydrogen, unsubstituted alkyl$_{(C\leq 6)}$, substituted alkyl$_{(C\leq 6)}$, unsubstituted aryl$_{(C\leq 8)}$, substituted aryl$_{(C\leq 8)}$, an amino acid, -alkanediyl$_{(C\leq 6)}$-C(O)NX$_1$X$_2$, —CH$_2$—C(O)NX$_1$X$_2$, wherein X$_1$ and X$_2$ are each independently alkyl$_{(C\leq 6)}$, aryl$_{(C\leq 12)}$, or a substituted version of either of these groups,

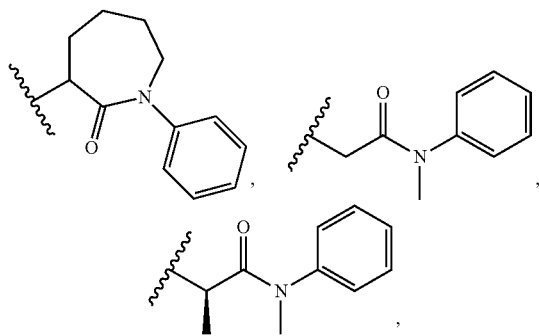

or R$_9$ is taken together with R$_7$ and R$_8$ as provided below, or R$_9$ is taken together with R$_8$ as provided below; provided that when R$_4$ is —N(R$_{11}$)R$_{12}$ and (R$_2$ and R$_{11}$) are taken together, the compound is further defined by formula IA:

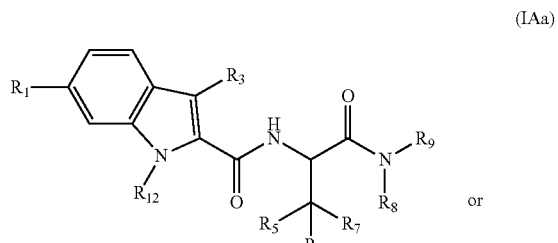

(IAa)

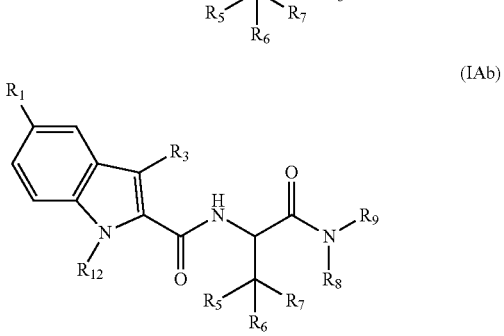

(IAb)

provided that when R$_4$ is —N(R$_{11}$)R$_{12}$ and (R$_{11}$ and R$_{12}$) are taken together, the compound is further defined by formula IB:

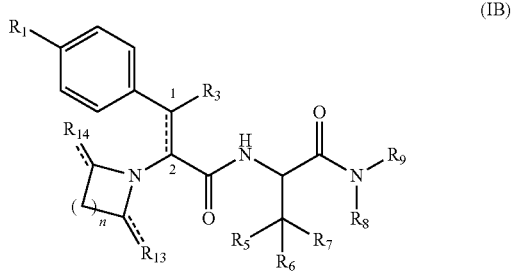

(IB)

wherein: R$_{13}$ and R$_{14}$ are each independently hydrogen or oxo; and n is 1, 2, 3, 4, or 5; provided that when R$_7$ and R$_8$ are taken together, the compound is further defined by formula IC:

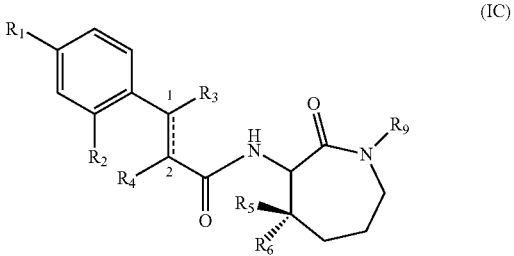

(IC)

provided that when R$_7$, R$_8$, and R$_9$ are taken together, the compound is further defined by formula ID or formula IE:

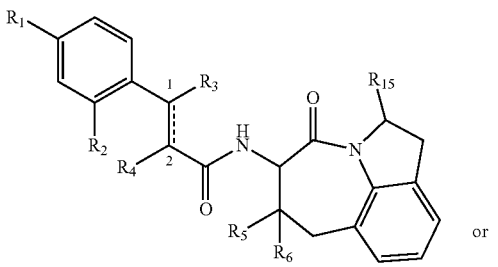

(ID)

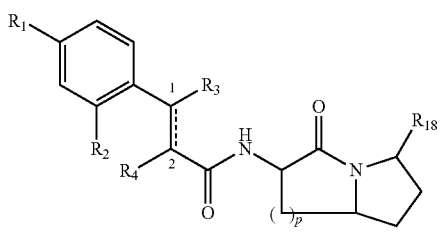

(IE)

wherein: $R_{15}$ is hydrogen or —C(O)NR$_{16}$R$_{17}$; wherein: $R_{16}$ and $R_{17}$ are each independently hydrogen, alkyl$_{(C \leq 6)}$, aryl$_{(C \leq 8)}$, or a substituted version of any of these groups; $R_{18}$ is hydrogen, -alkenediyl$_{(C \leq 6)}$-aryl$_{(C \leq 8)}$, aralkyl$_{(C \leq 12)}$, —C(O)-alkyl$_{(C \leq 6)}$, —C(O)-heterocycloalkyl$_{(C \leq 12)}$, —C(O)-heteroaryl$_{(C \leq 12)}$,

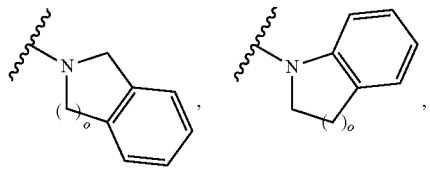

or —C(O)NR$_{19}$R$_{20}$; wherein: $R_{19}$ and $R_{20}$ are each independently hydrogen, alkyl$_{(C \leq 6)}$, aryl$_{(C \leq 8)}$, or a substituted version of either of these groups; o is 1, 2, or 3; and p is 1, 2, 3, 4, or 5;

provided that when $R_8$ and $R_9$ are taken together, the compound is further defined by formula IF:

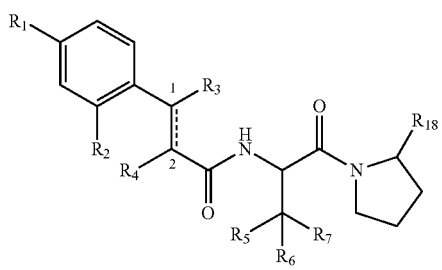

(IF)

wherein if $R_{18}$ is —C(O)NR$_{19}$R$_{20}$ and $R_{19}$ is aryl$_{(C \leq 8)}$, then $R_3$ is not hydrogen; or a pharmaceutically acceptable salt thereof.

The compound may have the formula I. The compound may have the formula IA. The compound may have the formula IB. The compound may have the formula IC. The compound may have the formula ID. The compound may have the formula IE. The compound may have the formula IF. In some embodiments, $R_{18}$ is —C(O)NR$_{19}$R$_{20}$, $R_{19}$ is aryl$_{(C \leq 8)}$, and $R_3$ is —CH$_3$. In some embodiments, the bond between carbons 1 and 2 is a double bond. In some embodiments, $R_1$ is phosphate. In some embodiments, $R_1$ is —CF$_2$—P(O)(OR$_{10}$)(OR$_{10'}$). In some embodiments, $R_{10}$ or $R_{10'}$ is —CH$_2$OC(O)C(CH$_3$)$_3$. In some embodiments, $R_{10}$ and $R_{10'}$ is —CH$_2$OC(O)C(CH$_3$)$_3$. In some embodiments, m=1-8; wherein X is —CH$_2$—, —O—, —S—, or —NH—. In some embodiments, if m equals then X is —CH$_3$, —OH, —SH, or —NH$_2$. In some embodiments, $R_2$ is hydrogen. In some embodiments, $R_3$ is hydrogen. In some embodiments, $R_3$ is alkyl$_{(C \leq 6)}$. In some embodiments, $R_3$ is methyl. In some embodiments, $R_4$ is hydrogen. In some embodiments, $R_4$ is —N(R$_{11}$)R$_{12}$. In some embodiments, $R_{11}$ is hydrogen. In some embodiments, $R_{12}$ is hydrogen. $R_{12}$ may be alkyl$_{(C \leq 6)}$. $R_{12}$ may be aryl$_{(C \leq 6)}$. $R_{12}$ may be acyl$_{(C \leq 6)}$. $R_{13}$ may be hydrogen. $R_{13}$ may be oxo. $R_{14}$ may be hydrogen. $R_{14}$ may be oxo. In some embodiments, n is 1. In some embodiments, n is 2. In some embodiments, n is 3. In some embodiments, $R_5$ is hydrogen. In some embodiments, $R_5$ is an alkyl$_{(C \leq 6)}$. In some embodiments, $R_5$ is methyl. $R_6$ may be hydrogen. $R_6$ may be an alkyl$_{(C \leq 6)}$. $R_6$ may be methyl. $R_7$ may be an alkyl$_{(C \leq 6)}$. $R_7$ may be methyl. In some embodiments, $R_5$, $R_6$, and $R_7$ are hydrogen or methyl. In some embodiments, $R_5$, $R_6$, and $R_7$ are hydrogen. In some embodiments, $R_5$, $R_6$, and $R_7$ are methyl. In some embodiments, $R_8$ is hydrogen. In some embodiments, $R_8$ is trans to the carbonyl. In some embodiments, $R_9$ is alkyl$_{(C \leq 6)}$. $R_9$ may be heterocycloalkyl$_{(C \leq 12)}$. $R_9$ may be an amino acid. $R_9$ may be

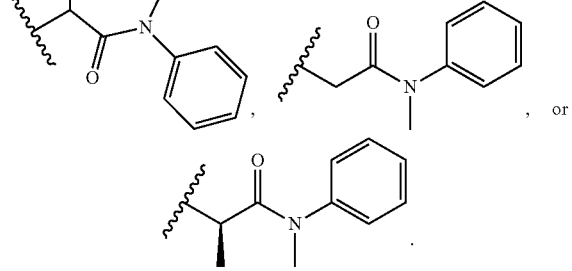

, or

In some embodiments, $R_9$ is

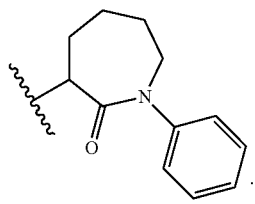 [SMILES: *C1CCCCN(c2ccccc2)C1=O]

In some embodiments, $R_9$ is

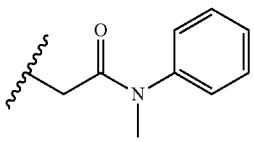

In some embodiments, $R_8$ or $R_9$ are -alkanediyl$_{(C≤6)}$-C(O)NX$_1$X$_2$ or —CH$_2$—C(O)NX$_1$X$_2$, wherein X$_1$ and X$_2$ are each independently alkyl$_{(C≤6)}$, aryl$_{(C≤12)}$, or a substituted version of either of these groups and the alkanediyl$_{(C≤6)}$ is unsubstituted or substituted. In some embodiments, the alkanediyl$_{(C≤6)}$ is —CH$_2$—, —CH$_2$CH$_2$—, or —CH$_2$CH$_2$CH$_2$—. The alkanediyl$_{(C≤6)}$ may be —CH$_2$—. In some embodiments, X$_1$ is aryl$_{(C≤12)}$ or substituted aryl$_{(C≤12)}$. In some embodiments, X$_1$ is aryl$_{(C≤10)}$ or substituted aryl$_{(C≤10)}$. In some embodiments, X$_1$ is aryl$_{(C≤8)}$ or substituted aryl$_{(C≤8)}$. In some embodiments, X$_1$ is aryl$_{(C6)}$ or substituted aryl$_{(C6)}$. X$_1$ may be phenyl. In some embodiments, X$_2$ is alkyl$_{(C≤6)}$ or substituted alkyl$_{(C≤6)}$. X$_2$ may be methyl. In some embodiments, R$_9$ is

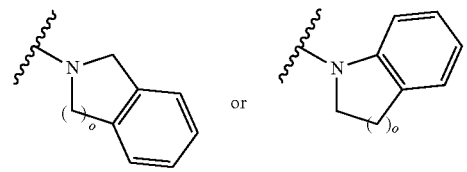

R$_9$ may be cis to the carbonyl. R$_{15}$ may be —C(O)NR$_{16}$R$_{17}$. R$_{16}$ may be trans to the carbonyl. R$_{16}$ may be alkyl$_{(C≤6)}$. R$_{16}$ may be methyl. R$_{17}$ may be cis to the carbonyl. R$_{17}$ may be aryl$_{(C≤8)}$. R$_{17}$ may be phenyl. R$_{18}$ may be alkenediyl$_{(C≤6)}$-aryl$_{(C≤8)}$. R$_{18}$ may be —C(H)C(H)CH$_2$CH$_2$C$_6$H$_5$ or —C(H)C(CH$_3$)C$_6$H$_5$. R$_{18}$ may be aralkyl$_{(C≤12)}$. R$_{18}$ may be —(CH$_2$)$_4$—C$_6$H$_5$. R$_{18}$ may be —C(O)-heterocycloalkyl$_{(C≤12)}$. The heterocycloalkyl may be selected from piperidine, N-methylpiperazine, and morpholine. The heterocycloalkyl may be selected from pyrrolidine, piperidine, and azepane. R$_{18}$ may be

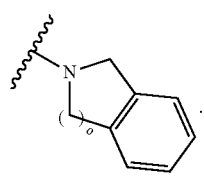

In some embodiments, R$_{18}$ is

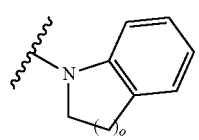

In some embodiments, R$_{18}$ is

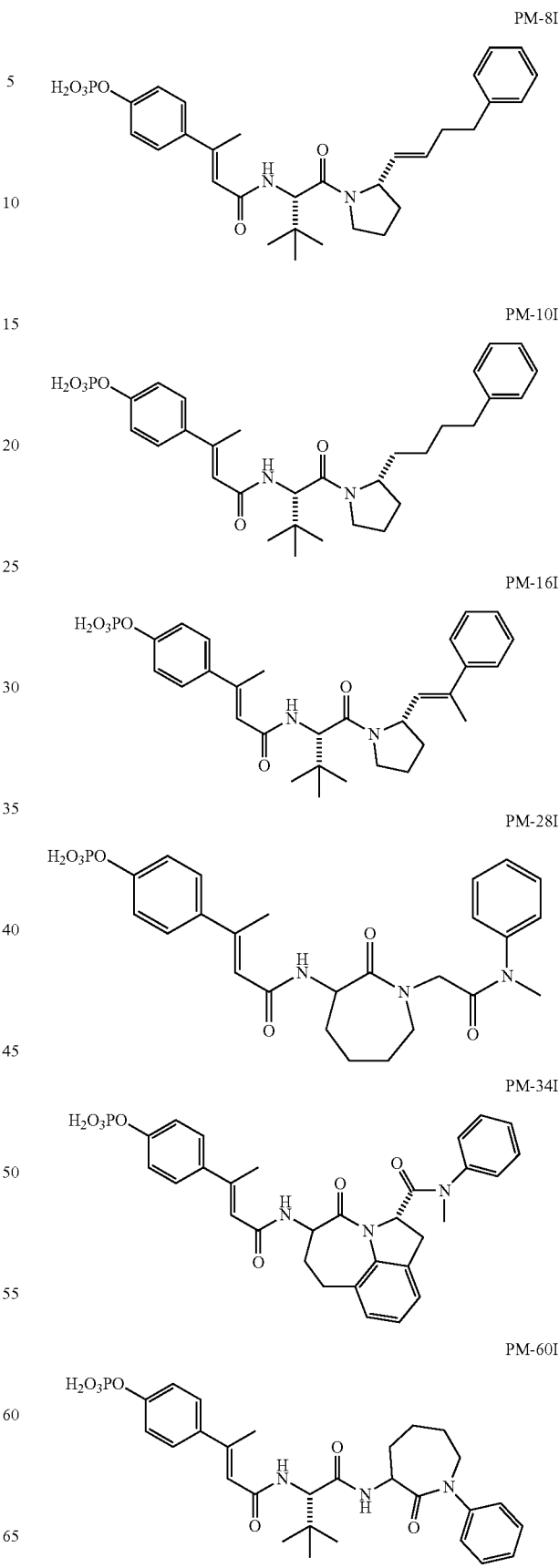

"o" may be 1, 2, or 3. R$_{18}$ may be —C(O)NR$_{19}$R$_{20}$. R$_{19}$ may be trans to the carbonyl. R$_{20}$ may be cis to the carbonyl.

In some embodiments, the compound is further defined as:

-continued
PM67I-A
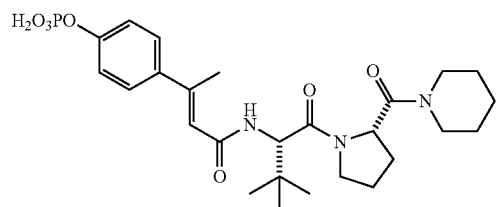
PM-67I-B
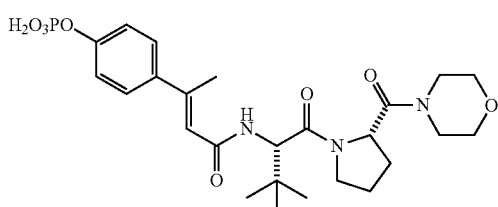
PM-67I-C
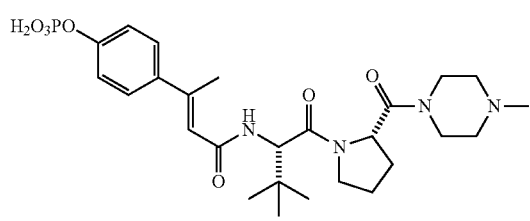
PM-59I
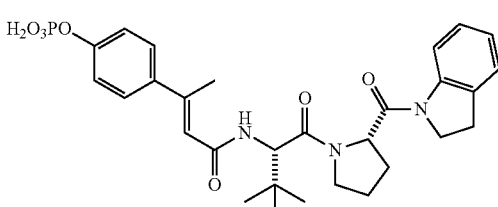
PM-87I
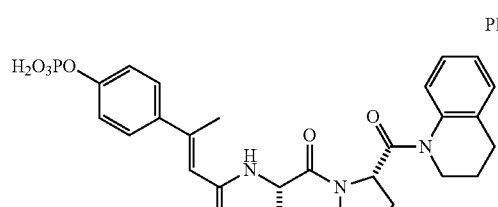
PM-71I_B
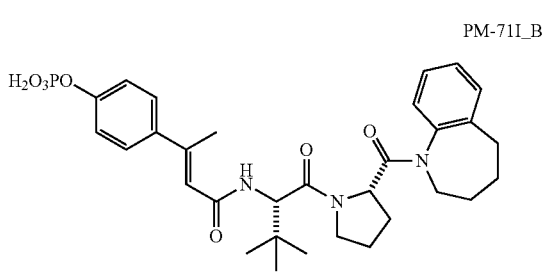
-continued
PM-71I-A
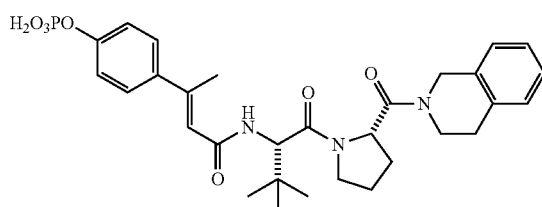
PM-12I
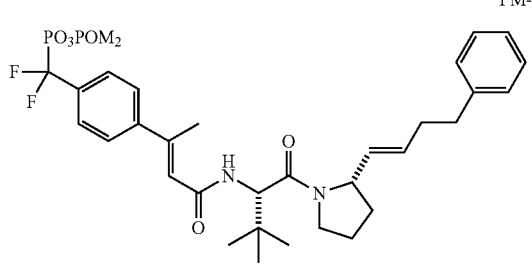
PM-16I
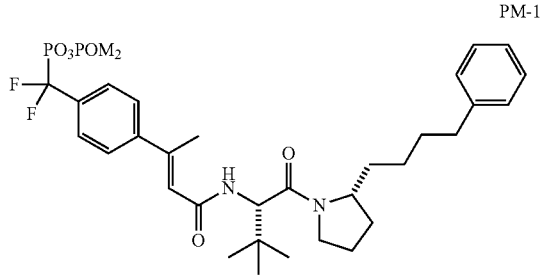
PM-43I
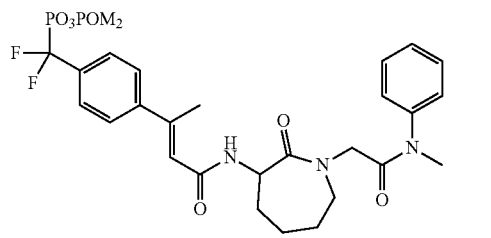
PM-42I
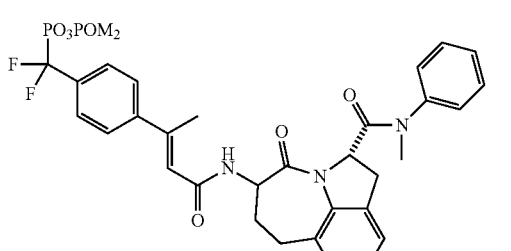
PM-64I
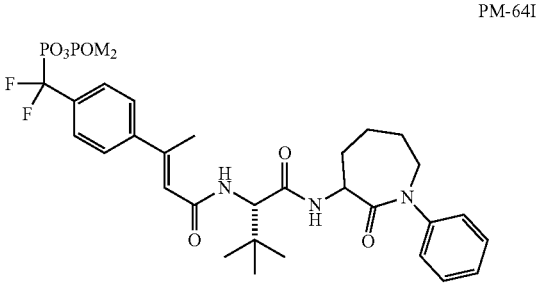

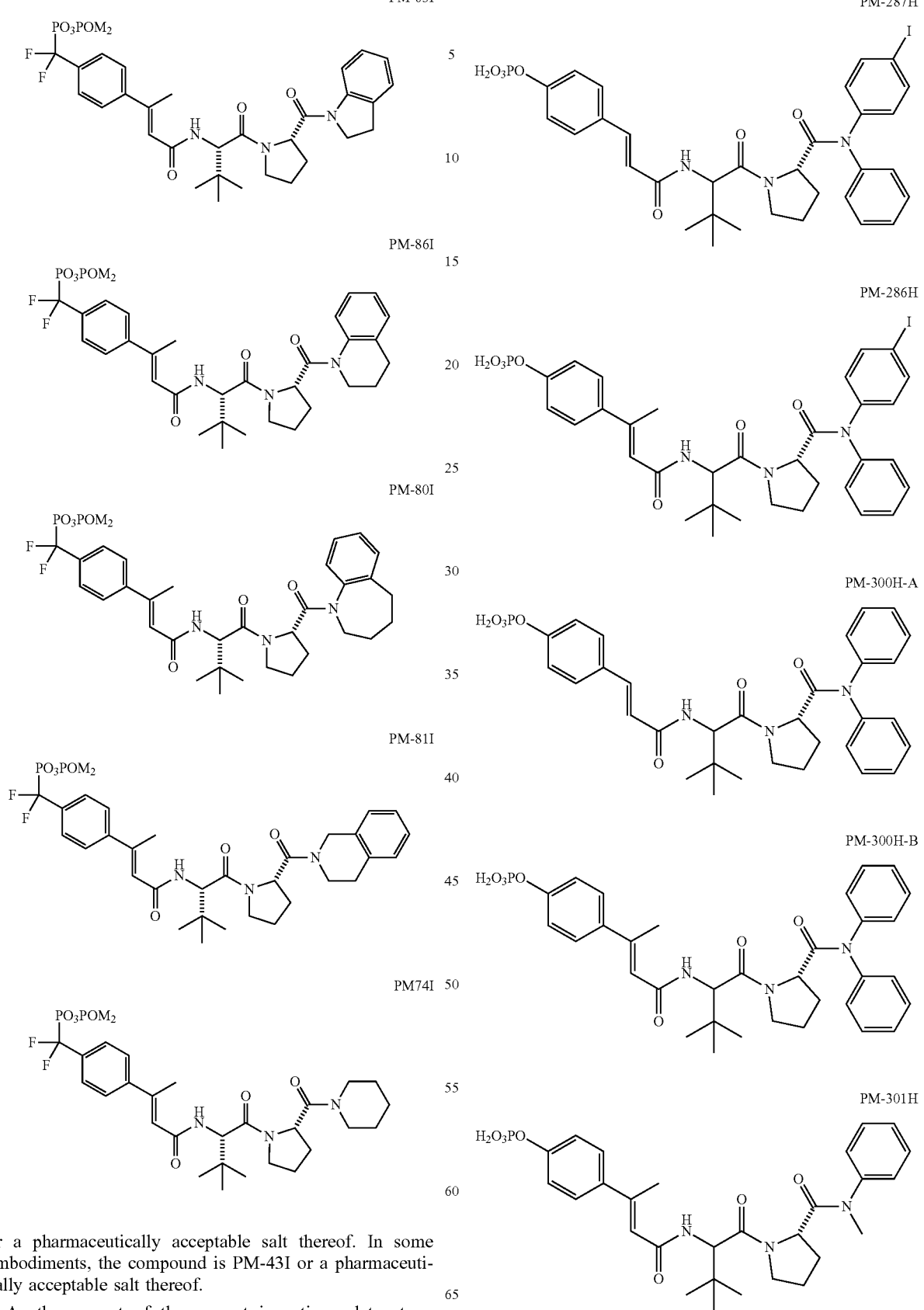
or a pharmaceutically acceptable salt thereof. In some embodiments, the compound is PM-43I or a pharmaceutically acceptable salt thereof.
Another aspect of the present invention relates to a compound of the formula:

-continued

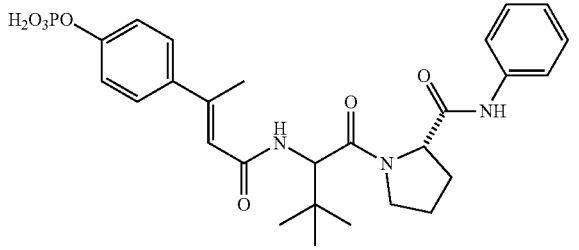

PM-302H-A

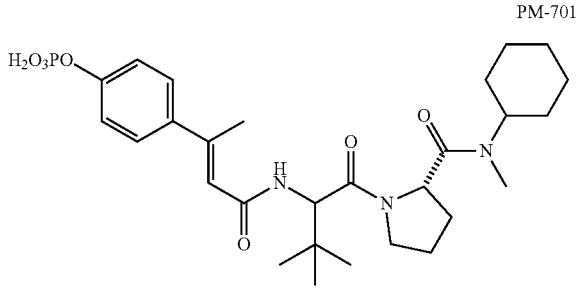

PM-701

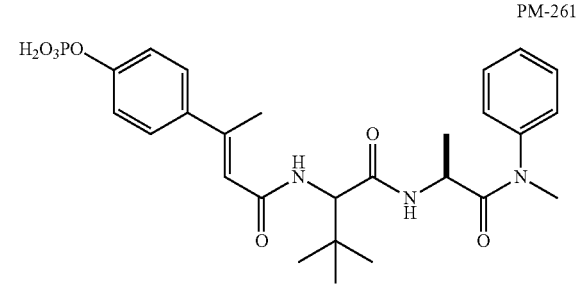

PM-261

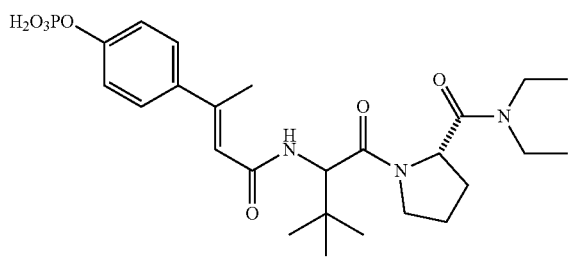

PM-302M-B or a pharmaceutically acceptable salt thereof. In some embodiments, the compound is not PM-287H or PM-300H-A. In some embodiments, a generic formula describing compounds of the present invention may exclude PM-241H. In other embodiments, the compound is PM-287H or PM-300H-A.

Another aspect of the present invention relates to a compound of the formula:

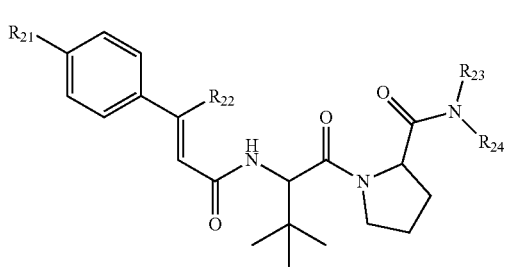

(II)

wherein: $R_{21}$ is phosphate, —OP(O)(OR$_{10}$)(OR$_{10'}$), -alkyl$_{(C \leq 6)}$-P(O)(OR$_{10}$)(OR$_{10'}$), or a substituted version of any of these groups; wherein $R_{10}$ and $R_{10'}$ are each independently hydrogen, alkyl$_{(C \leq 6)}$, aryl$_{(C \leq 8)}$, aralkyl$_{(C \leq 12)}$, alkyl$_{(C \leq 6)}$-O—C(O)-alkyl$_{(C \leq 6)}$, alkyl$_{(C \leq 6)}$-O—C(O)-aryl$_{(C \leq 8)}$, or

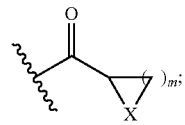

wherein m=0-8; wherein X is —CH$_2$—, —O—, —S—, or —NH—; provided that $R_{10}$ and $R_{10'}$ are not both hydrogen; $R_{22}$ is hydrogen or alkyl$_{(C \leq 6)}$; $R_2$ is hydrogen, alkyl$_{(C \leq 12)}$, substituted alkyl$_{(C \leq 12)}$, aryl$_{(C \leq 12)}$, or substituted aryl$_{(C \leq 12)}$; $R_{24}$ is aryl$_{(C \leq 12)}$ or substituted aryl$_{(C \leq 12)}$; provided that when $R_{22}$ is hydrogen then $R_{23}$ and $R_{24}$ are not both phenyl or iodophenyl; or a pharmaceutically acceptable salt thereof. $R_{21}$ may be -alkyl$_{(C \leq 6)}$-P(O)(OR$_{10}$)(OR$_{10'}$) or substituted -alkyl$_{(C \leq 6)}$-P(O)(OR$_{10}$)(OR$_{10'}$). In some embodiments, $R_{21}$ is —CF$_2$—P(O)(OCH$_2$OC(O)C(CH$_3$)$_3$)$_2$. $R_{22}$ may be hydrogen. $R_{23}$ may be aryl$_{(C \leq 12)}$. $R_{23}$ may be phenyl. $R_{24}$ may be aryl$_{(C8-C12)}$. $R_{24}$ may be biphenyl. In some embodiments, compound has the formula:

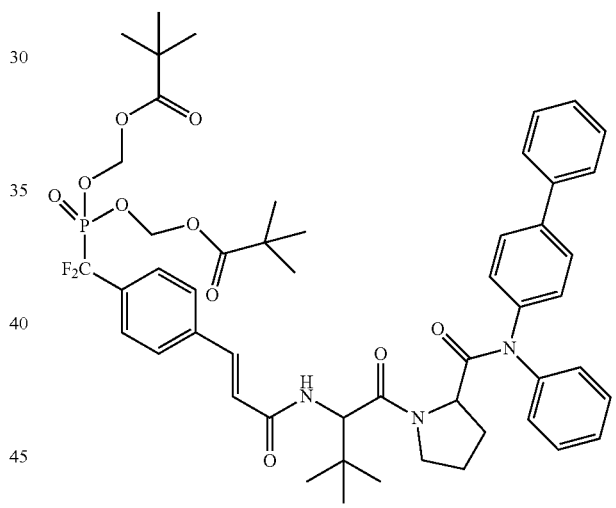

or a pharmaceutically acceptable salt thereof.

Yet another aspect of the present invention relates to a pharmaceutical composition comprising a compound of the present invention and an excipient. The pharmaceutical composition may be formulated for oral, intravenous, intranasal, or inhalational administration. In some embodiments, the pharmaceutical composition is comprised in a nebulizer, an inhaler, or a nasal spray. The pharmaceutical composition may further comprise a bronchodialator. In some embodiments, the bronchodialator is a long-acting β2 agonist (e.g., salmeterol, carvedilol, formoterol).

Another aspect of the present invention relates to a method of treating an allergic or inflammatory disease in a subject comprising administering to the subject a therapeutically effective amount of a compound of the present invention to the subject. The disease may be a lung disease such as, e.g., asthma, airway hyperresponsiveness (AHR), an allergic disease, allergic rhinitis, emphysema, chronic obstructive pulmonary disease (COPD), reactive airway disease, chronic rhinosinusitis, or essentially any other disease of the upper or lower airways that produces airflow obstruction. The method may further comprise inhibition of a second STAT protein. The other STAT protein may be STAT5 or STAT3. The method may further comprise administering to the subject a second therapeutic compound. The second therapeutic may be administered simultaneously or concurrently with the compound or sequentially to the compound. The second therapeutic may be in the same pharmaceutical preparation as the compound or a different pharmaceutical from the compound. The second therapeutic compound may be a bronchodialator (e.g., short-acting β-2 agonist, a long-acting β2 agonist, or an anticholinergic), an anti-inflammatory steroid, an antihistamine, or an anti-fungal antibiotic or any combination of these agents. The anti-inflammatory steroid may be a corticosteroid such as, e.g., fluticasone, beclomethasone, etc. In some embodiments, the second therapeutic compound is a non-inhaled therapeutic agent such as, e.g., a leukotriene receptor modifier (e.g., montelukast), and anti-IgE antibody (e.g., omalizumab), magnesium, theophylline, an allergen immunotherapy, or an oral or intravenous corticosteroid (e.g., prednisone, methylpredisolone). It is anticipated that, in some embodiments, a second therapeutic may not be needed to treat the disease, and in some embodiments a STAT6 inhibitor of the present invention may be administered to a subject as a monotherapy.

In some embodiments, the second therapeutic compound is a β2 adrenergic receptor (β2-AR) agonist such as, e.g., salmeterol, formoterol, carvedilol, salbutamol, nadolol, albuterol, olodaterol or indacaterol. Without wishing to be bound by any theory, it is anticipated that a combination therapy comprising a STAT6 inhibitor of the present invention and a β2 adrenergic receptor agonist (e.g., a long-acting beta agonist such as salmeterol, carvedilol, or formoterol, or an ultra long-acting beta agonist such as indacaterol or olodaterol) may be administered as a combination therapy, which may result in reducing or decreasing the possibility of one or more adverse effects or toxic side effects of the β2 adrenergic receptor agonist (e.g., a side-effect of the long-acting beta agonist that promotes STAT6 activation or progression of an allergic airway disease). In some embodiments, a STAT6 inhibitor of the present invention may be administered to the subject in a single pharmaceutical preparation (e.g., a metered dose inhaler, a metered dose nose spray, etc.) with the β2 adrenergic receptor agonist. In some embodiments, the STAT6 inhibitor may be administered simultaneously or sequentially with the β2-AR agonist to a subject. The STAT6 inhibitor may be in the same pharmaceutical preparation as the β2-AR agonist or a different pharmaceutical preparation than the β2-ART agonist.

Yet another aspect of the present invention relates to a method of inhibiting STAT6 in a subject comprising administering to the subject a compound of the present invention to the subject in an amount effective to inhibit STAT6. The subject may be a mammal such as, e.g., a human. The human may have an allergic lung disease or a cancer. The compound may be administered to the subject in an amount sufficient to treat the allergic lung disease or the cancer in the subject. The cancer may exhibit increased STAT5 or STAT6 expression or activity.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed.

FIG. 3: Sequences of cell penetrating phosphopeptide inhibitors of STAT6. The sequences can be found in Stolzenberg, et al., 2011, McCusker, et al., 2007, and McClusker, et al., 2011, both of which are incorporated herein by reference.

FIG. 10A: Experimental protocol.
FIG. 10B: Airway hyperreactivity as assessed in C57BL/6 mice or genotype matched mice deficient in the beta 2 adrenergic receptor ($\beta_2$-AR; $\beta_2$-AR$^{-/-}$) challenged with either control vehicle (PBS) or *A. niger* conidia (AN) and treated with either dilauroylphosphatidylcholine liposomes alone (DLPC), or DLPC and the $\beta_2$-AR ligands salmeterol (Sx), formoterol (Fx) or carvedilol (Cv) as indicated.
FIG. 10C: Airway hyperreactivity in mice challenged as in b, but comparing wild type mice to genotype matched mice deficient in beta arrestin 2 (βarr2⁻/⁻).
FIG. 10D: Bronchoalveolar lavage fluid inflammatory cells from selected mice in FIG. 10B, including total inflammatory cells, eosinophils (Eos), macrophages (mono), neutrophils (Neut) and lymphocytes (Lym). *: P<0.05, with relevant comparisons indicated.

FIGS. 11A-H: PM-242H inhibits Th cells.

FIGS. 13A-F: Treatment with PM-242H promotes recovery from airway hyperresponsiveness (AHR) and leads to inhibition of mucus production.

FIGS. 17A-C: PM-43I reverses established allergic airway disease. FIG. 17A, Mice are treated intranasally with 400,000 *Aspergillus niger* conidia every other day. After two weeks *A. niger* conidia are administered with either DLPC or DLPC/PM-43I. Airway hyperresponsiveness is measured at week 2, 3, and 4. FIG. 17B, Airway hyperrepsonsiveness induced by acetylcholine is revered by treatment with PM-43I. FIG. 17C, Treatment with PM-43I does not significantly affect immune cell recruitment and does in inhibit the lung immune response to *A. niger* infection.

FIGS. 18A-C: Activity of intranasally administered PM-43I and PM-86I is restricted to the lung. FIG. 18A, Mice are treated with STAT6 inhibitor intranasally every other day. Mice are sensitized to ovalbumin by intraperitoneal administration of OVA/Alum as indicated. In a separate cohort of mice, STAT6 inhibitors are administered 4 her prior to OVA/Alum administration. FIG. 18B, Intraperitoneal treatment with inhibitors block sensitization of Th2 cells to ovalbumin. FIG. 18C, Intranasal administration of STAT6 inhibitors has no effect on the sensisization of peripheral spleenocytes to ovalbumin.

DESCRIPTION OF ILLUSTRATIVE EMBODIMENTS

Figure 1:
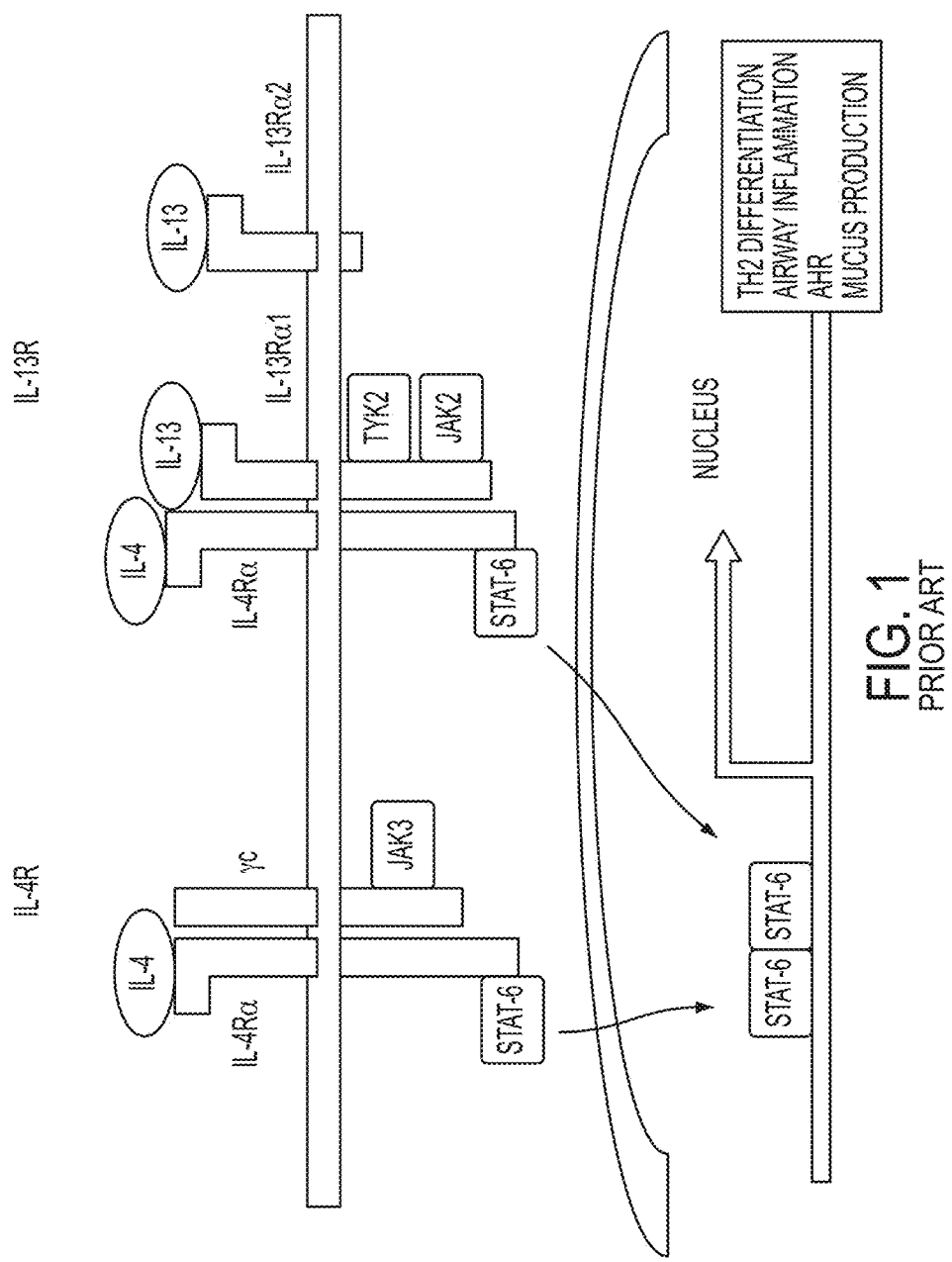
FIG. 1: The STAT6 pathway for asthma. This figure is adapted from Oh, et al., 2010, which is incorporated herein by reference.
Figure 2:
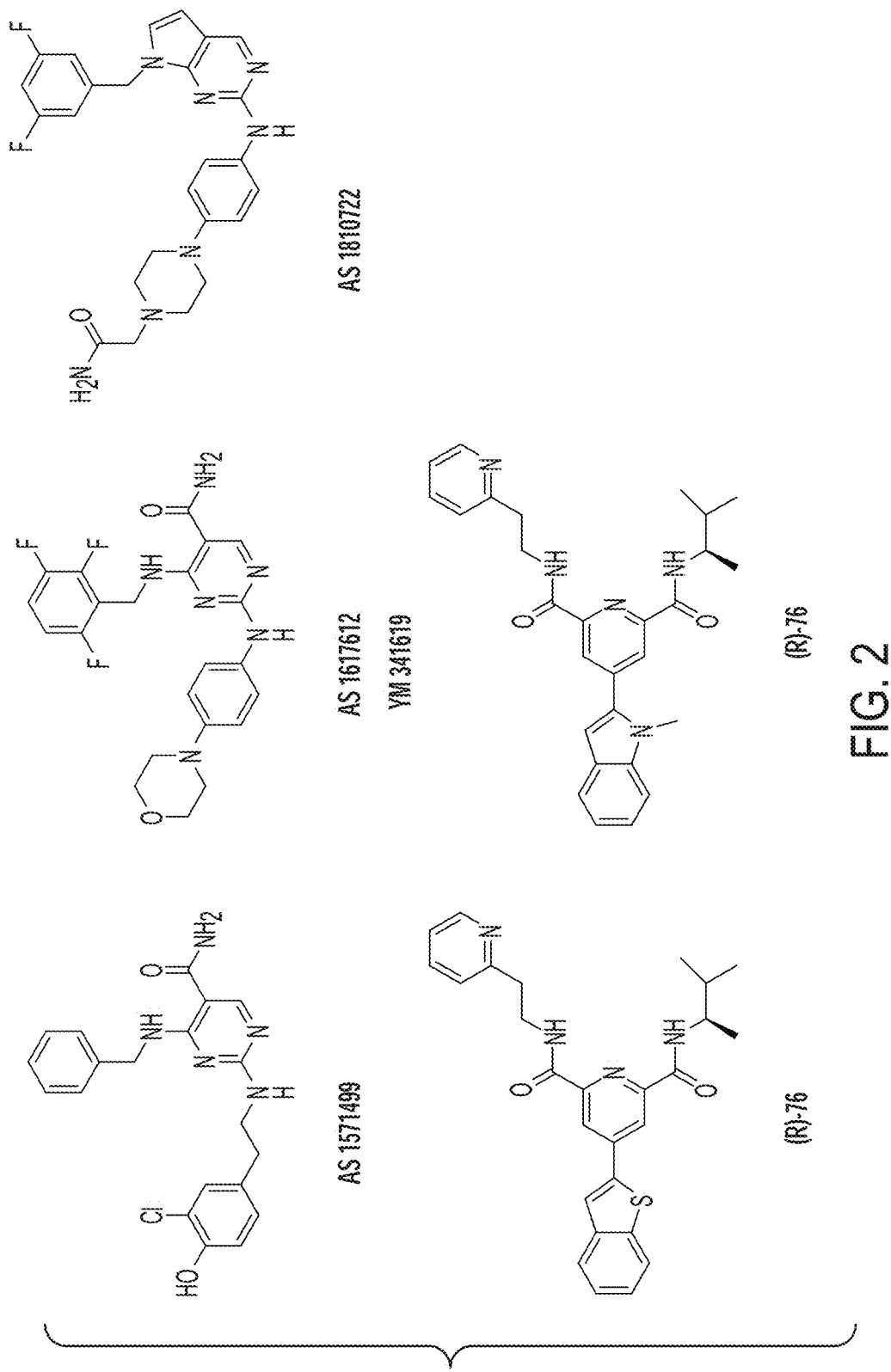
FIG. 2: A number of current small molecule inhibitors of STAT6 activity are shown.
Figure 4:
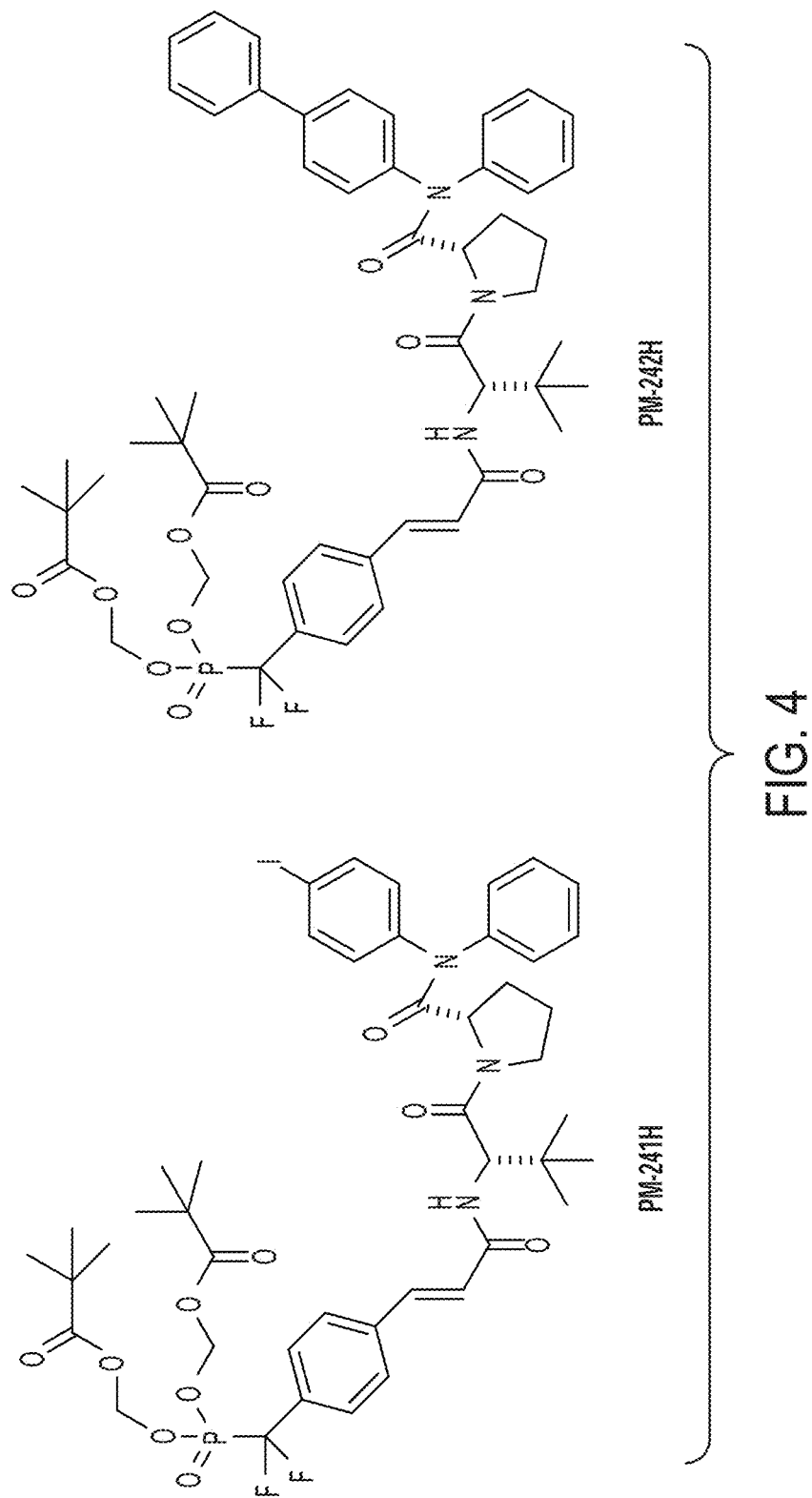
FIG. 4: Phosphopeptide mimetic prodrug candidate which was described by U.S. Pat. No. 6,426,331 and WO 2001/083517, both of which are incorporated herein by reference. The derivative PM-242H was designed and prepared by the inventors as an analog to the previously disclosed PM-241H.

In some aspects, compounds are provided that may be used to inhibit the activity of a STAT6 protein. In some embodiments, the STAT6 inhibitor is administered in a pro-drug form which is converted in vivo to the active compound through cellular processes. In some embodiments, a compound that inhibits STAT6 can be used to treat a variety of diseases including several respiratory diseases including asthma, airway hyperresponsiveness (AHR), an allergic disease, allergic rhinitis, emphysema, or chronic rhinosinusitis. Such compounds are described herein.

I. CHEMICAL DEFINITIONS

When used in the context of a chemical group: "hydrogen" means —H; "hydroxy" means —OH; "oxo" means=O; "carbonyl" means —C(=O)—; "carboxy" means —C(=O) OH (also written as —COOH or —CO₂H); "halo" means independently —F, —Cl, —Br or —I; "amino" means —NH₂; "hydroxyamino" means —NHOH; "nitro" means —NO₂; imino means=NH; "cyano" means —CN; "isocyanate" means —N=C=O; "azido" means —N₃; in a monovalent context "phosphate" means —OP(O)(OH)₂ or a deprotonated form thereof; in a divalent context "phosphate" means —OP(O)(OH)O— or a deprotonated form thereof; "mercapto" means —SH; and "thio" means=S; "sulfonyl" means —S(O)₂—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⌇" represents a single bond or a double bond. Thus, for example, the structure

includes the structures

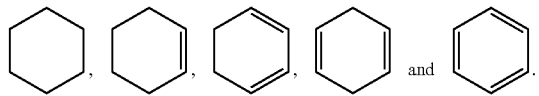

As will be understood by a person of skill in the art, no one such ring atom forms part of more than one double bond. The symbol "⌇", when drawn perpendicularly across a bond indicates a point of attachment of the group. It is noted that the point of attachment is typically only identified in this manner for larger groups in order to assist the reader in rapidly and unambiguously identifying a point of attachment. The symbol "◄" means a single bond where the group attached to the thick end of the wedge is "out of the page." The symbol "⫿⫿⫿⫿" means a single bond where the group attached to the thick end of the wedge is "into the page". The symbol "⌇" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

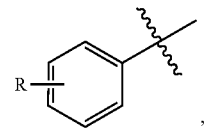

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

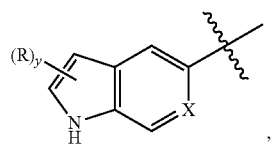

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C \leq 8)}$," or the class "alkene$_{(C \leq 8)}$," is two. For example, "alkoxy$_{(C \leq 10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). Where the term "aliphatic" is used without the "substituted" modifier, then only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

, are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. An "alkane" refers to the compound H-R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H-R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

, are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H-R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "alkyne" refers to the compound H-R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

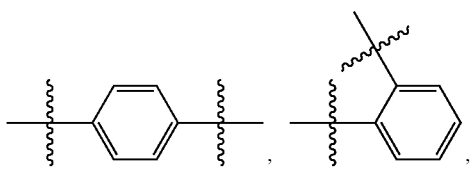

-continued

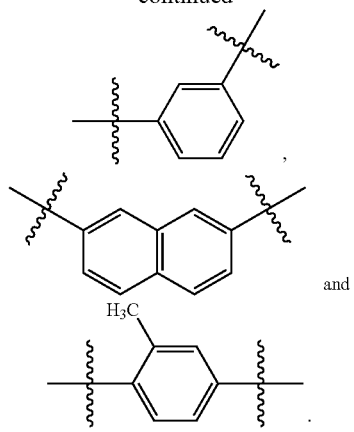

and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "arene" refers to the compound H-R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

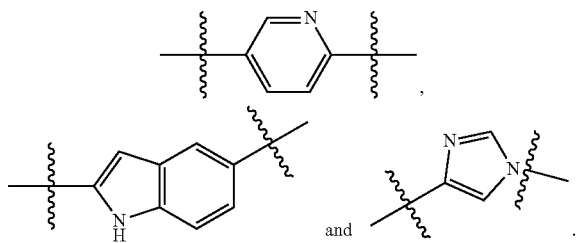

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. As used herein, the term does not preclude the presence of one or more double bonds in the ring or ring system, provided that the resulting groups remains non-aromatic. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkyl sulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. COMPOUNDS

The compounds provided by the present disclosure are shown, for example, above in the summary of the invention section and in the claims below. In some embodiments, the compound may also be described by the formula:

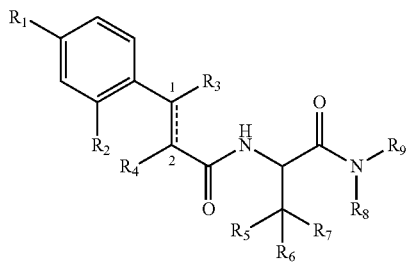

(I)

wherein: the bond between carbons 1 and 2 is a single or double bond; $R_1$ is phosphate, $-OP(O)(OR_{10})(OR_{10'})$, -alkyl$_{(C \leq 6)}$-P(O)(OR$_{10}$)(OR$_{10'}$), or a substituted version of any of these groups; wherein $R_{10}$ and $R_{10'}$ are each independently hydrogen, alkyl$_{(C \leq 6)}$, aryl$_{(C \leq 8)}$, aralkyl$_{(C \leq 12)}$, alkyl$_{(C \leq 6)}$-O—C(O)-alkyl$_{(C \leq 6)}$, alkyl$_{(C \leq 6)}$-O—C(O)-aryl$_{(C \leq 8)}$, or

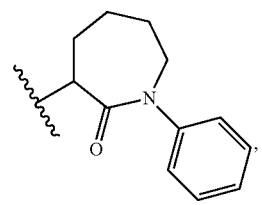

wherein m=0-8; wherein X is —CH$_2$—, —O—, —S—, or —NH—; provided that $R_{10}$ and $R_{10'}$ are not both hydrogen; $R_2$ is hydrogen or $R_2$ is taken together with $R_{11}$ as provided below; $R_3$, $R_5$, $R_6$, and $R_7$ are each independently hydrogen, unsubstituted alkyl$_{(C \leq 6)}$, or substituted alkyl$_{(C \leq 6)}$, or ($R_7$ and $R_8$) are taken together as provided below, or ($R_7$, $R_8$, and $R_9$) are taken together as provided below; $R_4$ is hydrogen or —N(R$_{11}$)R$_{12}$; wherein: $R_{11}$ is hydrogen, alkyl$_{(C \leq 6)}$, aryl$_{(C \leq 8)}$, acyl$_{(C \leq 6)}$, or a substituted version of any of these groups, or $R_{11}$ is taken together with $R_2$ as provided, below; $R_{12}$ is hydrogen, alkyl$_{(C \leq 6)}$, acyl$_{(C \leq 6)}$, or $R_{12}$ is taken together with $R_{11}$ as provided below; $R_8$ is hydrogen, unsubstituted alkyl$_{(C \leq 6)}$, substituted alkyl$_{(C \leq 6)}$, unsubstituted aryl$_{(C \leq 8)}$, substituted aryl$_{(C \leq 8)}$, an amino acid, -alkanediyl$_{(C \leq 6)}$-C(O)NX$_1$X$_2$, —CH$_2$—C(O)NX$_1$X$_2$, wherein X$_1$ and X$_2$ are each independently alkyl$_{(C \leq 6)}$, aryl$_{(C \leq 12)}$, or a substituted version of either of these groups,

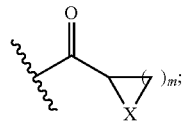

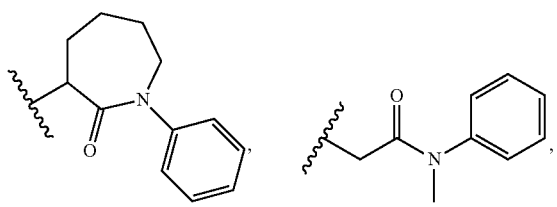

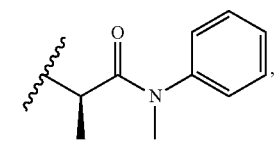

or $R_8$ is taken together with $R_7$ as provided below, or $R_8$ is taken together with $R_7$ and $R_9$ as provided below, or $R_8$ is taken together with $R_9$ as provided below; $R_9$ is hydrogen, unsubstituted alkyl$_{(C \leq 6)}$, substituted alkyl$_{(C \leq 6)}$, unsubstituted aryl$_{(C \leq 8)}$, substituted aryl$_{(C \leq 8)}$, an amino acid, -alkanediyl$_{(C \leq 6)}$-C(O)NX$_1$X$_2$, —CH$_2$—C(O)NX$_1$X$_2$, wherein X$_1$ and X$_2$ are each independently alkyl$_{(C \leq 6)}$, aryl$_{(C \leq 12)}$, or a substituted version of either of these groups,

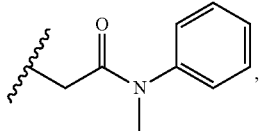

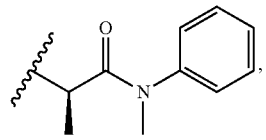

or $R_9$ is taken together with $R_7$ and $R_8$ as provided below, or $R_9$ is taken together with $R_8$ as provided below; provided that when $R_4$ is —N(R$_{11}$)R$_{12}$ and ($R_2$ and $R_{11}$) are taken together, the compound is further defined by formula IA:

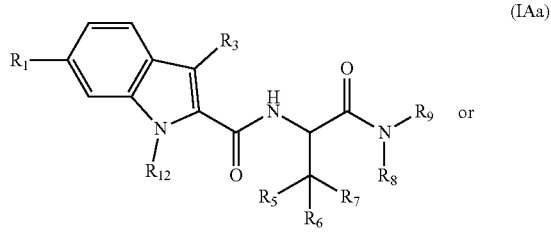

(IAa)

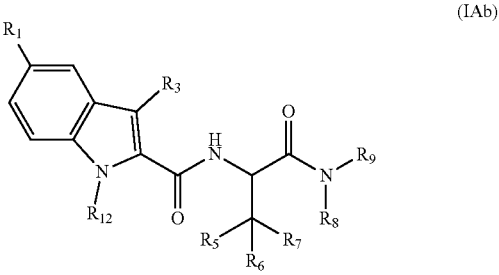

(IAb)

provided that when $R_4$ is —N(R$_{11}$)R$_{12}$ and (R$_{11}$ and R$_{12}$) are taken together, the compound is further defined by formula IB:

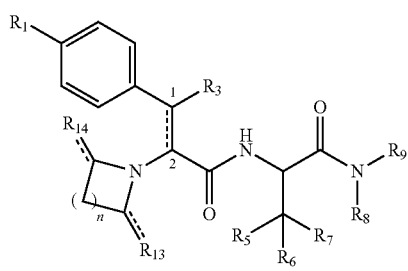

(IB)

wherein: $R_{13}$ and $R_{14}$ are each independently hydrogen or oxo; and n is 1, 2, 3, 4, or 5; provided that when $R_7$ and $R_8$ are taken together, the compound is further defined by formula IC:

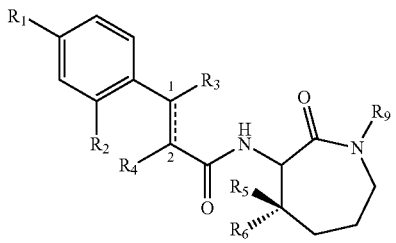

(IC)

provided that when $R_7$, $R_8$, and $R_9$ are taken together, the compound is further defined by formula ID or formula IE:

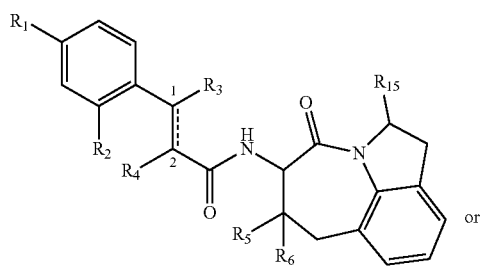

(ID)

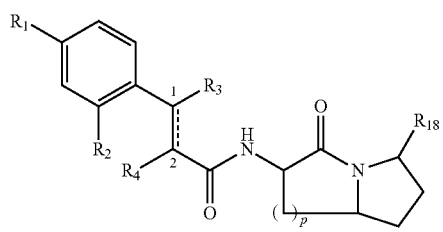

(IE)

wherein: $R_{15}$ is hydrogen or —C(O)NR$_{16}$R$_{17}$; wherein: $R_{16}$ and $R_{17}$ are each independently hydrogen, alkyl$_{(C \leq 6)}$, aryl$_{(C \leq 8)}$, or a substituted version of any of these groups; $R_{18}$ is hydrogen, -alkenediyl$_{(C \leq 6)}$-aryl$_{(C \leq 8)}$, aralkyl$_{(C \leq 12)}$, —C(O)-alkyl$_{(C \leq 6)}$, —C(O)-heterocycloalkyl$_{(C \leq 12)}$, —C(O)-heteroaryl$_{(C \leq 12)}$,

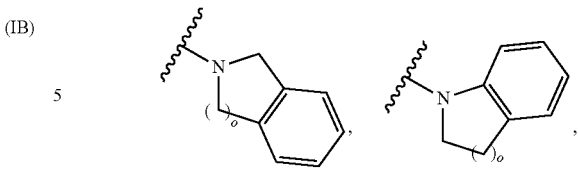

or —C(O)NR$_{19}$R$_{20}$; wherein: $R_{19}$ and $R_{20}$ are each independently hydrogen, alkyl$_{(C \leq 6)}$, aryl$_{(C \leq 8)}$, or a substituted version of either of these groups; o is 1, 2, or 3; and p is 1, 2, 3, 4, or 5; provided that when $R_8$ and $R_9$ are taken together, the compound is further defined by formula IF:

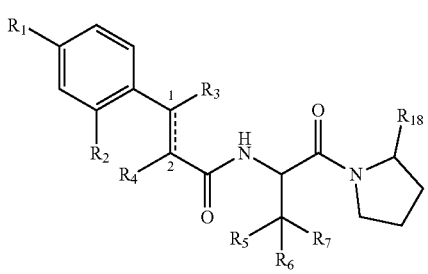

(IF)

wherein if $R_{18}$ is —C(O)NR$_{19}$R$_{20}$ and $R_{19}$ is aryl$_{(C \leq 8)}$, then $R_3$ is not hydrogen; or a pharmaceutically acceptable salt thereof. In some embodiments, the compound of formula IAa or IAb can be produced from a starting material wherein $R_1$ is para and $R_1$ is meta, respectively, and $R_2$ is ortho to the point of attachment. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein. Additionally, adjustments and modifications to the methods can be made by those skilled in the art of peptide bond formation including the principles and techniques taught, by example, in Novabiochem®, *Guide to the Selection of Building Blocks for Peptide Synthesis* (2008). Additionally, the following other structural modifications are envisioned for potential compounds contemplated by the present invention.

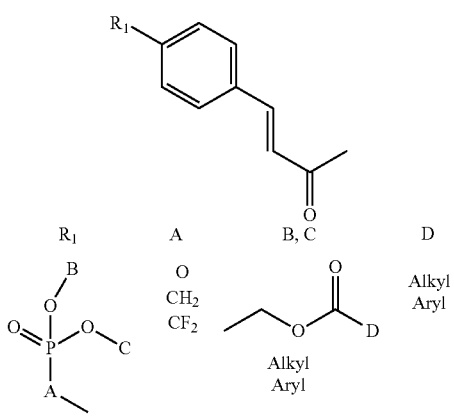

-continued

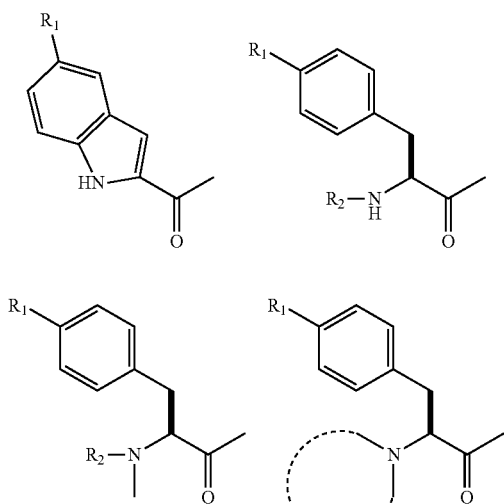

$R_2$ = alkyl, aryl, acyl

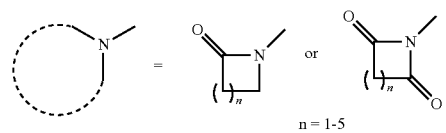

n = 1-5

Furthermore, the following core could be attached to the central ring of the tyrosine derivative:

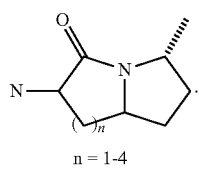

n = 1-4

In some embodiments, the compound is described by the formula:

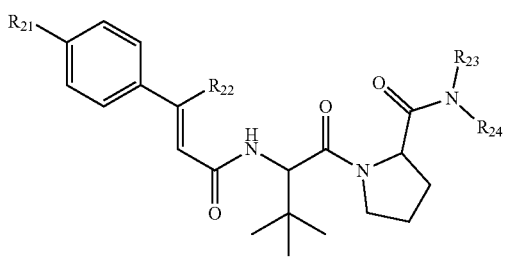
(II)

wherein: $R_{21}$ is phosphate, $-OP(O)(OR_{10})(OR_{10'})$, -alkyl$_{(C \leq 6)}$-P(O)(OR$_{10}$)(OR$_{10'}$), or a substituted version of any of these groups; wherein $R_{10}$ and $R_{10'}$ are each independently hydrogen, alkyl$_{(C \leq 6)}$, aryl$_{(C \leq 8)}$, aralkyl$_{(C \leq 12)}$, alkyl$_{(C \leq 6)}$-O-C(O)-alkyl$_{(C \leq 6)}$, alkyl$_{(C \leq 6)}$-O-C(O)-aryl$_{(C \leq 8)}$, or

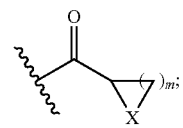

wherein m=0-8; wherein X is $-CH_2-$, $-O-$, $-S-$, or $-NH-$; provided that $R_{10}$ and $R_{10'}$ are not both hydrogen; $R_{22}$ is hydrogen or alkyl$_{(C \leq 6)}$; $R_{23}$ is hydrogen, alkyl$_{(C \leq 12)}$, substituted alkyl$_{(C \leq 12)}$, aryl$_{(C \leq 12)}$, or substituted aryl$_{(C \leq 12)}$; $R_{24}$ is aryl$_{(C \leq 12)}$ or substituted aryl$_{(C \leq 12)}$; provided that when $R_{22}$ is hydrogen then $R_{23}$ and $R_{24}$ are not both phenyl or iodophenyl; or a pharmaceutically acceptable salt thereof.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the compounds provided herein are within the scope of the invention. It will also be appreciated by those skilled in organic chemistry that many organic compounds can exist in more than one crystalline form. For example, crystalline form may vary from solvate to solvate. Thus, all crystalline forms of the compounds provided herein or the pharmaceutically acceptable solvates thereof are within the scope of the present invention.

III. PHARMACEUTICAL PREPARATIONS

Certain of the methods set forth herein pertain to methods involving the administration of a pharmaceutically and/or therapeutically effective amount of a compound of the present disclosure for purposes of treating a disease or disorder associated with STAT6 and/or STAT5. In some embodiments, the disease or disorder is asthma, airway hyperresponsiveness (AHR), an allergic disease, an allergic lung disease, allergic rhinitis, or chronic rhinosinusitis. In some embodiments, an inhibitor of STAT6 and/or STAT5 of the present invention may be administered to a subject (e.g., a mammalian subject such as a human) orally, intravenously, intranasally (e.g., via a nose spray), via inhalation or aerosol delivery, or topically to the skin or other mucus membranes (e.g., intra-rectally or by enema).

Moreover, it will be generally understood that a compound of the present disclosure can be provided in prodrug form, also discussed above, meaning that an environment to which a compound of the present disclosure is exposed alters the prodrug into an active, or more active, form. For example, one or more carboxylates on the compounds can be covered into esters which are cleaved in vivo to produce the active compound. It is contemplated that the term "precursor" covers compounds that are considered "prodrugs."

1. Pharmaceutical Formulations and Routes for Administration to Subjects

Any compound discussed herein is contemplated as comprised in a pharmaceutical composition. Pharmaceutical compositions of the present disclosure comprise an effective amount of one or more candidate substances (e.g., a compound of the present disclosure) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by the FDA's Center of Drug Evaluation and Research.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it needs to be sterile for such routes of administration as injection. The present disclosure can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, subcutaneously, subconjunctival, intravesicularlly, mucosally, buccally, transdermally, intrapericardially, intraumbilically, intraocularally, orally, locally, via inhalation (e.g., aerosol inhalation), via injection, via infusion, via continuous infusion, via localized perfusion bathing target cells directly, via a catheter, via eye or ear drops, via a lavage, in cremes, in lipid compositions (e.g., liposomes), or by other method or any combination of the foregoing as would be known to one of ordinary skill in the art (see, for example, Remington's Pharmaceutical Sciences, 1990).

In some embodiments, one or more STAT6 inhibitor of the present invention may be administered intranasally or to the lungs of a subject. For example, the STAT6 inhibitor may be administered in a nose spray such as a metered dose nose spray, an inhaler, or in a nebulizer (e.g., a mechanical nebulizer such as a soft mist inhaler, a human powered nebulizer, or an electrical nebulizer such as vibrating mesh technology (VMT) nebulizer, a jet nebulizer, an ultrasonic wave nebulizer). As would be appreciated by one of skill, intranasal delivery and/or delivery to the lungs may be particularly useful for treating a disease affecting the nose or lungs such as, e.g., an allergic rhinitis or an allergic lung disease, etc.

A composition comprising a compound of the present disclosure may be formulated for topical administration, for example, in a cream as mentioned, or in an ointment, salve, spray, gel, lotion, or emulsion. The composition may be formulated for transmucosal, transepithelial, transendothelial, or transdermal administration. One example of transdermal formulation is a patch. The composition may further comprise a chemical penetration enhancer, a membrane permeability agent, a membrane transport agent, a preservative, a surfactant, or a stabilizer, as these terms are known to those of skill in the art.

In one topical embodiment, the present disclosure can utilize a patch. A transdermal or "skin" patch is a medicated adhesive patch that is placed on the skin to deliver a time released dose of medication through the skin and into the bloodstream. A wide variety of pharmaceuticals can be delivered by transdermal patches. The main components to a transdermal patch are (a) a liner to protect the patch during storage (removed prior to use); (b) the active agent; (c) an adhesive that serves to adhere the components of the patch together along with adhering the patch to the skin; (d) a membrane to control the release of the drug from the reservoir and multi-layer patches; and (e) a backing that protects the patch from the outer environment.

There are four main types of transdermal patches. Single-layer Drug-in-Adhesive patches have an adhesive layer that also contains the agent. In this type of patch the adhesive layer not only serves to adhere the various layers together, along with the entire system to the skin, but is also responsible for the releasing of the drug. The adhesive layer is surrounded by a temporary liner and a backing. Multi-layer Drug-in-Adhesive patches are similar to the single-layer system in that both adhesive layers are also responsible for the releasing of the drug. The multi-layer system is different however that it adds another layer of drug-in-adhesive, usually separated by a membrane (but not in all cases). This patch also has a temporary liner-layer and a permanent backing. Reservoir patches are unlike the Single-layer and Multi-layer Drug-in-Adhesive systems in that the reservoir transdermal system has a separate drug layer. The drug layer is a liquid compartment containing a drug solution or suspension separated by the adhesive layer. This patch is also backed by the backing layer. In this type of system the rate of release is zero order. Matrix patches have a drug layer of a semisolid matrix containing a drug solution or suspension. The adhesive layer in this patch surrounds the drug layer partially overlaying it.

In another form of treatment, a topical application of a compound of the present disclosure is targeted at a natural body cavity such as the mouth, pharynx, esophagus, larynx, trachea, pleural cavity, peritoneal cavity, or hollow organ cavities including the bladder, colon or other visceral organs. A variety of methods may be employed to affect the topical application into these visceral organs or cavity surfaces. For example, the pharynx may be affected by simply oral swishing and gargling with solutions comprising a compound of the present disclosure.

In particular embodiments, the composition is administered to a subject using a drug delivery device. Any drug delivery device is contemplated for use in delivering a pharmaceutically effective amount of a compound of the present disclosure.

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent. The administration could be intra-operative or post-operative.

In certain embodiments, pharmaceutical compositions may comprise, for example, at least about 0.1% of a compound of the present disclosure. In other embodiments, a compound of the present disclosure may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg/body weight, about 5 milligram/kg body weight, about 10 milligram/kg/body weight, about 20 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg/body weight to about 500 milligram/kg body weight, etc., can be administered, based on the numbers described above. In some embodiments, a metered dose of the STAT6 inhibitor may be administered to a subject, such as a human patient; for example about 10 µg-1 mg, about 50-500 µg, about 50-300 µg, 75-275 µg, or about 100-200 µg may be administered to the subject (e.g., intranasally or via inhalation).

In any case, the composition may comprise various anti-oxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral, or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, glycolic, lactic, tartaric, or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, TRIS, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye or ear drops, nasal solutions or sprays, aerosols or inhalants in the present disclosure. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the disclosure, the oral composition may be prepared as a syrup or elixir. A syrup or elixir, and may comprise, for example, at least one active agent, a sweetening agent, a preservative, a flavoring agent, a dye, a preservative, or combinations thereof.

Dosage formulations of the present pharmaceutical compositions can be prepared by combining them with a pharmaceutically acceptable carrier, such as a slow release agent, to make either immediate or slow release formulations as is well known in the art. Such compositions could be used, for example, in the treatment of periodontal disease and other oral care indications. Such pharmaceutically acceptable carriers may be either solid or liquid in form such as, for example, cornstarch, lactose, sucrose, peanut oil, olive oil, sesame oil, propylene glycol and water. If a solid carrier is used, the dosage formulation of the present pharmaceutical compositions may be in, for example, powder, troche, or lozenges form. If a liquid carrier is used, the dosage formulation of the present pharmaceutical compositions may be in, for example, soft gelatin capsule, syrup liquid suspension, emulsion, or solution form. The dosage formulations may also contain adjuvants, such as preserving, stabilizing, wetting or emulsifying agents, or solution promoters. Immediate and slow release formulations are well known in the art and have been described, for example, in U.S. Pat. No. 4,764,377 (the disclosure of which is incorporated herein by reference), which describes a method for treating periodontal disease by means of a delivery device placed within the periodontal pocket so that release of a therapeutic agent occurs in the immediate vicinity of the disease process. Other means of treating periodontal disease are described in U.S. Pat. No. 5,324,756, the entire contents of which are incorporated herein by reference.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Certain coating materials are those which dissolve at about or at least about a pH of 5 or above, such as at about pH 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0 or above, such as pH of about 6.5 or above. Such coatings therefore only begin to dissolve when they have left the stomach and entered the small intestine. Accordingly, these coatings may be considered enteric coatings. A thick layer of coating is provided which will dissolve in minutes to hours, thereby allowing the capsule underneath to breakup only when it has reached the terminal ileum or the colon. Such a coating can be made from a variety of polymers such as cellulose acetate trimellitate (CAT), hydroxypropylmethyl cellulose phthalate (HPMCP), polyvinyl acetate phthalate (PVAP), cellulose acetate phthalate (CAP) and shellac. For coatings of cellulose esters, a thickness of 200-250 µm would be suitable.

Non-limiting exemplary coating materials are methyl methacrylates or copolymers of methacrylic acid and methyl methacrylate. Such materials are available as EUDRAGIT™ polymers (Rohm Pharma, Darmstadt, Germany). Eudragits are copolymers of methacrylic acid and methyl methacrylate. Compositions may be based on EUDRAGIT™ L100 and Eudragit S100. EUDRAGIT™ L100 dissolves at pH 6 and upwards and comprises 48.3% methacrylic acid units per g dry substance; EUDRAGIT™ S100 dissolves at pH 7 and upwards and comprises 29.2% methacrylic acid units per g dry substance. Certain coating compositions are based on EUDRAGIT™ L100 and EUDRAGIT™ S100 in the range 100 parts L100:0 parts S100 to 20 parts L100:80 parts S100. A non-limiting exemplary range is 70 parts L100:30 parts S100 to 80 parts L100:20 parts S100. For formulations where the ratio of EUDRAGIT™ L100:S100 is high, a coat thickness of the order 150-200 µm is preferable. This is equivalent to 70-110 mg of coating for a size 0 capsule. For coatings where the ratio EUDRAGIT™ L100:S100 is low, a coat thickness of the order 80-120 µm is preferable, equivalent to 30 to 60 mg coating for a size 0 capsule.

It is specifically contemplated that compounds of the present disclosure may be incorporated into the polymers that act as carriers that are nonabsorbable. Compounds of the present disclosure may be, for example, covalently bonded to such polymers. Such polymers may be, for example, the polymers mentioned above and/or the polymer tails and polymer backbones discussed herein.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsions, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

2. Combination Therapy

In order to increase the effectiveness of a compound of the present disclosure, a compound of the present disclosure may be combined with other efficacious drugs. It is contemplated that this type of combination therapy may be used in vitro or in vivo.

For example, a compound of the present disclosure may be provided in a combined amount with an effective amount of a second agent (or more) a modulation of the side effects of the other drug. This process may involve administering the agents at the same time or within a period of time wherein separate administration of the substances produces a desired therapeutic benefit. This may be achieved by contacting the cell, tissue, biofilm, or organism with a single composition or pharmacological formulation that includes two or more agents, or by contacting the cell with two or more distinct compositions or formulations, wherein one composition includes one agent and the other includes another.

The compounds of the present disclosure may precede, be co-current with and/or follow the other agents by intervals ranging from minutes to weeks. In embodiments where the agents are applied separately to a cell, tissue, biofilm, or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered within or substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein a compound of the present disclosure is "A" and a second agent is "B":

| |
|---|
| A/B/A B/A/B B/B/A A/A/B A/B/B B/A/A A/B/B/B B/A/B/B |
| B/B/B/A B/B/A/B A/A/B/B A/B/A/B A/B/B/A B/B/A/A |
| B/A/B/A B/A/A/B A/A/A/B B/A/A/A A/B/A/A A/A/B/A |

The second agent "B" may be a steroid, an antihistamine, a bronchodilator (e.g., short-acting β-2 agonist, a long-acting β2 agonist, or an anticholinergic), an anti-inflammatory steroid, or an antihistamine, or an anti-fungal antibiotic or any combination of these agents. The anti-inflammatory steroid may be a corticosteroid such as, e.g., fluticasone or beclomethasone. In some embodiments, the second agent is a non-inhaled therapeutic agent such as, e.g., a leukotriene receptor modifier (e.g., montelukast), and anti-IgE antibody (e.g., omalizumab), magnesium, theophylline, an allergen immunotherapy, or an oral or intravenous corticosteroid (e.g., prednisone, methylprednisolone). In embodiments where a compound of the present invention is used to treat a cancer in a subject, the second agent may be a chemotherapy, a radiotherapy, a gene therapy, or an immunotherapy.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: STAT6 Inhibitors

The STAT6 pathway is described in FIG. 1. FIG. 1 provides a general background on the molecular pathway leading to STAT6's involvement in asthma.

A. Inhibition of STAT6 Functions with Phosphopeptides Targeting the SH2 Domain

Using a modular phosphopeptide prodrug synthesis methodology described in Mandal, et al., 2011 and Mandal, et al., 2009, both of which are incorporated herein by reference, to prepare compound PM-241H. During the synthesis, the iodine of PM-241H was substituted with a phenyl group leading to a second and more efficacious prodrug, PM-242H.

Figure 5:
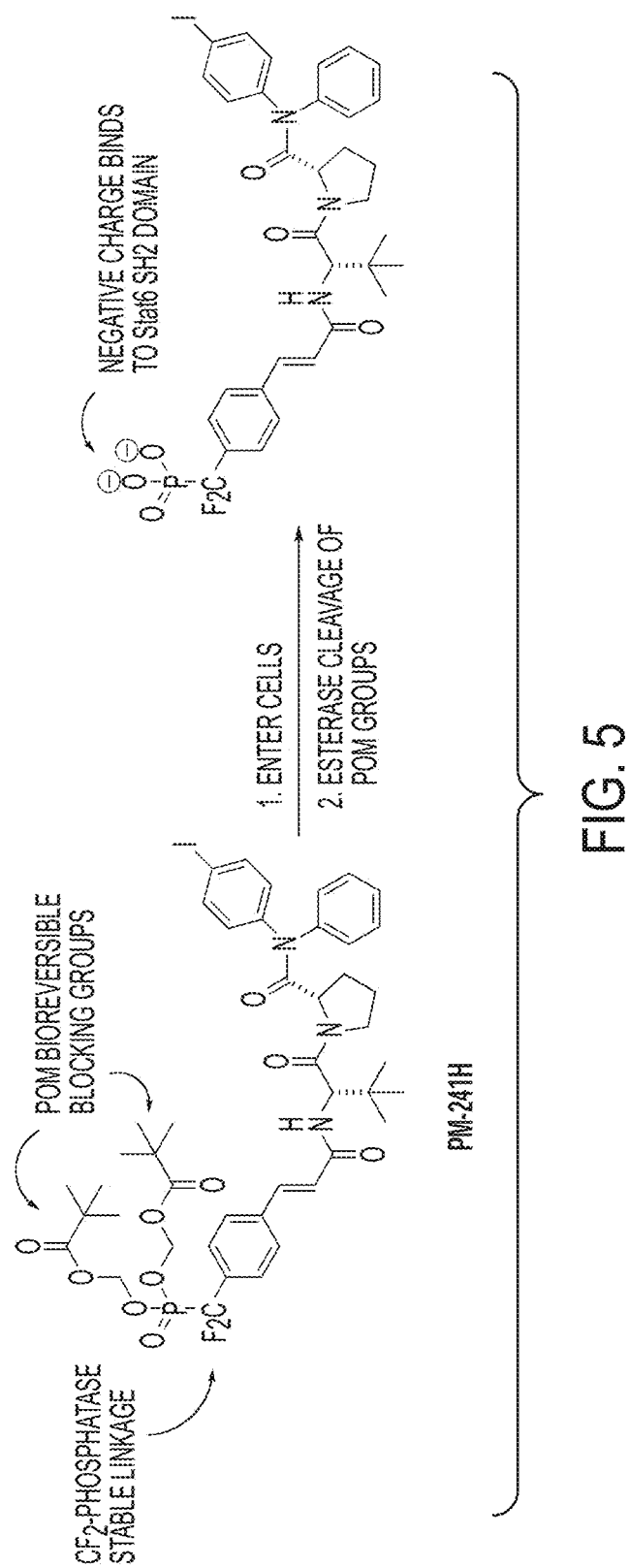
FIG. 5: Schematic description of the mechanism by which the POM group acts as a prodrug increasing the cell permeability of the compound.

In these inhibitors, the phosphate group is replaced with the difluoromethylphosphonate group to prevent cleavage by phosphatases and thus enhance efficacy. The negative charges are blocked with carboxyesterase-labile pivaloyloxymethyl (POM) groups. Phosphotyrosine was replaced with the conformationally constrained cinnamate group. Substituents on the C-terminal amide nitrogen impart affinity for the SH2 domain of STAT6. On entering the cell, the POM groups are cleaved releasing the bis-negatively charged inhibitor for interaction with the SH2 domain. (FIG. 5).

Figure 6:
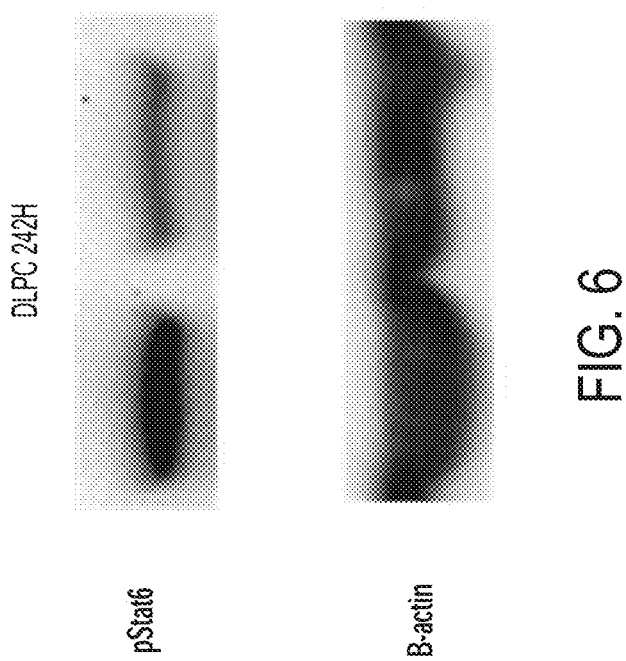
FIG. 6: Gel images of the effects of PM-242H on STAT6 phosphorylation and β-actin compared to the effects of control compound DLPC.

Compound PM-241H inhibited the phosphorylation of Tyr641 of STAT6 in Beas-2B cells stimulated with IL-4 and IL-13. Partial inhibition was observed at 1 μM and complete inhibition occurred at 10 μM. PH-242H also showed similar activity which can be seen in FIG. 6.

B. Phosphates

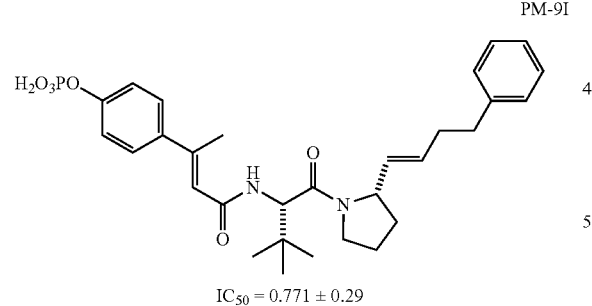

PM-9I $IC_{50} = 0.771 \pm 0.29$

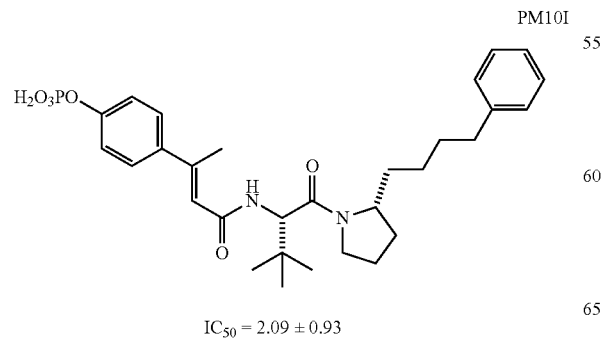

PM10I $IC_{50} = 2.09 \pm 0.93$

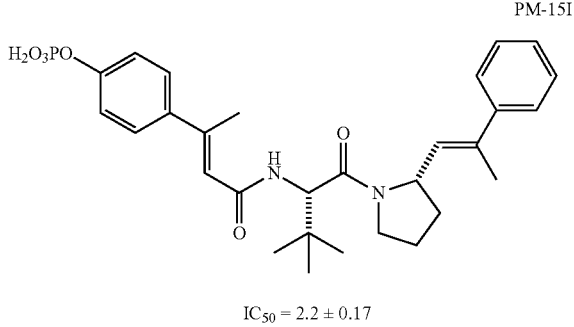

PM-15I $IC_{50} = 2.2 \pm 0.17$

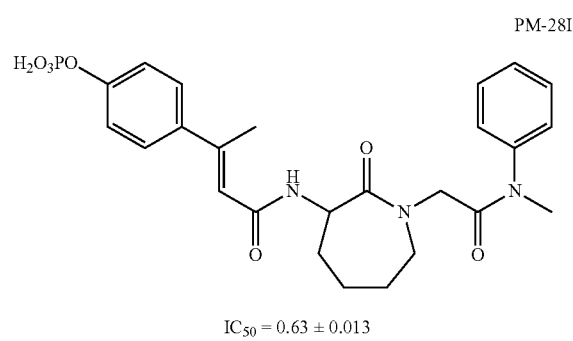

PM-28I $IC_{50} = 0.63 \pm 0.013$

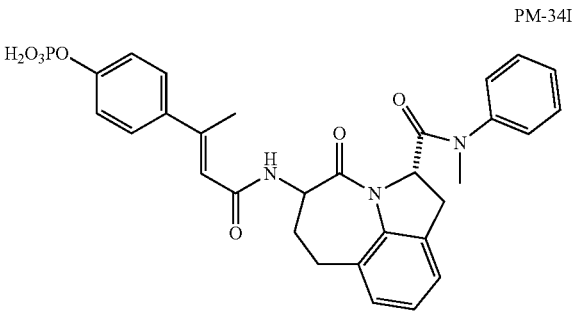

PM-34I $IC_{50} = 0.28 \pm 0.06$

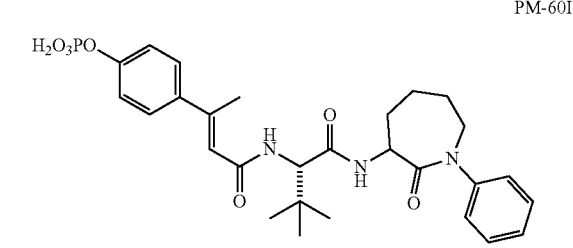

PM-60I $IC_{50} = 2.33 \pm 0.5$

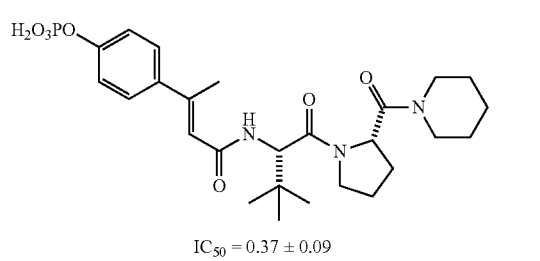

PM-67I-A $IC_{50} = 0.37 \pm 0.09$

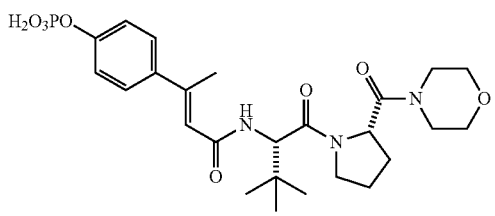

PM-67I-B

IC$_{50}$ = 0.103 ± 0.05

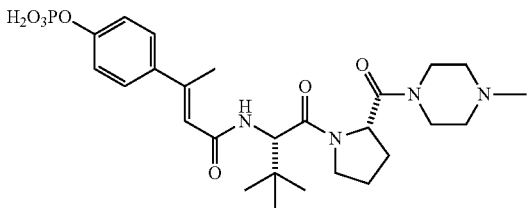

PM-67I-C

IC$_{50}$ = 0.9 ± 0.84

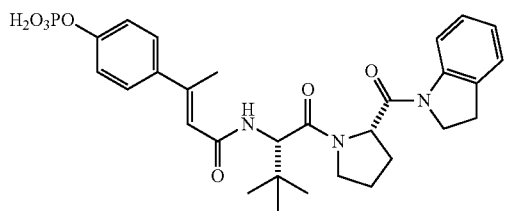

PM-59I

IC$_{50}$ = 0.26 ± 0.09

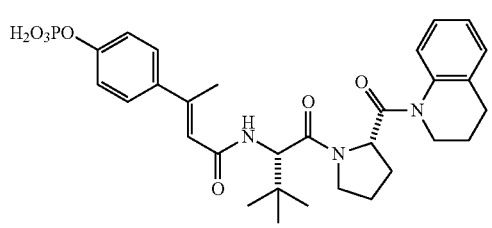

PM-87I

IC$_{50}$ = 0.24 ± 0.13

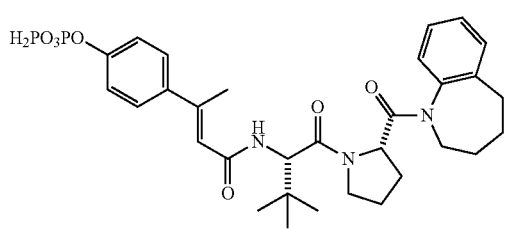

PM-71I-B

IC$_{50}$ = 0.23 ± 0.12

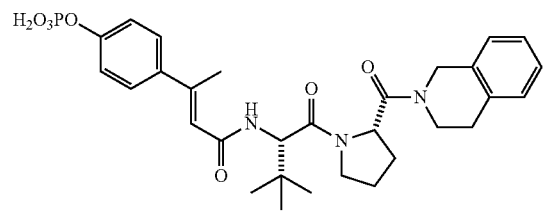

PM-71I-A

IC$_{50}$ = 0.05 ± 0.04

Select phosphate-containing STAT6 inhibitors provided herein. All IC$_{50}$ values are shown in μM.

| Compound | IC$_{50}$ (μM) |
|---|---|
| PM-9I | 0.771 ± 0.29 |
| PM-10I | 2.09 ± 0.93 |
| PM-15I | 2.2 ± 0.17 |
| PM-28I | 0.63 ± 0.013 |
| PM-34I | 0.28 ± 0.06 |
| PM-60I | 2.33 ± 0.5 |
| PM-67I-A | 0.37 ± 0.09 |
| PM-67I-B | 0.103 ± 0.05 |
| PM-67I-C | 1.9 ± 0.84 |
| PM-59I | 0.26 ± 0.09 |
| PM-87I | 0.24 ± 0.13 |
| PM-71-A | 0.05 ± 0.04 |
| PM-71-B | 0.23 ± 0.12 |

The following structures as phosphate esters were synthesized and assayed them for the ability to compete with FAM-Ala-pTyr-Lys-Pro-Phe-Gln-Asp-Leu-Ile-NH$_2$, derived from Tyr631 of IL-4Rα, for binding to STAT6 using fluorescence polarization (FAM=5-carboxyfluorescein). The fluorescence polarization methodology was adapted from Wu et al., 1997, which is incorporated herein by reference. Amide bond replacements, cyclic amides, and cyclic lactams in the central part of the compound were explored.

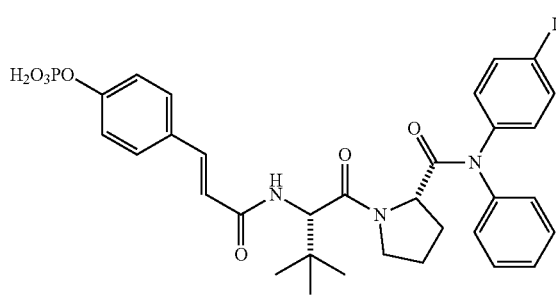

PM-287H

IC$_{50}$ = 0.073 ± 0.01

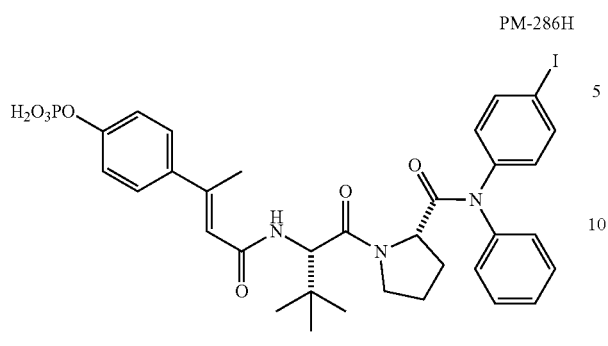

PM-286H

IC$_{50}$ = 0.053 ± 0.01

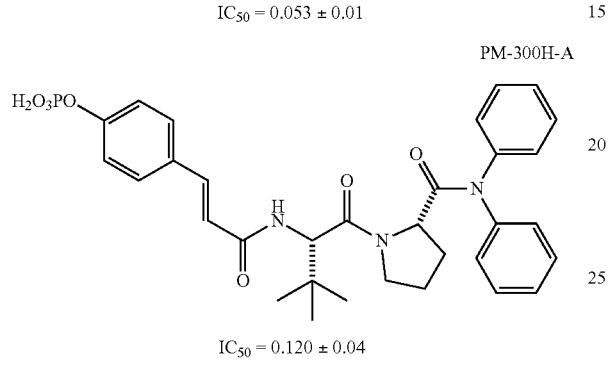

PM-300H-A

IC$_{50}$ = 0.120 ± 0.04

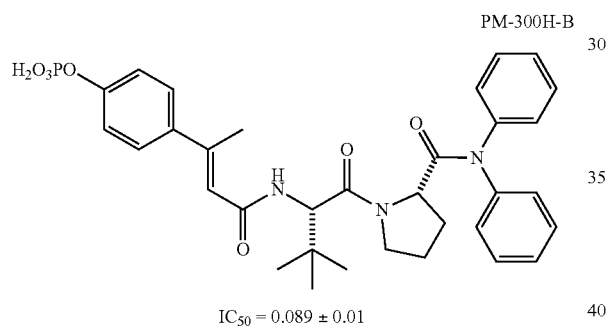

PM-300H-B

IC$_{50}$ = 0.089 ± 0.01

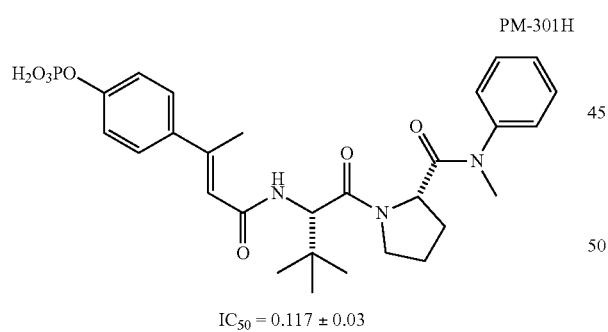

PM-301H

IC$_{50}$ = 0.117 ± 0.03

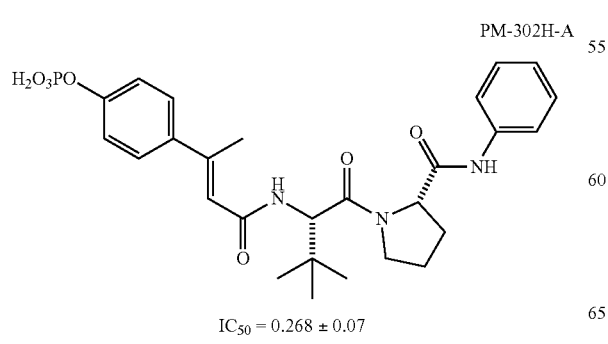

PM-302H-A

IC$_{50}$ = 0.268 ± 0.07

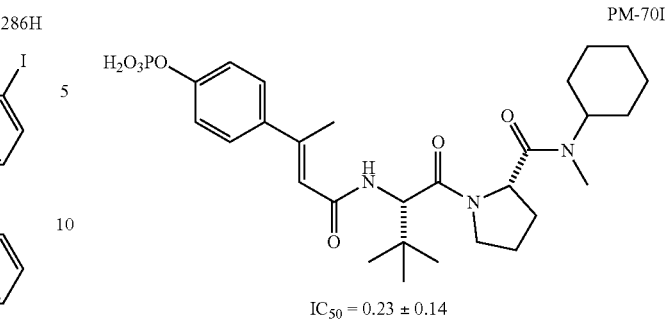

PM-70I

IC$_{50}$ = 0.23 ± 0.14

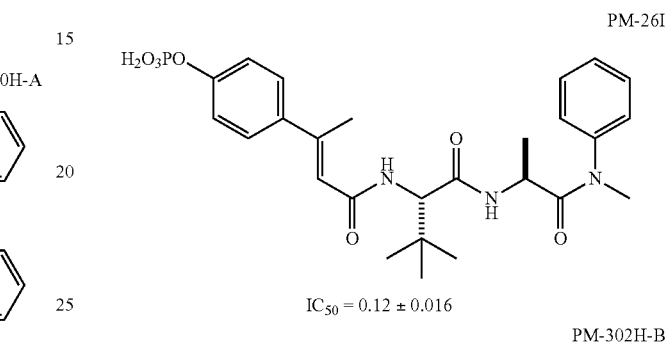

PM-26I

IC$_{50}$ = 0.12 ± 0.016

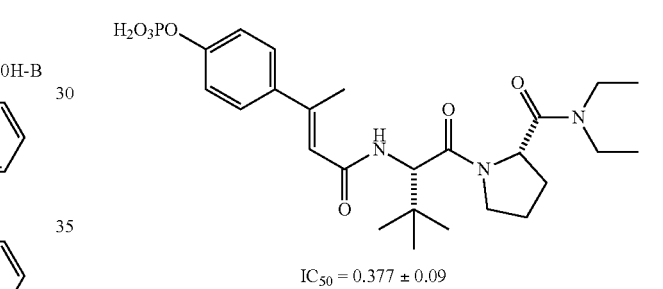

PM-302H-B

IC$_{50}$ = 0.377 ± 0.09

Other Phosphate-containing STAT6 inhibitors synthesized. All IC$_{50}$ values are shown in μM.

| Compound | IC$_{50}$ (μM) |
|---|---|
| PM-287H | 0.073 ± 0.01 |
| PM-286H | 0.053 ± 0.01 |
| PM-300H-A | 0.120 ± 0.04 |
| PM-300H-B | 0.089 ± 0.01 |
| PM-301H | 0.117 ± 0.03 |
| PM-302H-A | 0.268 ± 0.07 |
| PM-70I | 0.23 ± 0.14 |
| PM-26I | 0.12 ± 0.016 |
| PM-302H-B | 0.377 ± 0.09 |

TABLE 1

Characterization of phosphate-bearing inhibitors of STAT6 SAR of C-terminus.

| Compound | MS Calcd (M + H) | MS Found (M + H) | HPLC RT (min) |
|---|---|---|---|
| PM-9I | 555.2624 | 555.2867 | 24.52 |
| PM-10I | 557.2780 | 557.2827 | 25.52 |
| PM-15I | 527.2311 | 527.2312 | 20.47 |
| PM-28I | 516.1900 | 516.1879 | 14.40 |
| PM-34I | 576.1900 | 576.1874 | 17.47 |
| PM-60I | 558.2369 | 558.2347 | 17.20 |
| PM-67I-A | 536.2526 | 536.2573 | 13.53 |
| PM-67I-B | 538.2318 | 538.2334 | 10.92 |
| PM-67I-C | 551.2635 | 551.2683 | 9.47 |

TABLE 1-continued

Characterization of phosphate-bearing inhibitors of STAT6 SAR of C-terminus.

| Compound | MS Calcd (M + H) | MS Found (M + H) | HPLC RT (min) |
|---|---|---|---|
| PM-59I | 570.2369 | 570.2342 | 19.26 |
| PM-87I | 584.2526 | 584.2516 | 19.18 |
| PM-71I-A | 598.2682 | 598.2690 | 19.42 |
| PM-71I-B | 584.2526 | 584.2533 | 17.75 |

C. Phosphatase-Stable, Cell-Permeable Prodrugs

In the phosphatase-stable prodrugs, cyclic amide, bicyclic amide or caprolactams groups were incorporated into phosphatase-stable, cell-permeable prodrugs and assayed for the ability to inhibit STAT6 phosphorylation in immortalized human airway cells. Synthesis was carried out using the modular, convergent technology developed for Stat3 inhibitors (Scheme I) described below and included Mandal, et al., 2011 and Mandal, et al., 2009, both of which are incorporated herein by reference. In short, cinnamic acid derivatized at (a), the 4 position of the aromatic ring with bis-pivaloyloxymethyl phosphonodifluormethyl groups, (b), at the β or 3 position of the alkene with either a hydrogen or a methyl group, and (c), the carboxy group esterified as a pentachlorophenyl or 4-nitrophenyl ester, was coupled to amines of varying structure.

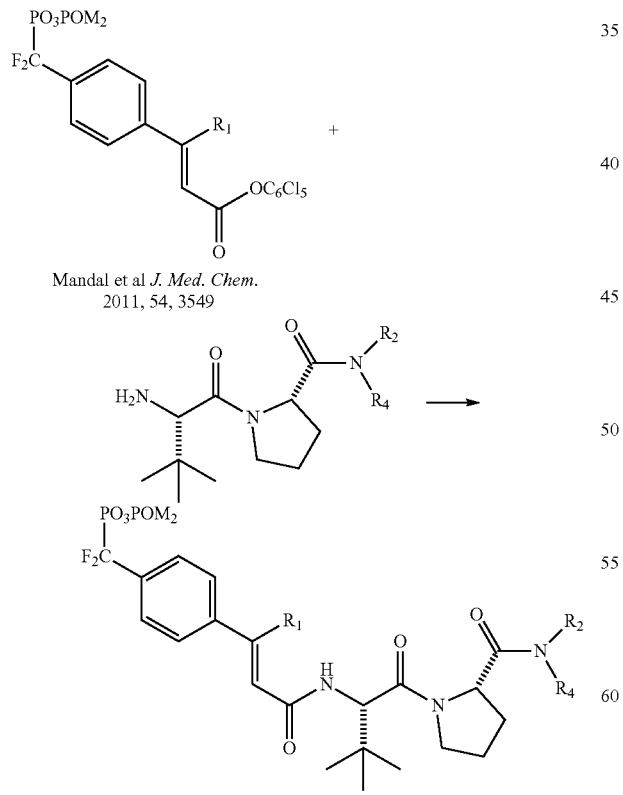

Scheme I.
Modular synthesis of prodrugs targeting the SH2 domain of STAT6.

$R_1$ = H, $CH_3$
$R_2$ - variable
$R_3$ = variable

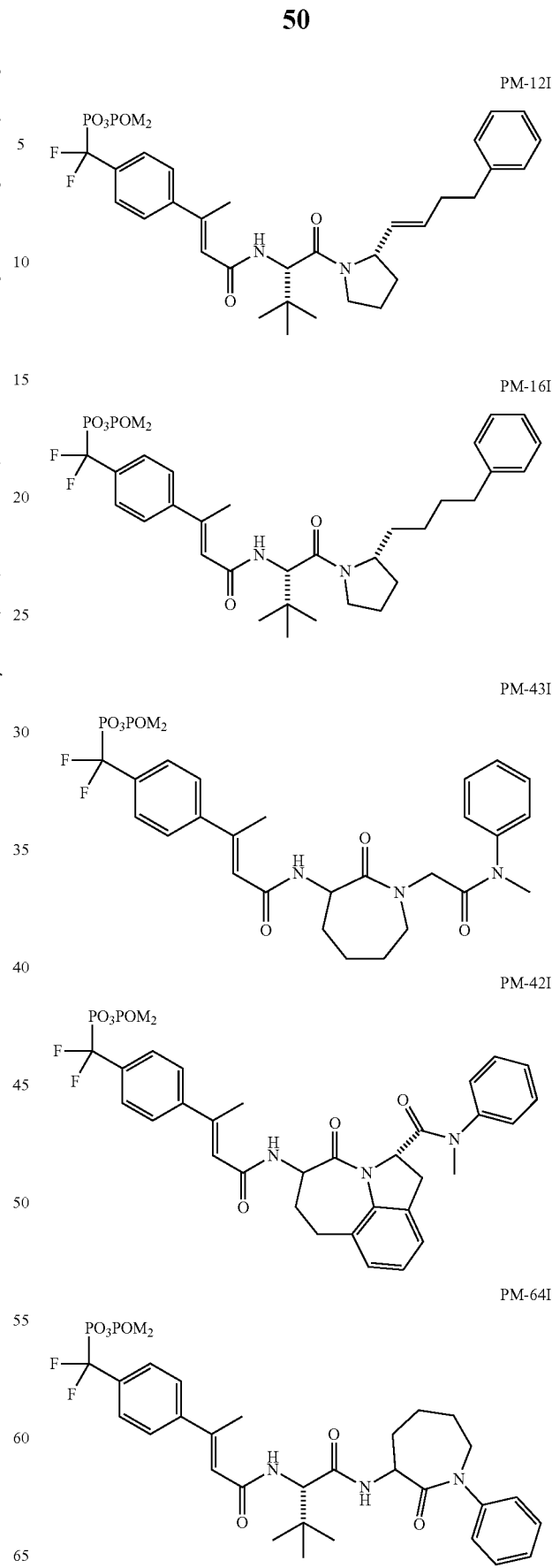

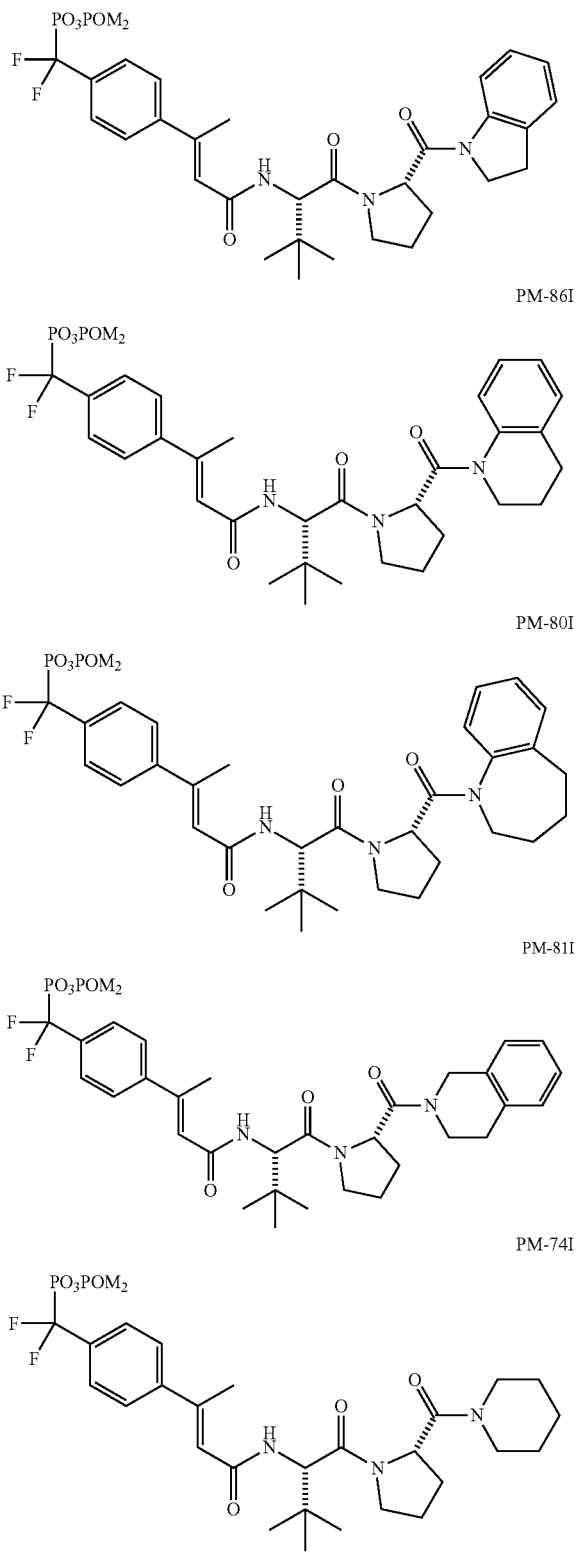

Cell-Permeable STAT6 Inhibitors are Shown Above.

Figure 7:
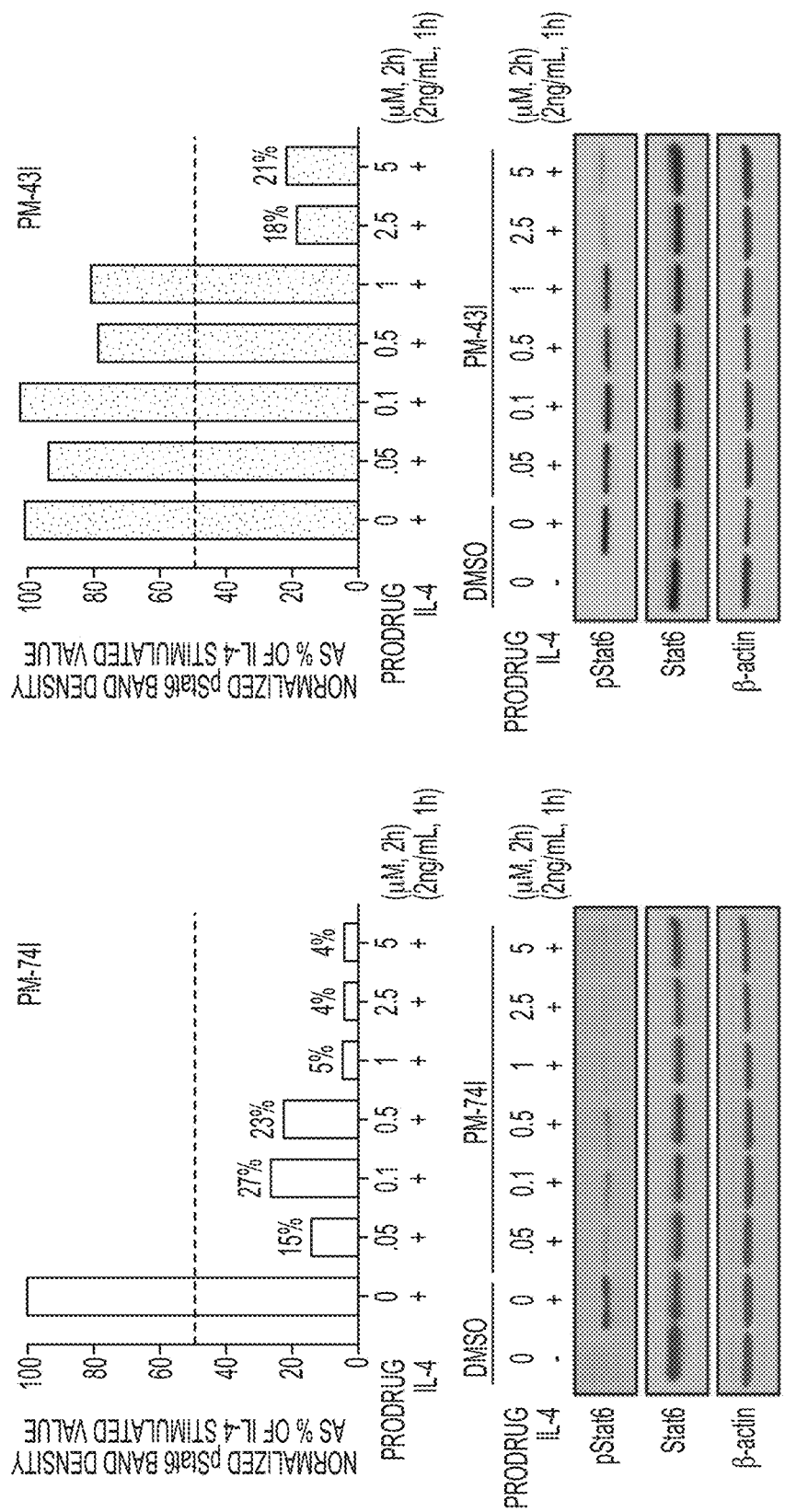
FIG. 7: Gel images of the effects of several inhibitors described herein on STAT6 phosphorylation and β-actin. Each inhibitor shows the gel of the concentration of inhibitor and the percent inhibition observed for the compound at a range of concentrations from 0 to 5 µM.
Figure 7:
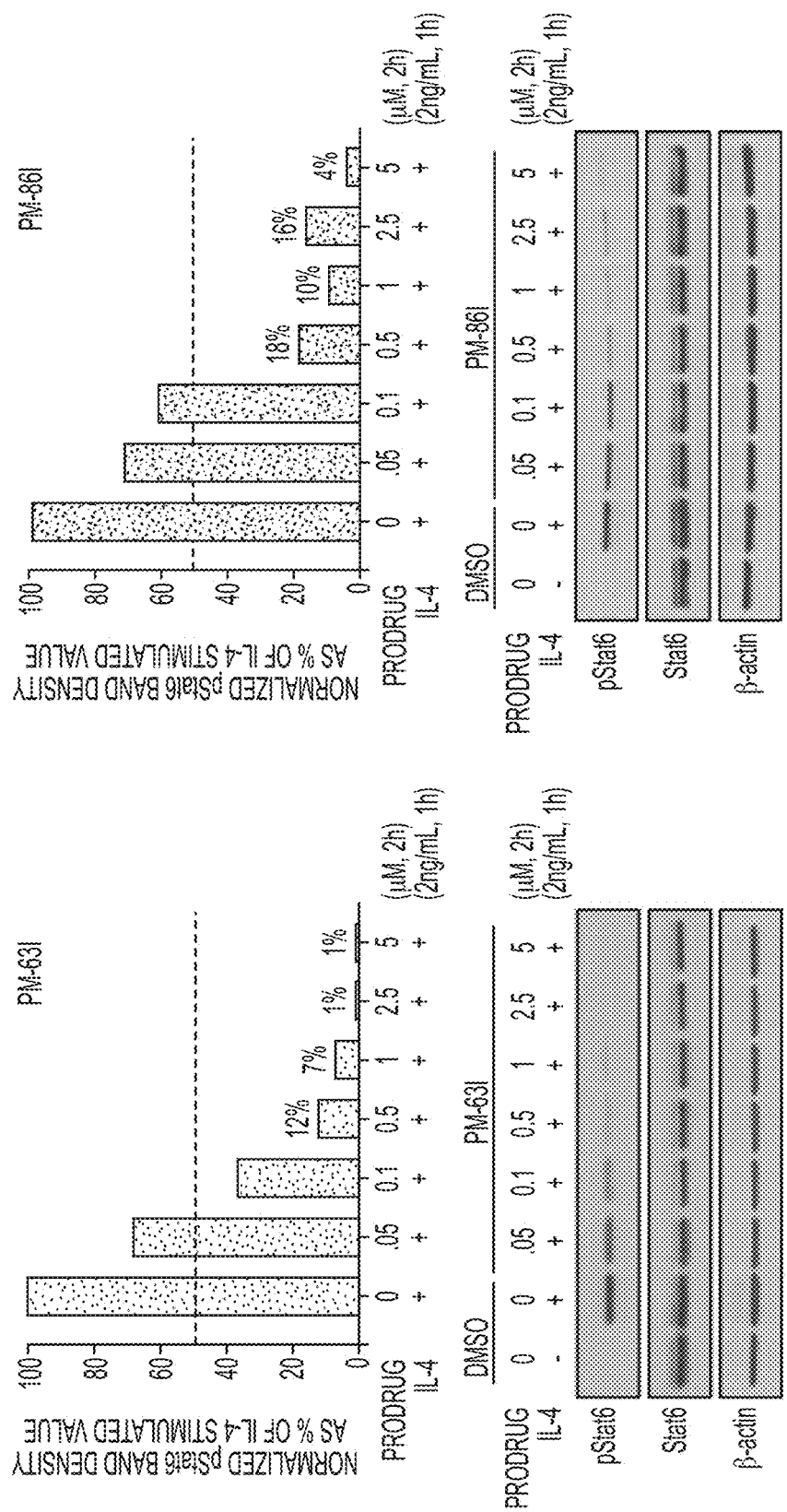
Figure 7:
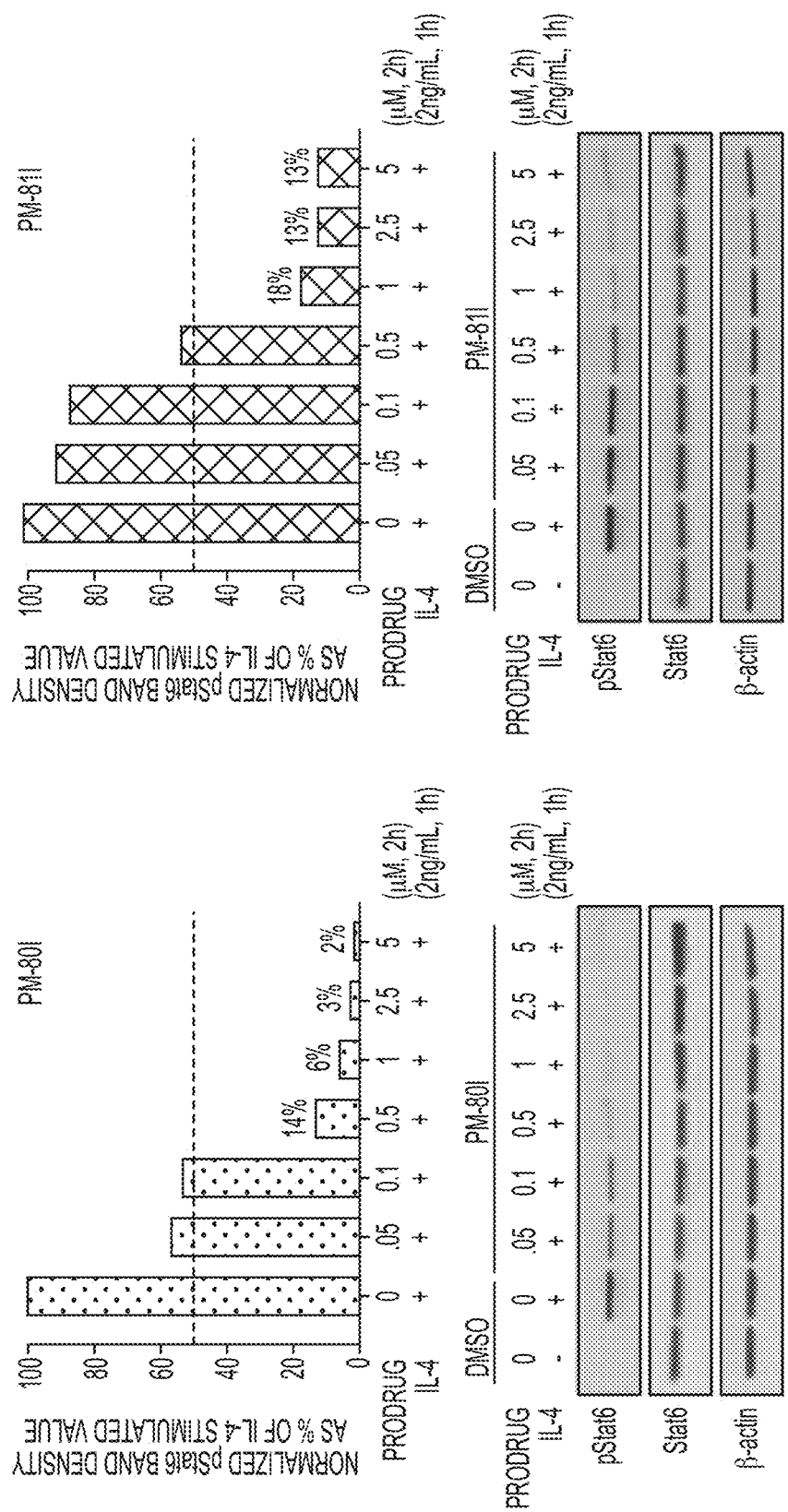
Figure 8:
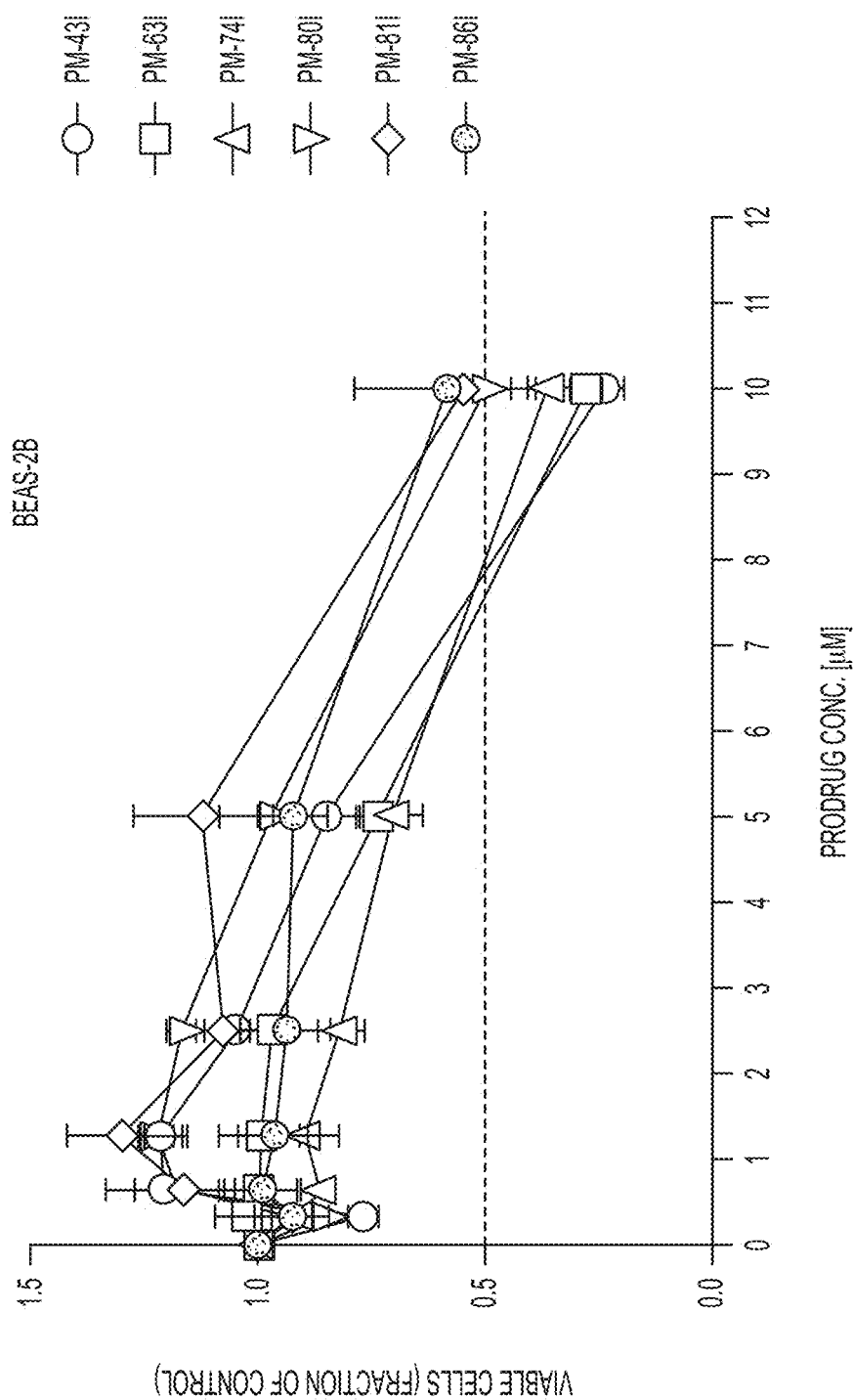
FIG. 8: Dose-response inhibition of STAT6 phosphorylation and effect on proliferation of Beas-2B cells.
Figure 9A:
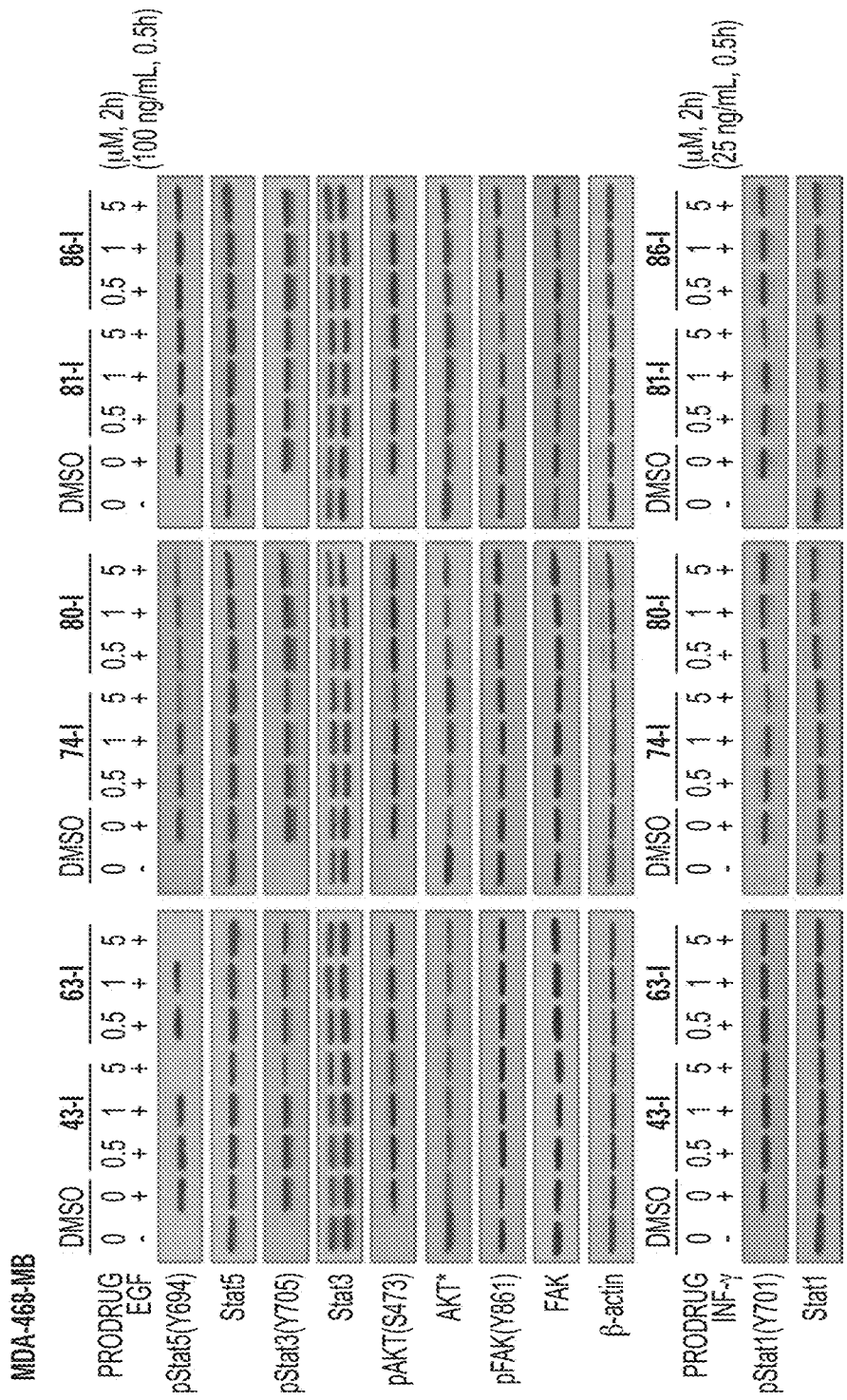
FIGS. 9A-B: In vitro selectivity study of inhibitors 43-I, 63-I, 74-I, 80-I, 81-I, and 86-I in MDA-468-MB (FIG. 9A) and the effects on proliferations (FIG. 9B).
Figure 9B:
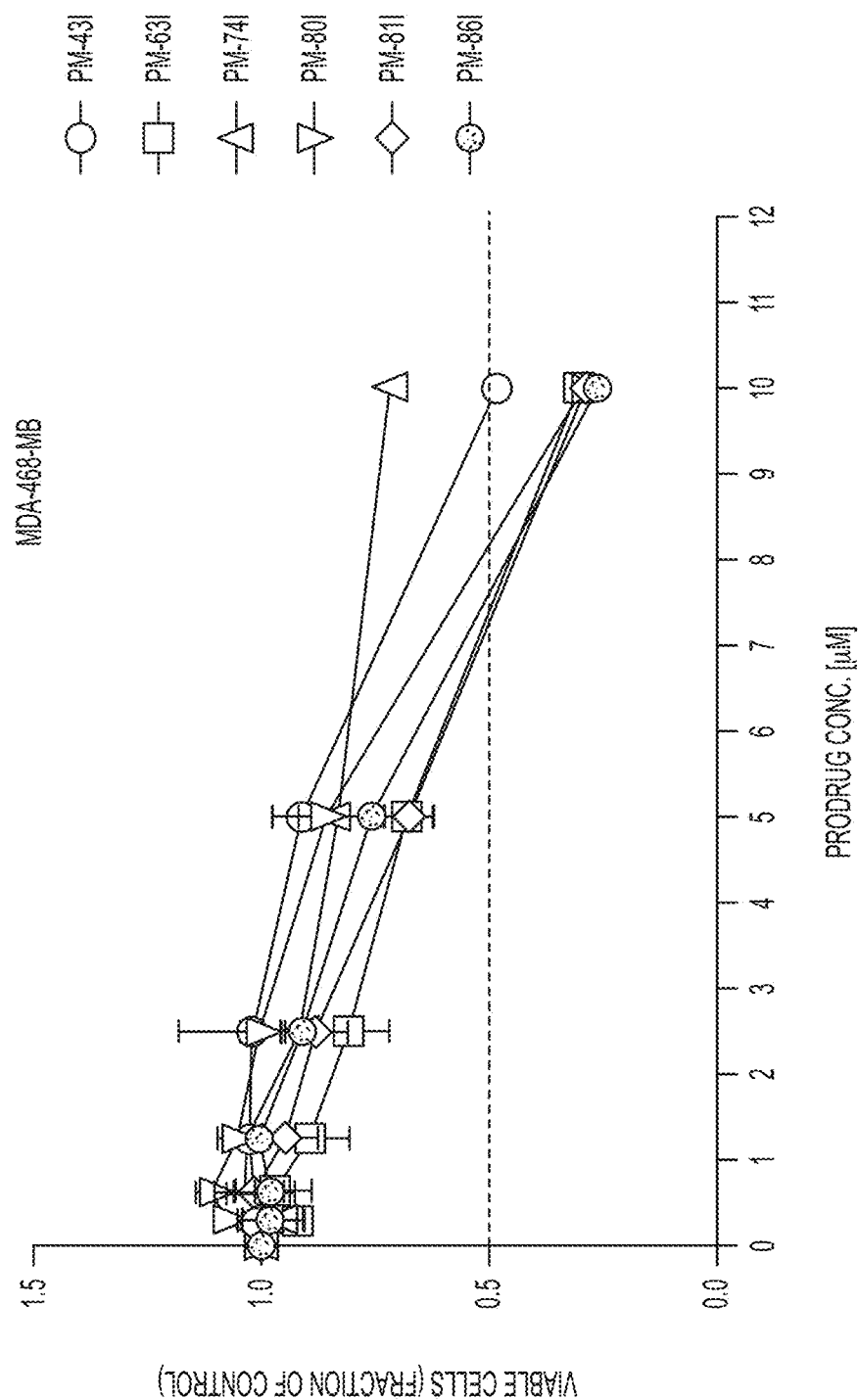
Figure 10B:
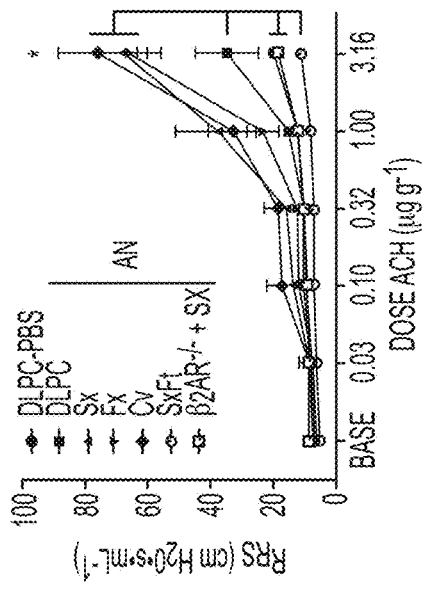
FIGS. 10A-10D: Long-acting beta agonists enhance the expression of allergic airway disease.
Figure 10D:
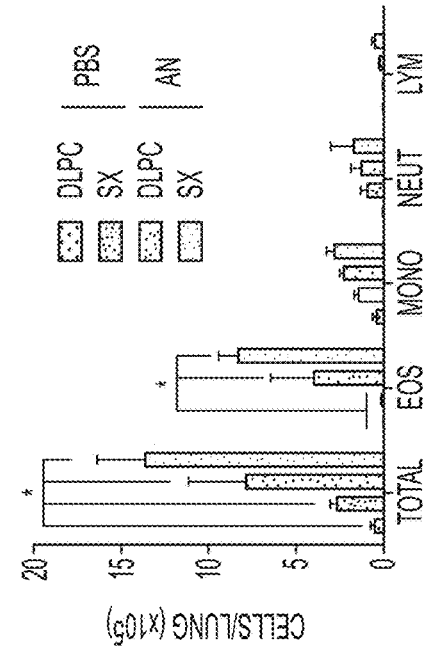
Figure 10A:
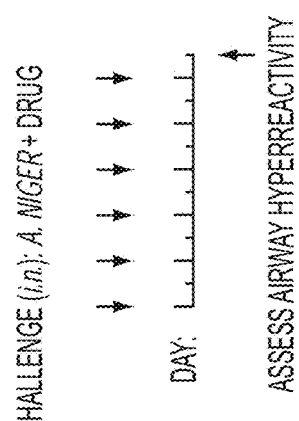
Figure 10C:
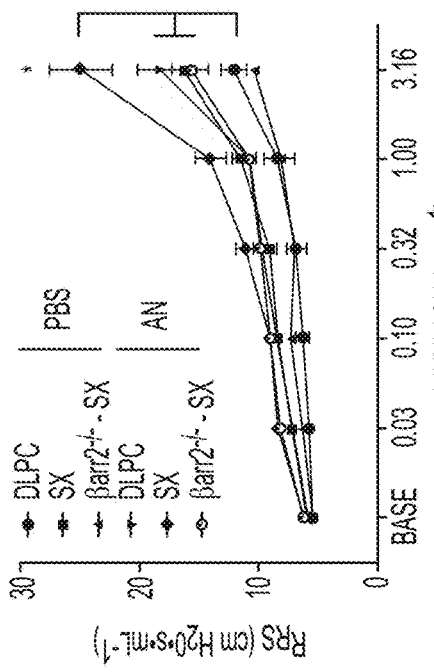

Compounds were screened at 5 µM for their ability to inhibit IL-4 stimulated phosphorylation of STAT6 in Beas-2B immortalized human airway cells. Cells were treated with prodrug for 2 hr and then stimulated with IL-4. After 30 min cells were lysed and pSTAT6 and total STAT6 were measured with western blots (FIG. 7). Without being bound by theory, the inhibition observed is consistent with compounds entering cells, being stripped of the POM groups, binding to the SH2 domain of STAT6, blocking binding to IL-4Rα and preventing phosphorylation of Tyr641. PM-73I, which has no phosphonate and thus cannot bind to the SH2 domain of STAT6, did not inhibit STAT6 phosphorylation indicating that the phosphonate group is required to inhibit STAT6 phosphorylation. Compounds resulting in <10% residual phosphorylation were taken on to MTS cytotoxicity assays and dose response assays. (FIG. 8). The cyclic aromatic amides PM-63I, PM-80I, PM-81I, and PM-86I were very potent with $IC_{50}$ values from 50-500 nM. Interestingly, the non-aromatic piperidine amide, PM-74I was also very potent with and $IC_{50}$ of 50 nM. Lactam PM-43I was not as potent, $IC_{50}$ was between 1 and 2.5 µM. With the exception of PM-43I, concentrations that inhibit STAT6 phosphorylation are 20-100 fold lower than those resulting in toxicity. STAT6 inhibitors were assayed for their ability to inhibit the phosphorylation of STAT 1, STAT 3, STAT 5, Akt, and FAK, all processes that depend on SH2 domain-phosphotyrosine interactions (Mandal, P. K. et al. 2011). Serum starved MDA-MB-468 breast cancer cells were treated with STAT6 inhibitors for 2 hr and then were stimulated with EGF (See FIGS. 9A and 9B). Most compounds did not inhibit the other processes at 5 µM. However, PM-43I and PM-63I showed significant cross reactivity with Stat5.

TABLE 2

Structures and characterization, of prodrug inhibitors of STAT6.

| Compound | MS Calcd (M + H) | MS Found (M + H) | HPLC RT (min) |
|---|---|---|---|
| PM-12I | 803.3848 | 803.3840 | 35.55 |
| PM-16I | 775.3535 | 775.3570 | 34.47 |
| PM-43I | 778.3280 | 778.3268 | 30.56 |
| PM-42I | 838.3280 | 838.3302 | 33.41 |
| PM-64I | 820.3750 | 820.3764 | 33.92 |
| PM-74I | 798.3906 | 798.4006 | 33.00 |
| PM-63I | 832.3750 | 832.3790 | 35.20 |
| PM-86I | 846.3906 | 846.3918 | 34.3 |
| PM-80I | 860.4063 | 860.4112 | 35.78 |
| PM-81I | 846.3906 | 846.3908 | 34.54 |

D. Inhibitors Decrease Development of Th Cells

Figure 11E:
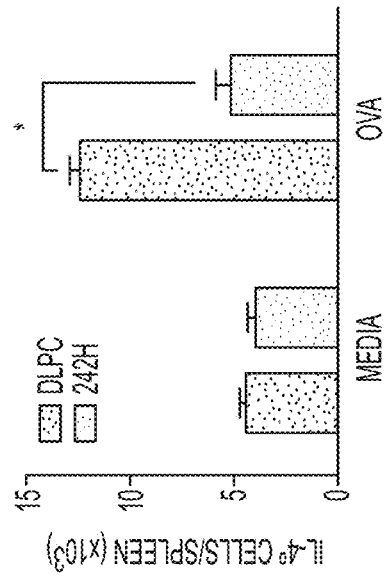
Figure 11F:
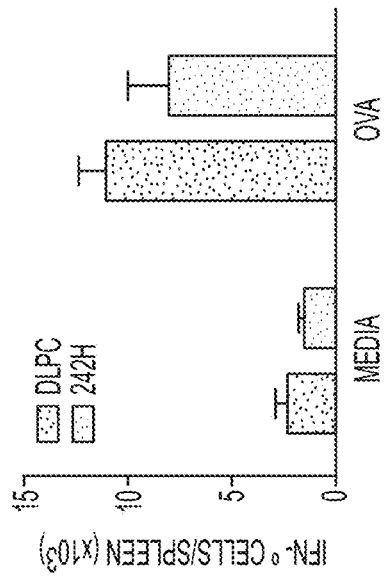
Figure 11G:
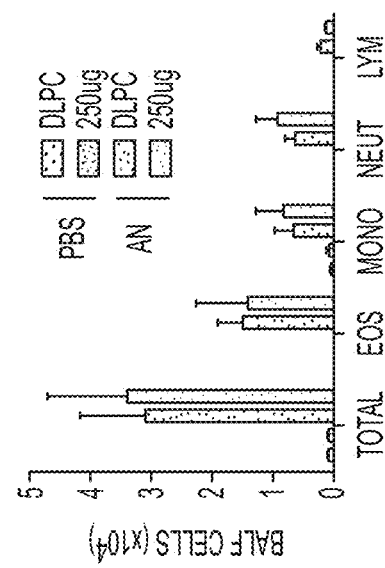
Figure 11H:
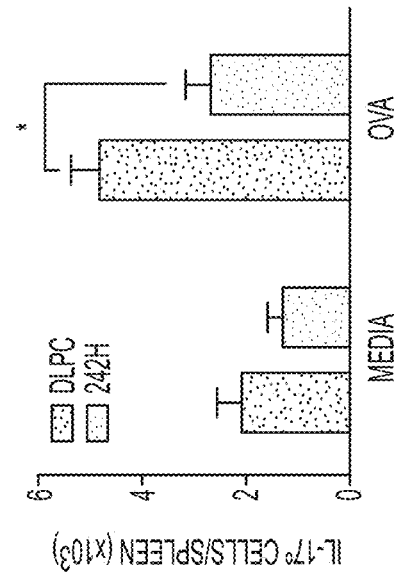
Figure 12:
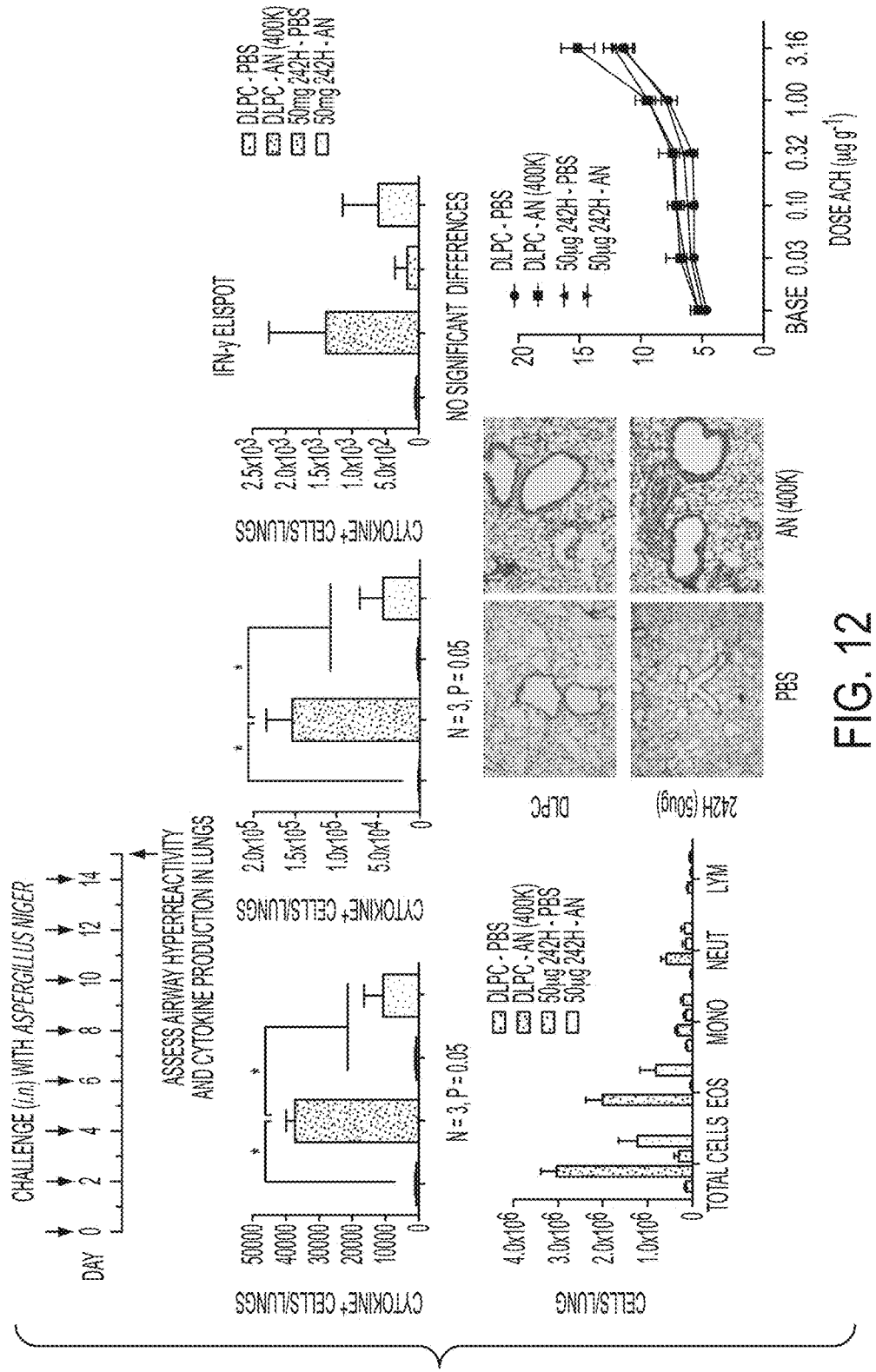
FIG. 12: Treatment with PM-242H blocks the development of allergic lung disease.
Figure 14:
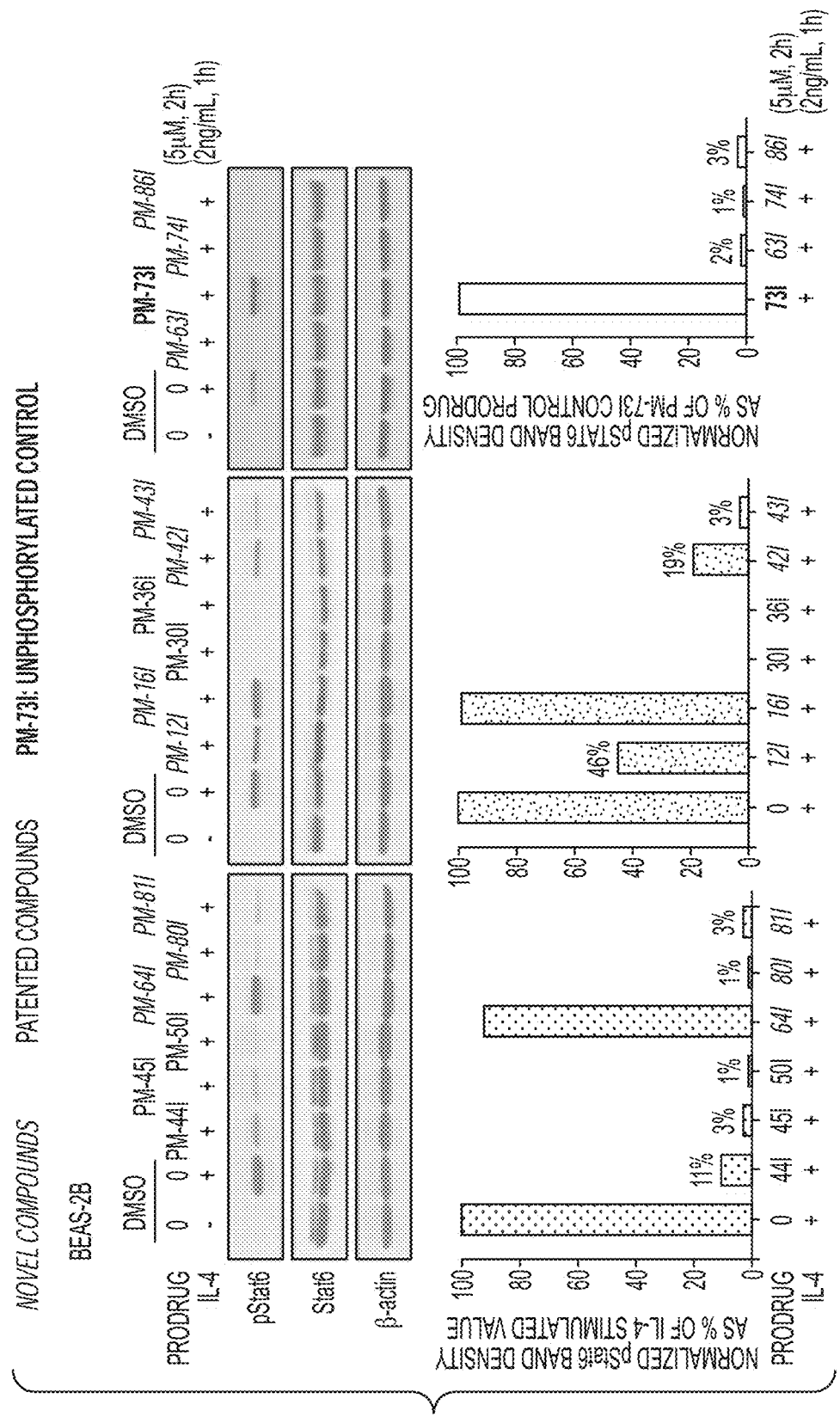
FIG. 14: Initial screening for inhibition with a variety of disclosed inhibitors using BEAS-2B cell line.

The ability of PM-242H to inhibit the development of major T helper effector subsets (Th1, Th2, Th17 cells) at the time of allergen exposure was tested. For these experiments, mice were immunized with chicken egg ovalbumin precipitated in alum over two weeks and then challenged intranasally with the spores of the fungus *Aspergillus niger* (AN) together with alum-free ovalbumin. The inventors prepared single cell suspensions of splenocytes from these same mice and stimulated the T cells in these preparations with ovalbumin to determine the precise number of antigen-specific Th1, Th2 and Th17 cells that developed. This in vitro restimulation assay showed that Th2 (IL-4-producing) and Th17 (IL-17A-producing) T cells failed to develop, whereas Th1 (gamma interferon (IFN-γ))-secreting cells were unaffected by PM-242H (FIG. 11F-H). In summary, treatment of mice with PM-242H suppressed the development of Th2 and Th17, but not Th1 cells. These findings are entirely consistent with the known properties of STAT6, but in addition indicate that STAT6 may be involved with the production of Th17 cells.

E. In Vivo Inhibition of Asthma

The following is included to demonstrate that this class of compounds inhibits asthma symptoms in murine models. The synthesized PM-242H compound was advanced to in vivo studies. PM-242H was formulated as simple dilauroyl-phosphatidyl-choline liposomes and applied by intranasal administration. This formulation demonstrated ability to 1) inhibit TH2 cell development in vivo, 2) inhibit the generation of airway hyperresponsiveness and other features of asthma-like disease in a mouse model when given prophylactically, and 3) when given therapeutically, i.e., given after the disease phenotype has already become established. PM-242H has been shown to inhibit STAT6 phosphorylation both in vitro and in vivo. These findings with PM-242H in vivo and in vitro are entirely consistent with and explained by its ability to inhibit selectively STAT6.

F. Inhibitors Block Development of Allergic Lung Disease (Induction Model)

The same model as described in part E was used to determine the effect of PH-242H on the induction of allergic lung disease. Mice that were immunized with ovalbumin and challenged intranasally with ovalbumin and *A. niger* spores developed AHR as determined by a shift to the left of the acetylcholine (Ach) dose response curve as compared to PBS challenged animals. Enzyme linked immunocell spot (ELISpot) assays were then performed on whole lung homogenates, assaying for IL-4, gamma interferon (IFN-γ) and IL-17A-secreting cells. Relative to sham immunized animals, both IL-17A-secreting cells and the ratio between IL-4 and IFN-γ-secreting cells were markedly enhanced in lungs of mice that were immunized with ovalbumin and received spores and ovalbumin intranasally. In contrast, these parameters were significantly suppressed by PH-242H, but not DLPC alone (FIG. 11C, FIG. 11D).

G. Inhibitors Block Development of Allergic Lung Disease (Reversal Model)

In separate experiments wild type C57BL/6 mice were challenged with the spores of *A. niger* for two weeks after which the inventors began to give PM-242H intranasally at 50 micrograms per dose at the time of continued fungal challenge for an additional two weeks (FIG. 13A). Addition of PM-242H during established disease resulted in the abrogation of airway hyperresponsiveness that otherwise persisted in sham-treated mice (FIG. 13B), and reduction in goblet cell metaplasia as assessed by periodic acid-Schiff staining of lung sections (FIG. 13G). PM-242H given during established disease did not, however, attenuate lung and airway inflammation (FIG. 13C-F), and in fact the number of airway eosinophils and lung IL-17A-secreting cells increased after PM-242H challenge (FIG. 13C, FIG. 13E). Thus, when given in a therapeutic context, PM-242H reverses the STAT6-dependent allergic airway disease features of airway hyperresponsiveness and goblet cell metaplasia, but does not diminish established allergic inflammation.

Figure 17A:
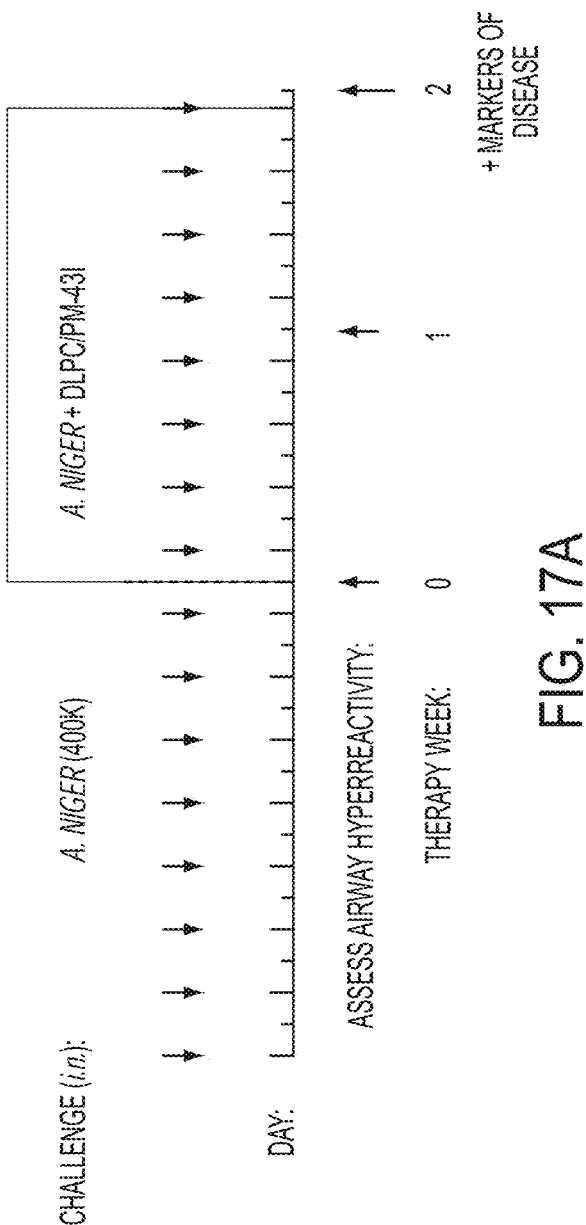
Figure 17C:
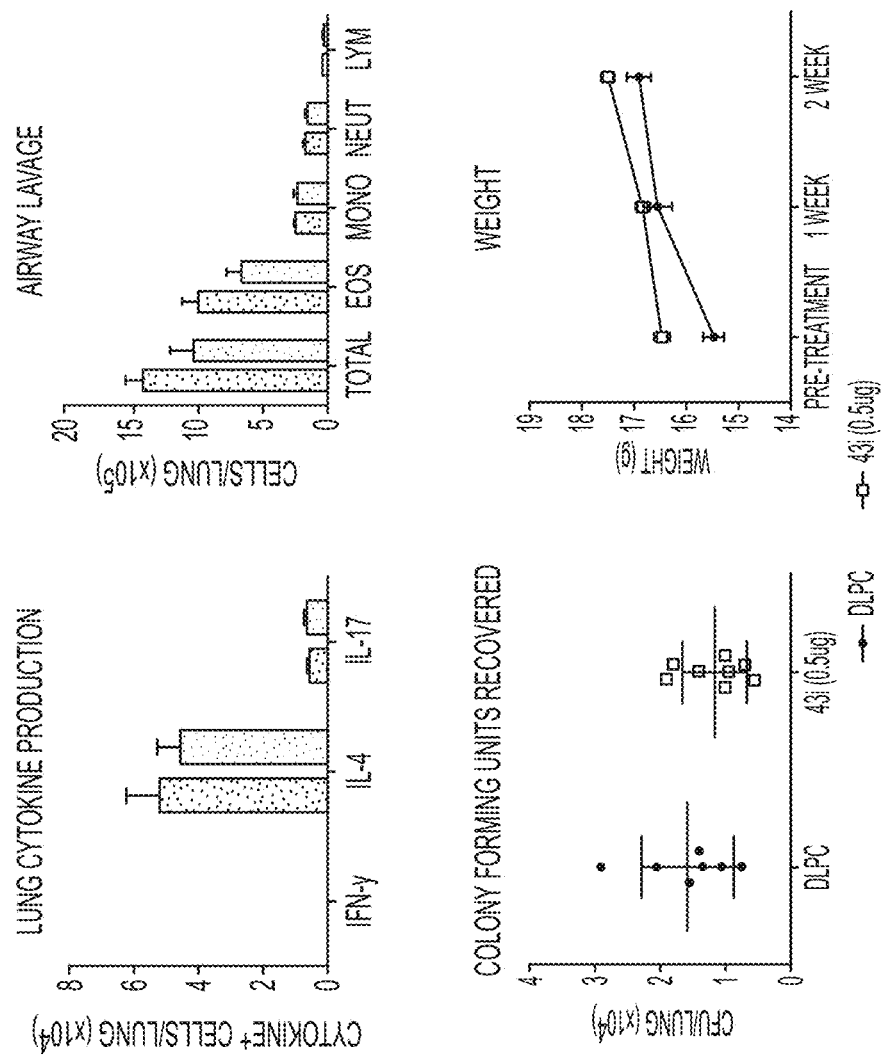

As shown in FIGS. 17A-C, PM-43I reverses established allergic airway disease. As shown in FIGS. 18A-C, activity of intranasally administered PM-43I and PM-86I is restricted to the lung.

H. Toxicity Studies

Figure 15A:
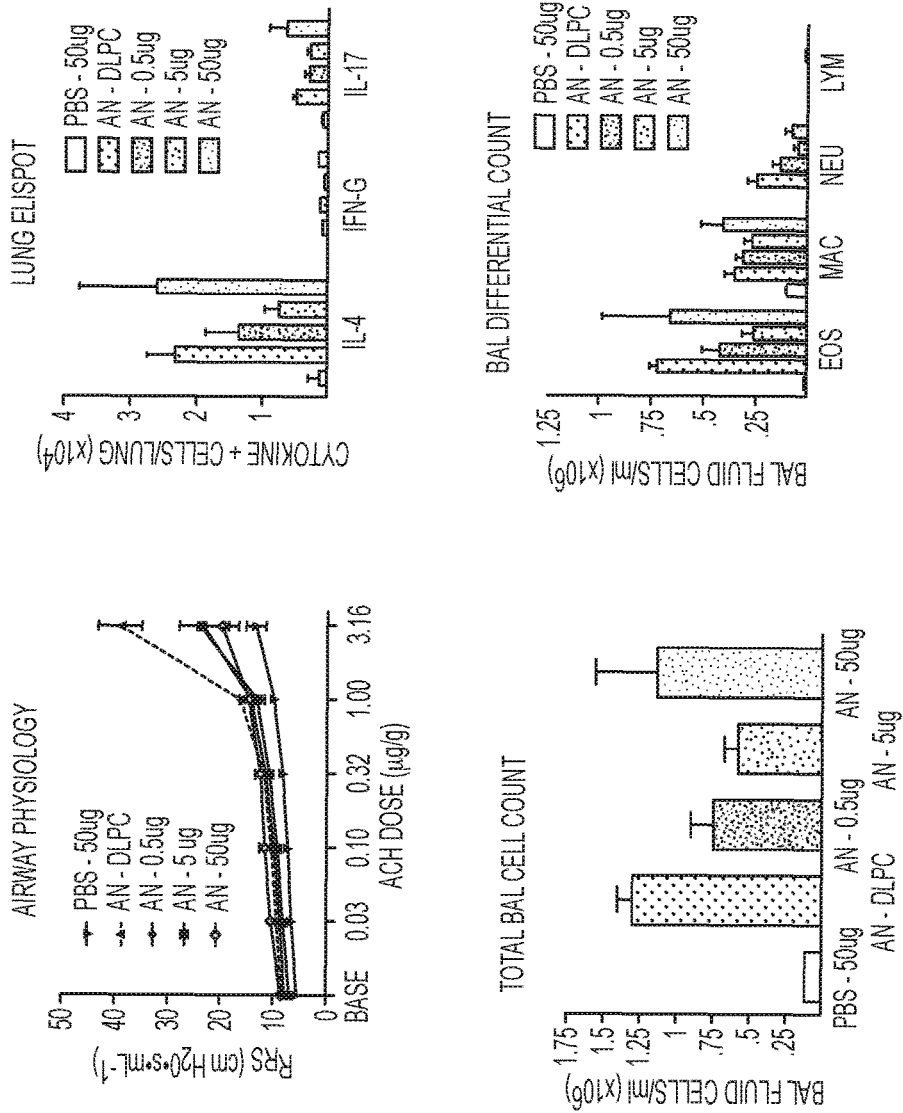
FIGS. 15A-B: Induction model for PM-86I (FIG. 15A) and PM-43I (FIG. 15B).
Figure 15B:
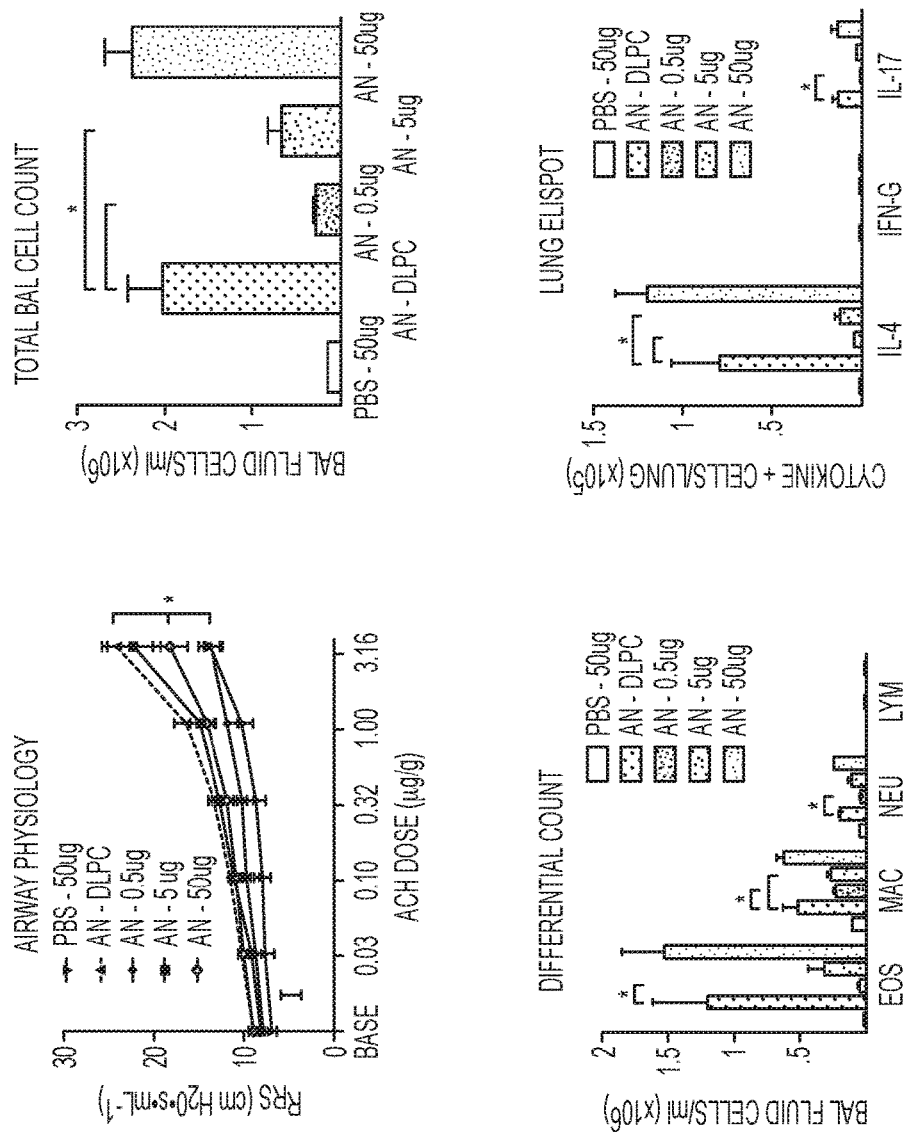
Figure 16B:
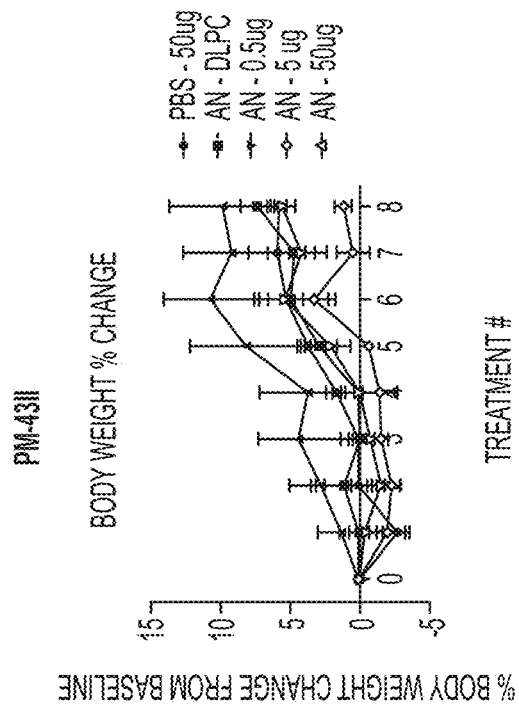
FIGS. 16A-B: Toxicity study of PM-86I (FIG. 16A) and PM-43II (FIG. 16B).
Figure 16A:
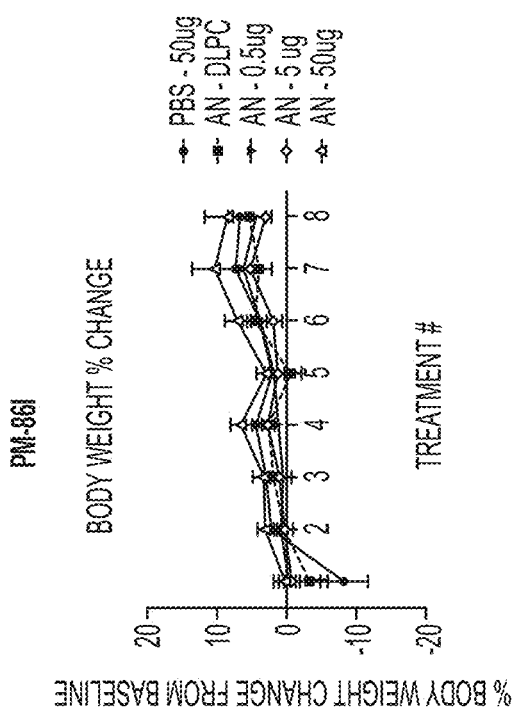

The issue of toxicity was addressed with the newer synthetic STAT6 peptidomimetic agents 86i and 43i in two ways. First, the inventors determined the effect of each inhibitor on asthma-related parameters in fungus-challenged mice. At an intermediate dose of 5 micrograms, PM 86i was maximally effective at inhibiting airway inflammation and lung IL-4 responses, but intermediately effective in inhibiting airway hyperresponsiveness (FIG. 15A). However, a 10-fold higher dose of 50 micrograms, although maximally effective in inhibiting airway hyperresponsiveness, resulted in a rebound of lung inflammation and IL-4 responses to sham-treated levels (FIG. 15A). Similar trends were seen with 43i (FIG. 15B), although the maximally effective dose was 10-fold lower than for 83i (0.5 micrograms). Second, the weights of mice were measured during challenge with the different doses of both STAT6 inhibitors. These data indicated no toxicity with 86i, i.e., there were no significant differences in terms of weight gain over the period of drug administration, but 43i did result in a reduction in weight gain at the highest dose of 50 micrograms.

I. Methods and Materials

Mice

For all mouse experiments, female mice between the ages of 4 and 8 weeks were used. All studies were conduced in compliance with all Federal and Institutional Animal Care and Use Committee regulations. β-arrestin 2 knockout ($\beta arr2^{-/-}$; 8 generations backcrossed to the C57BL/6 background) and $\beta_2$ Adrenergic Receptor knockout ($\beta_2 AR^{-/-}$; eight generations backcrossed to the FVB background) mice were generated as previously described (Walker, J. K. et al. 2003; Nguyen, L. P. et al. 2009). Balb/c, C57BL/6, and FVB wild type mice were purchased from Jackson Laboratories (Bar Harbor, Me.).

Drugs and Synthetic Reagents

Salmeterol (SX; S5068), albuterol (PHR1053), carvedilol (C3993), and nadolol (N1892) were purchased from Sigma-Aldrich (St. Louis, Mo.). 1,2-dilauroyl-sn-glycero-3-phosphocholine (DLPC; 770335) was purchased from Avanti Polar Lipids (Alabaster, Ala.) and used as a vehicle at a 1:5 (drug:DLPC) ratio. In brief, drug and DLPC were solubilized in t-butanol, frozen, lyophilized, and then placed in fine suspension by the addition of sterile, endotoxin-free phosphate buffered saline (PBS) and sonicated at 60 Hz for 30 seconds prior to use in vitro studies and administration to mice.

Infectious Allergic Lung Disease Model

Mice were challenged intranasally with a clinical isolate of $4 \times 10^5$ *A. niger* conidia every two days for a total of 8 challenges and treated with 50 μg of the indicated β-agonist, liposome vehicle (DLPC) and/or PM-242H (5 or 50 μg) intranasally as indicated and the allergic airway disease phenotype was determined according to previously described methods (Porter, P. et al. 2009).

Ovalbumin-Alum Allergic Lung Disease Model

Mice were sensitized to ovalbumin precipitated in alum as described in FIG. 3 (Corry, D. B. et al. 1996). In brief, mice were vaccinated intraperitoneally weekly with ovalbumin/alum together with PM-242H (50 or 250 μg) or liposome vehicle (DLPC) for 2 consecutive weeks and allowed to rest for 1 week. Mice were then intranasally challenged with ovalbumin (1 mg/mL in PBS; A5503, Sigma-Aldrich) and $4 \times 10^5$ *A. niger* conidia for 5 consecutive days after which the allergic airway disease phenotype was assessed. Randomization was not used to assign mice to specific treatment groups. Investigators were blind as to mouse genotype and treatment during data collection.

Allergic Airway Disease Analysis

Allergic airway disease was assessed as previously described (Porter, P. et al. 2009). Changes in respiratory system resistance ($R_{RS}$) in response to intravenous acetylcholine challenge, bronchoalveolar lavage (BAL) fluid differential counts, and analysis of lung IL-4, IL-17A and IFN-γ producing cells by enzyme linked immunocell spot assay (ELISpot) were performed as previously described (Lee, S. H. et al. 2003; Polikepahad, S. et al. 2010).

Ovalbumin Restimulation

Splenocytes from the indicated challenge groups of naïve and sensitized mice were assessed for antigen-specific recall cytokine responses by ELISpot. In brief, spleens were removed post mortem, de-aggregated by pressing through 40 μm nylon mesh and the red blood cells were removed from resulting cell suspension by hypotonic lysis. The splenocytes were then washed twice and cultured in flat-bottom wells of 96-well microtiter plates that were pre-coated with capture antibodies to IL-4, interferon gamma (IFN-γ) and IL-17A. Splenocytes were added in duplicate cultures of $0.5 \times 10^6$ cells/well that were then diluted serially two-fold to $0.015 \times 10^6$ cells/well. Cells were cultured in the presence of media or whole ovalbumin (1 mg/mL) overnight and plates were developed as previously described (Kheradmand, F. et al. 2002).

Histology

Lungs were perfused of blood by cannulating the pulmonary artery and injecting ice cold PBS until lavage returning via the left atrium was clear. Lungs were then inflated via the trachea with 10% formalin at 25 cm water pressure and the tracheas were tied off prior to removal of the cardiopulmonary unit en bloc submerging in 10% formalin overnight. Fixed lungs were then divided into individual lobes that were then halved and embedded in paraffin. Lung sections were cut at 5 microns and stained with the periodic acid-Schiff (PAS) kit (395B; Sigma-Aldrich, St. Louis, Mo.).

Cell Culture

Mycoplasma-free A549 (CCL-185) cells were acquired from American Type Culture Collection (Manassas, Va.). Cells were cultured in 50% DMEM, 50% F-12 complete media until confluent and switched to culture media containing 2% FBS for at least 24 h before stimulation. Long-term cultures were initiated on confluent cells by the addition of vehicle (DLPC) or select β-agonists and blockers (salbutamol, salmeterol and nadolol) at a working concentration of 10 μM. Cells were stimulated with 2 ng/mL IL-13 (213-IL/CF; R&D Systems, Minneapolis, Minn.) for identified times and harvested for protein and mRNA. Recombinant IL-6 (10 ng/mL) and IL-2 (5 ng/mL) were also added as indicated (both from R&D Systems).

Mycoplasma-free primary human epithelial cells of the sinonasal cavity were isolated from chronic rhinosinusitis patients and plated in complete BEGEM on type I collagen coated plates as previously described (Shaw, J. L. et al. 2013). Confluent cultures were in the presence of vehicle (DLPC), 10 μM salbutamol or 10 μM salmeterol for 4-5 days with media refreshed daily. On day 5, cells were stimulated for 24 hours with 2 ng/mL recombinant human IL-13.

Western Blot

Cells or lungs were isolated and lysed in RIPA buffer (9806S; Cell Signaling, Danvers, Mass.), protein was quantified using BCA Protein Assay Reagent (23227; Thermo Fisher Scientific, Rockford, Ill.) and denatured in Laemmli sample buffer (161-0737; Bio-Rad, Hercules, Calif.) according to manufacturer's protocol. Proteins were separated on SDS-Page gels were hand-poured using a standard electrophoresis unit (Bio-Rad, Hecules, Calif.) and transferred to a membrane using iBlot Gel Transfer Device (IB 1001; Invitrogen, Grand Island, N.Y.). Membranes were blocked in 2% FBS PBST and probed for c-Src, p-c-Src, pErk1/2, Erk1/2, p STAT6, STAT6, pSTAT3, STAT3, pSTAT5, STAT5, Shp-1, and β-actin. Signal was detected with a ChemiDoc XRS+ system (BioRad; Hercules, Calif.).

qPCR

RNA was purified from cell culture or select lobes of lung identified mice and RNA using the RNeasy Mini Kit (74104; Qiagen, Valencia, Calif.) or Trizol (15596-026; Invitrogen, Grand Island, N.Y.) and cDNA made with the TaqMan Reverse Transcription kit (N8080234; Applied Biosystems, Foster City, Calif.). Probes were acquired from Applied Biosystems (Foster City, Calif.) for 18 s, CC26 and Muc5AC and used to quantify relative expression with TaqMan Fast Universal PCR Master Mix (435189, Applied Biosystems, Foster City, Calif.) on a the 7500 Real-Time PCR System (Applied Biosystems, Foster City, Calif.).

Fungal Burden

Fungal burden of fungal challenged mice was assessed by serial dilution of lung homogenates (1/10 volume) on Sabouraud agar plates (84088; Sigma Aldrich, St. Louis, Mo.) in the presence of 100 mg/mL chloramphenicol (C0378; Sigma Aldrich, St. Louis, Mo.). Plates were incubated overnight at 37° C., assessed for total number of colonies and fungal colony forming units/lung was determined by dilution.

Statistical Analysis

Data are presented as means±standard error of means (SEM). For paired, normally distributed (log-transformed respiratory system resistance ($R_{RS}$)) data, Student's T test was used to determine significance (P<0.05). Otherwise, group comparisons of $R_{RS}$ data were made using ANOVA with Bonferroni's correction. All other data were compared using either the Mann-Whitney (2 groups) or Kruskal-Wallis (>2 groups) tests. Sample sizes for animal experiments were determined based on prior studies in which n=4 or 5 was found to be sufficient to achieve significance with regard to $R_{RS}$ values in moderately polarized treatment groups. Data variation was similar between compared experimental groups.

J. Synthesis

Synthesis of PM-28I

The synthesis of PM-28I was performed as follows:

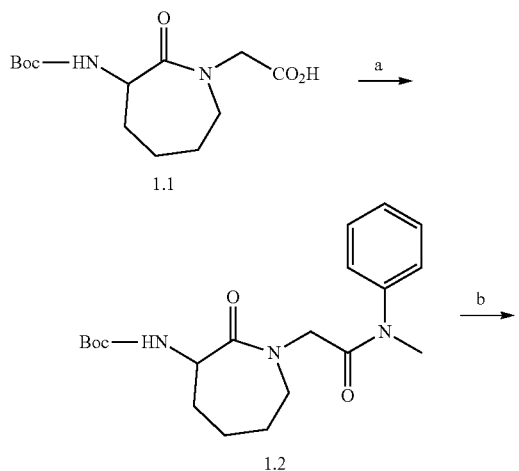

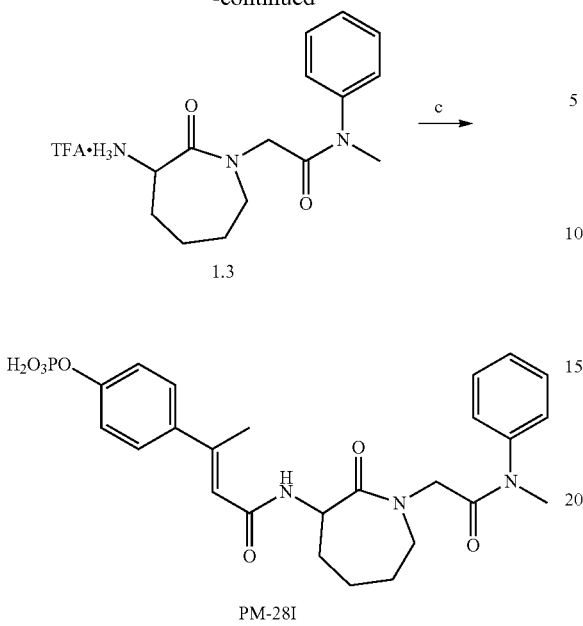

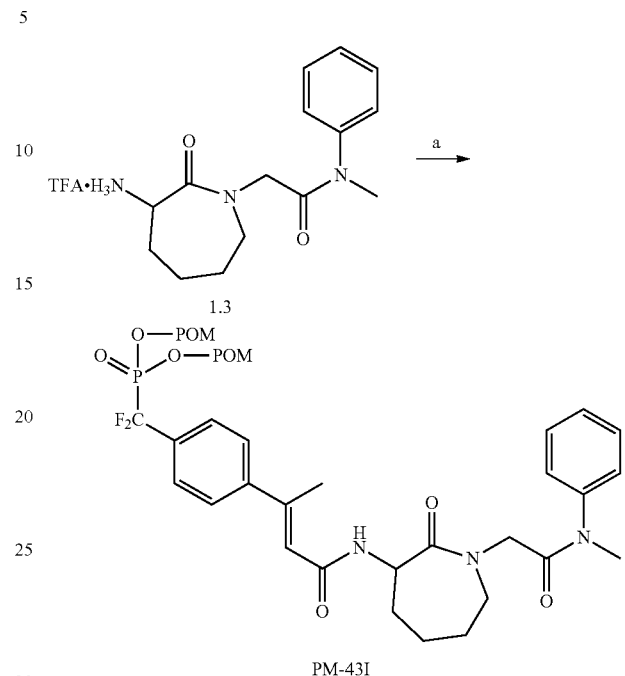

Synthesis of PM-43I

The synthesis of PM-43I was performed as follows:

Reagents and conditions: a) N-methylaniline, HBTU, DIPEA, DCM, overnight; b) TFA/DCM, 1 h; c) pentachlorophenyl (E)-3-(4-phosphorylphenyl) but-2-enoate (from Mandal et al. 2011), NMM, DMAP, NMP.

A solution of commercially available Boc-(3S)-3-amino-1-carboxymethylcaprolactam (1.1) (0.5 g, 1.75 mmol), N-methylaniline (0.2 g, 1.75 mmol), HBTU (0.8 g, 2.1 mmol) and DIPEA (0.7 mL, 3.5 mmol) in 25 mL of dry DCM was stirred for overnight. The mixture was diluted with additional 20 mL of DCM and washed with 5% HCl (2×20 mL) solution followed by 10% NaHCO$_3$ (1×20 mL) and brine (1×20 mL). After drying over MgSO$_4$ and concentrated to dryness 1.2 was then treated with 95% TFA-DCM for 1 h. The solvents were removed under vacuum till dryness and the residue was diluted with water and neutralized with aqueous NH$_4$OH and lyophilized to give 1.3, which was used without purification. Intermediate 1.3 (50.0 mg, 0.18 mmol) was dissolved in 2.0 mL of NMP and 0.1 mL of NMM and 2.0 mg of DMAP were added. To this was added pentachlorophenyl (E)-3-(4-phosphorylphenyl) but-2-enoate (from Mandal et al. 2011) (0.18 mmol, 90.0 mg). After 2.0 hr the mixture was applied to a reverse phase HPLC column and was chromatographed with a gradient of acetonitrile in H$_2$O (0.1% TFA in both solvents) to give 42.0 mg (46%) of PM-28I. HRMS (ESI-TOF) m/z: [M+H]+ Calcd for C$_{25}$H$_{31}$N$_3$O$_7$P 516.1900; Found 516.1879. $^1$H-NMR (600 MHz, DMSO-d$_6$) δ 1.47 (m, 1H), 1.62-1.73 (m, 3H), 1.77 (m, 1H), 1.86 (m, 1H), 2.46 (s, 3H), 2.51 (s, 2H), 3.18 (s, 3H), 3.27 (d, J=15.0 Hz, 1H), 3.62 (m, 1H), 3.9 (m, 2H), 4.64 (m, 1H), 6.42 (s, 1H), 7.18 (d, J=8.6 Hz, 2H), 7.4 (m, 3H), 7.48 (m, 2H), 7.53 (d, J=8.6 Hz, 2H), 8.00 (d, J=7.2 Hz, 1H). $^{13}$C-NMR (150 MHz, DMSO-d$_6$): δ 16.4, 26.4, 27.4, 31.2, 36.9, 49.7, 51.1, 51.3, 119.9, 120.0, 127.2, 129.7, 137.7, 147.2, 151.6, 151.7, 164.9, 167.6, 172.5.

Reagents and conditions: a) Pentachlorophenyl (2E)-3-[4-[[bis[(2,2-dimethyl-1-oxopropoxy)methoxy]phosphinyl]difluoromethyl]-phenyl]but-2-enoate, (from Mandal et al. 2011), NMM, DMAP, NMP.

Intermediate 1.3 (50.0 mg, 0.18 mmol) was dissolved in 2.0 mL of NMP and 0.1 mL of NMM and 2.0 mg of DMAP were added. To this was added pentachlorophenyl (2E)-3-[4-[[bis[(2,2-dimethyl-1-oxopropoxy)methoxy]phosphinyl]difluoromethyl]-phenyl]but-2-enoate (140 mg, 0.18 mmol) (from Mandal et al. 2011). After 2.0 hr the mixture was applied to a reverse phase HPLC column and was chromatographed with a gradient of acetonitrile in H$_2$O to give 38 mg (27%) of PM-43I. HRMS (ESI-TOF) m/z: [M+H]+ Calcd for C$_{38}$H$_{51}$F$_2$N$_3$O$_{10}$P 778.3280; Found 778.3268. $^1$H-NMR (600 MHz, CDCl$_3$) δ 1.22 (s, 18), 1.56 (m, 1H), 1.61-1.8 (m, 3H), 1.9 (m, 1H), 2.0 (m, 1H), 2.12 (d, J=13.2 Hz, 1H), 2.53 (s, 3H), 3.18 (m, 1H), 3.28 (s, 3H), 3.72 (m, 1H), 3.93 (m, 2H), 4.72 (m, 1H), 5.65 (dd, J=5.0 Hz, 2H), 5.74 (dd, J=5.0 Hz, 2H), 6.1 (s, 1H), 7.05 (d, J=6.0 Hz, 1H), 7.3 (d, J=7.7 Hz, 2H), 7.4 (m, 1H), 7.45 (m, 2H), 7.5 (d, J=8. Hz, 2H), 7.6 (d, J=8.0 Hz, 2H). $^{13}$C-NMR (150 MHz, CDCl$_3$) δ 17.5, 26.8, 26.9, 27.9, 31.8, 37.6, 38.7, 51.2, 52.1, 52.4, 82.4, 82.5, 121.4, 126.4, 126.5, 127.3, 128.4, 130.1, 142.7, 145.6, 149.4, 165.3, 167.7, 173.5, 176.5.

Synthesis of PM-242H

Synthesis of the STAT6 antagonist PM-242H was based on previously published methods (Mandal, et al., 2009, U.S. Pat. No. 6,426,331) with the strategy summarized in the scheme below.

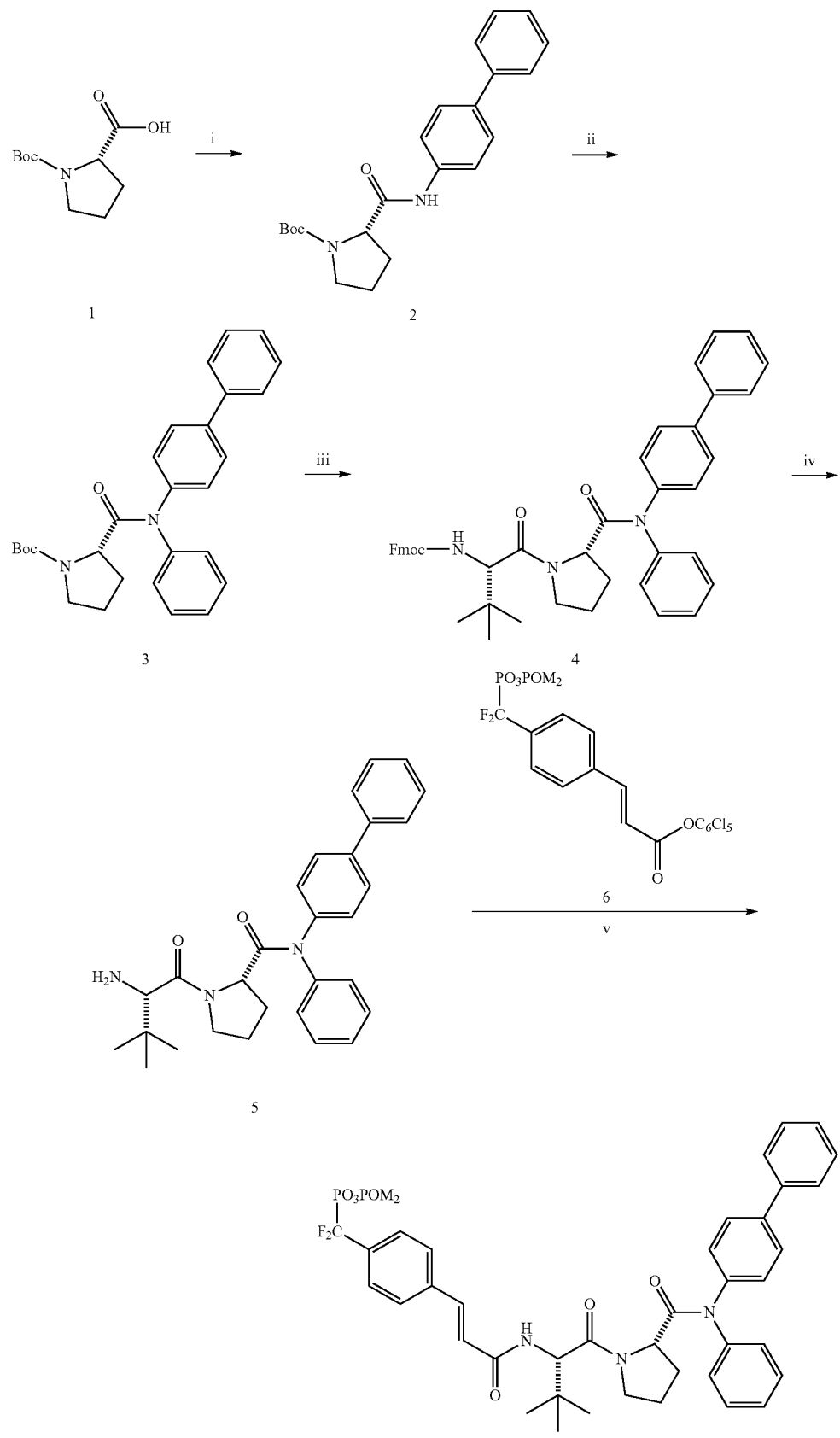

Reagents and conditions: i) 4-aminobiphenyl, EDC, CH₂Cl₂, rt, 12 h, 91%; ii) Ph₃Bi, Cu(OAc)₂, TEA, CH₂Cl₂, rt, 48 h, 77%; iii) a) TFA, b) Fmoc-Tle-OH, HBTU, DIPEA, rt, 12 h, 82%; iv) 20% piperidine/DMF 30 min. 61%; v) 6, NMP, NMM, DMAP(cat.), 2 h, 71%.

Synthesis of Boc-prolyl-4-amidobiphenyl, 2

A solution of Boc-Proline (1, 2.0 g, 9.3 mmol), 4-aminobiphenyl (1.6 g, 9.3 mmol) and EDC (2.1 g, 11.2 mmol) in 60 mL of dry CH₂Cl₂ was stirred overnight. It was then transferred to a separatory funnel with an additional 20 mL of CH₂Cl₂ and washed with 5% HCl (2×30 mL) followed by 10% NaHCO₃ (2×30 mL) and brine (1×20 mL). The organic layer was dried (MgSO₄) and concentrated under reduced pressure. Purification by silica gel column chromatography eluting with 15% EtOAc-hexane afforded the title products as a white solid (3.1 g, 91% yield). Calcd (M+H): 367.2022; Found (M+H): 367.2351. $^1$H NMR (CDCl₃, 600 MHz) δ:9.6 (s, 1H), 7.51-7.63 (m, 6H), 7.44 (m, 2H), 7.34 (m, 1H), 4.54 (m, 1H), 3.32-3.68 (m, 2H), 1.84-2.07 (m, 4H), 1.54 (s, 9H). $^{13}$C NMR (CDCl₃, 150 MHz) δ: 128.9, 127.5, 127.0, 126.8, 119.9, 80.9, 47.3, 28.4.

Synthesis of N-phenyl Boc-prolyl-4-amidobiphenyl, 3

To a stirred solution of 2 (2.0 g, 5.4 mmol) in dry CH₂Cl₂ (50 mL) was added triphenylbismuth (3.6 g, 8.2 mmol), Cu(OAc)₂ (1.6 g, 8.2 mmol) and dry triethylamine (1.2 mL, 8.2 mmol). The reaction was monitored by HPLC. After completion of the reaction, the solvent was evaporated in vacuo and the residue was diluted with ether (150 mL) and filtered through celite. The organic layer was washed with 5% HCl (2×30 mL) followed by brine and was dried over MgSO₄. Concentration under reduced pressure followed by purification by silica gel chromatography using 10% EtOAc-hexane afforded 3 as a white solid (1.9 g, 77% yield). Calcd (M+H): 443.2335; Found (M+H): 443.2349 $^1$H NMR (CDCl₃, 600 MHz) δ: 7.2-7.63 (m, 14H), 4.38 (m, 1H), 4.25 (m, 1H isomer), 3.48-3.6 (m, 2H), 3.4 (m, 1H), 3.32 (m, 1H isomer), 1.8-2.1 (m, 2H), 1.65-1.75 (m, 2H), 1.46 (s, 9H), 1.4 (s, 9H isomer). $^{13}$C NMR (CDCl₃, 150 MHz) δ: 173.2, 172.8, 154.4, 153.8, 129.9, 129.3, 128.8, 128.4, 127.5, 127.1, 126.4, 125.9, 79.9, 79.3, 58.00, 57.8, 47.2, 31.9, 30.4, 28.8, 28.6, 28.4, 24.3, 23.4.

Synthesis of Fmoc-tert-butylglycyl-N-phenyl-prolyl-4-amidobiphenyl, 4

A solution of 3 (1.00 g, 2.25 mmol) in 5 mL of neat trifluoroacetic acid (TFA) was stirred for 1 h. Excess TFA was removed under vacuum. The residue was then treated with Fmoc-Tle-OH (0.8 g, 2.25 mmol), HBTU (0.85 g, 2.25 mmol), DIPEA (1.2 mL, 6.7 mmol) in 50 mL of dry CH₂Cl₂ overnight. The organic layer was diluted with an additional 50 mL of CH₂Cl₂ and washed with 5% HCl (3×30 mL) followed by 10% NaHCO₃ (1×30 mL) and brine. After drying (MgSO₄) and concentration under vacuum, the crude product was purified by silica gel chromatography using 35% EtOAc-hexane to give the desired material as white foam. Yield: 1.25 g 82%. Calcd (M+H): 678.3332; Found (M+H): 678.3438. $^1$H NMR (CDCl₃, 600 MHz) δ: 7.78 (m, 2H), 7.63-7.71 (m, 3H), 7.24-7.62 (m, 17H), 6.5 (d, J=10.5 Hz, 1H), 4.67 (m, 1H), 4.6 (m, 1H, isomer), 4.5 (d, J=10.5 Hz, 1H), 4.42 (m, 1H), 4.3 (m, 1H), 4.23 (m, 1H), 4.0 (m, 1H), 3.84 (m, 1H), 2.1-2.24 (m, 3H), 1.94 (m, 1H), 1.17 (s, 9H). $^{13}$C NMR (CDCl₃, 150 MHz) δ:172.5, 171.3, 159.1, 158.8, 156.9, 143.8, 142.1, 141.7, 141.3, 140.8, 140.4, 139.8, 130.1, 129.3, 128.9, 128.7, 127.9, 127.8, 127.7, 127.4, 127.1, 127.0, 126.6, 126.5, 125.4, 125.3, 120.0, 119.9, 115.8, 113.9, 67.5, 59.5, 59.3, 49.3, 47.1, 35.9, 29.7, 26.4, 25.7, 25.3.

Synthesis of tert-butylglycyl-N-phenyl-prolyl-4-amidobiphenyl, 5

Compound 4, (0.5 g, 0.74 mmol) was treated with 4.0 mL of 20% piperidine in DMF for 30 min. The reaction mixture was concentrated under vacuum. The residue was purified by to RP-HPLC (2.5×25 cm Phenomonex Luna C18 column eluting with a linear gradient of MeCN in H₂O) and the pure fractions then collected and lyophilized to get 0.210 g (61% yield) of desired material (5) as a white powder. Calcd (M+H): 456.2651; Found (M+H): 456.2708.

Synthesis of PM-242H

To a stirred solution of 5 (0.05 g, 0.1 mmol) and the active ester (6) (0.075 g, 0.1 mmol) in 3 mL of dry NMP, 40 µL of N-methylmorpholine and 4-DMAP (0.002 g, 0.02 mmol) was added. The reaction was then monitored by HPLC. After completion, the desire product then purified from the crude by RP-HPLC (2.5×25 cm Phenomonex Luna C18 column eluting with a linear gradient of MeCN in H₂O). Combined pure fractions then lyophilized to get of pure PM-242H as a white powder (73 mg, 71%). Calcd (M+H): 944.4063; Found (M+H): 944.4217. $^1$H NMR (CDCl₃, 600 MHz) δ: 7.5-7.56 (m, 4H), 7.4-7.5 (m, 7H), 7.3-7.38 (m, 3H), 7.2-7.3 (m, 5H), 6.82 (d, J=10.5 Hz, 1H), 6.44 (d, J=16.0 Hz, 1H), 5.66 (m, 2H), 5.57 (m, 2H), 4.8 (d, J=10.5 Hz, 1H), 3.9 (m, 1H), 3.75 (m, 1H), 1.93-2.12 (m, 3H), 1.8 (m, 1H), 1.14 (s, 18H), 1.07 (s, 9H). $^{13}$C NMR (CDCl₃, 150 MHz) δ:176.6, 172.0, 170.3, 165.4, 140.1, 137.6, 130.0, 129.1, 128.9, 128.8, 128.5, 127.8, 127.7, 127.1, 126.9, 126.5, 122.5, 82.5, 82.4, 59.0, 57.4, 49.1, 38.7, 36.3, 29.8, 26.7, 26.6.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,764,377
U.S. Pat. No. 5,324,756
U.S. Pat. No. 6,426,331
WO2001/083517
WO2009145856A1
WO 2001083517A1

Blease, K. Therapeutics targeting IL-13 for the treatment of pulmonary inflammation and airway remodeling. Curr. Opin. Investig. Drugs 2008, 9, 1180-1184.

Chiba, Y.; Todoroki, M.; Nishida, Y.; Tanabe, M.; Misawa, M. A novel STAT6 inhibitor AS1517499 ameliorates antigen-induced bronchial hypercontractility in mice. Am. J. Respir. Cell Mol. Biol. 2009, 41, 516-524.

Corry, D. B. et al. Interleukin 4, but not interleukin 5 or eosinophils, is required in a murine model of acute airway hyperreactivity. J. Exp. Med. 183, 109-117 (1996).

Darcan-Nicolaisen, Y.; Meinicke, H.; Fels, G.; Hegend, O.; Haberland, A.; Kuhl, A.; Loddenkemper, C.; Witzenrath, M.; Kube, S.; Henke, W.; Hamelmann, E. Small interfering RNA against transcription factor STAT6 inhibits allergic airway inflammation and hyperreactivity in mice. J. Immunol. 2009, 182, 7501-7508.

Kasaian, M. T.; Miller, D. K. IL-13 as a therapeutic target for respiratory disease. Biochem. Pharmacol. 2008, 76, 147-155.

Kheradmand, F. et al. A protease-activated pathway underlying Th cell type 2 activation and allergic lung disease. J. Immunol. 169, 5904-5911 (2002).

Kuperman, D. A.; Schleimer, R. P. Interleukin-4, interleukin-13, signal transducer and activator of transcription factor 6, and allergic asthma. Curr. Mol. Med. 2008, 8, 384-392.

Lee, S. H. et al. Differential requirement for CD 18 in T-helper effector homing. Nat. Med. 9, 1281-1286 (2003).

Mandal, P. K.; Liao, W. S.; McMurray, J. S. Synthesis of phosphatase-stable, cell-permeable peptidomimetic prodrugs that target the SH2 domain of Stat3. Org. Lett. 2009, 11, 3394-3397.

Mandal, P. K.; Gao, F.; Lu, Z.; Ren, Z.; Ramesh, R.; Birtwistle, J. S.; Kaluarachchi, K. K.; Chen, X.; Bast, R. C.; Liao, W. S.; McMurray, J. S. Potent and Selective Phosphopeptide Mimetic Prodrugs Targeted to the Src Homology 2 (SH2) Domain of Signal Transducer and Activator of Transcription 3. J. Med. Chem. 2011, 54, 3549-5463.

McCusker, C. T.; Wang, Y.; Shan, J.; Kinyanjui, M. W.; Villeneuve, A.; Michael, H.; Fixman, E. D. Inhibition of Experimental Allergic Airways Disease by Local Application of a Cell-Penetrating Dominant-Negative STAT-6 Peptide. J. Immunol. 2007, 179, 2556-2564.

Mullings, R. E.; Wilson, S. J.; Puddicombe, S. M.; Lordan, J. L.; Bucchieri, F.; Djukanovic, R.; Howarth, P. H.; Harper, S.; Holgate, S. T.; Davies, D. E. Signal transducer and activator of transcription 6 (STAT-6) expression and function in asthmatic bronchial epithelium. J. Allergy Clin. Immunol. 2001, 108, 832-838.

Nagashima, S.; Yokota, M.; Nakai, E.; Kuromitsu, S.; Ohga, K.; Takeuchi, M.; Tsukamoto, S.; Ohta, M. Synthesis and evaluation of 2-{[2-(4-hydroxyphenyl)-ethyl] amino}pyrimidine-5-carboxamide derivatives as novel STAT6 inhibitors. Bioorg. Med. Chem. 2007, 15, 1044-1055.

Nagashima, S.; Nagata, H.; Iwata, M.; Yokota, M.; Moritomo, H.; Orita, M.; Kuromitsu, S.; Koakutsu, A.; Ohga, K.; Takeuchi, M.; Ohta, M.; Tsukamoto, S. Identification of 4-benzylamino-2-[(4-morpholin-4-ylphenyl)amino] pyrimidine-5-carboxamide derivatives as potent and orally bioavailable STAT6 inhibitors. Bioorg. Med. Chem. 2008, 16, 6509-6521.

Nagashima, S.; Hondo, T.; Nagata, H.; Ogiyama, T.; Maeda, J.; Hoshii, H.; Kontani, T.; Kuromitsu, S.; Ohga, K.; Orita, M.; Ohno, K.; Moritomo, A.; Shiozuka, K.; Furutani, M.; Takeuchi, M.; Ohta, M.; Tsukamoto, S. Novel 7H-pyrrolo [2,3-d]pyrimidine derivatives as potent and orally active STAT6 inhibitors. Bioorg. Med. Chem. 2009, 17, 6926-6936.

Nguyen, L. P. et al. Beta2-adrenoceptor signaling is required for the development of an asthma phenotype in a murine model. Proc Natl Acad Sci USA 106, 2435-2440 (2009).

Oh, C. K.; Geba, G. P.; Molfino, N. Investigational therapeutics targeting the IL-4/IL-13/STAT-6 pathway for the treatment of asthma. Eur. Respir. Rev. 2010, 19, 46-54.

Ohga, K.; Kuromitsu, S.; Takezawa, R.; Numazaki, M.; Ishikawa, J.; Nagashima, S.; Shimizu, Y. YM-341619 suppresses the differentiation of spleen T cells into Th2 cells in vitro, eosinophilia, and airway hyperresponsiveness in rat allergic models. Eur. J. Pharmacol. 2008, 590, 409-416.

Polikepahad, S. et al. A reversible, non-invasive method for airway resistance measurements and bronchoalveolar lavage fluid sampling in mice. J. Vis. Exp. 38 (2010).

Popescu, F. D. New asthma drugs acting on gene expression. J. Cell. Mol. Med. 2003, 7, 475-486.

Porter, P. et al. Link between allergic asthma and airway mucosal infection suggested by proteinase-secreting household fungi. Mucosal Immunol. 2, 504-517 (2009).

Shaw, J. L. et al. IL-33-Responsive Innate Lymphoid Cells Are an Important Source of IL-13 in Chronic Rhinosinusitis with Nasal Polyps. Am. J. Respir. & Crit. Care Med. 188, 432-439 (2013).

Stolzenberger, S.; Haake, M.; Duschl, A. Specific inhibition of interleukin-4-dependent Stat6 activation by an intracellularly delivered peptide. Eur. J. Biochem. 2001, 268, 4809-4814.

Walker, J. K. et al. Beta-arrestin-2 regulates the development of allergic asthma. J Clin Invest 112, 566-574 (2003).

Walsh, G. M. An update on emerging drugs for asthma. Expert Opin. Emerg. Drugs 2012, 17, 37-42.

Wang, L. H.; Yang, X. Y.; Kirken, R. A.; Resau, J. H.; Farrar, W. L. Targeted disruption of stat6 DNA binding activity by an oligonucleotide decoy blocks IL-4-driven T(H)2 cell response. Blood 2000, 95, 1249-1257.

Wang, Y.; Li, Y.; Shan, J.; Fixman, E.; McCusker, C. Effective treatment of experimental ragweed-induced asthma with STAT-6-IP, a topically delivered cell-penetrating peptide. Clin. Exp. Allergy 2011, 41, 1622-1630.

Wu, P.; Brasseur, M.; Schindler, U. A high-throughput STAT binding assay using fluorescence polarization. Anal. Biochem. 1997, 249, 29-36.

Zhou, L.; Kawate, T.; Liu, X.; Kim, Y. B.; Zhao, Y.; Feng, G.; Banerji, J.; Nash, H.; Whitehurst, C.; Jindal, S.; Siddiqui, A.; Seed, B.; Wolfe, J. L. STAT6 phosphorylation inhibitors block eotaxin-3 secretion in bronchial epithelial cells. Bioorg. Med. Chem. 2012, 20, 750-758.

Novabiochem, *Guide to the Selection of Building Blocks for Peptide Synthesis* (2008)

*Handbook of Pharmaceutical Salts: Properties, and Use* (P. H. Stahl & C. G. Wermuth eds., Verlag Helvetica Chimica Acta, 2002)

*March's Advanced Organic Chemistry: Reactions, Mechanisms, and Structure* (2007)

*Remington's Pharmaceutical Sciences*, 18th Ed. Mack Printing Company, pp 1289-1329, 1990.

*Remington: The Science and Practice of Pharmacy*, 21st Ed. Lippincott Williams and Wilkins, 2005.

The invention claimed is:

1. A compound of the formula:

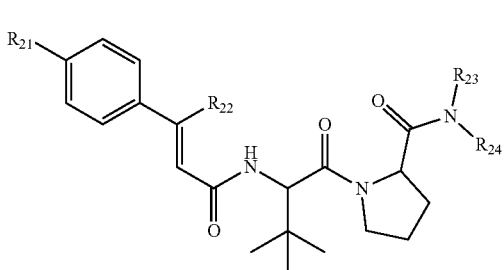
(I)

wherein:
  $R_{21}$ is phosphate, —OP(O)(OR$_{10}$)(OR$_{10'}$), -alkyl$_{(C1-6)}$-P(O)(OR$_{10}$)(OR$_{10'}$), or a substituted version of any of these groups; wherein
    $R_{10}$ and $R_{10'}$ are each independently hydrogen, alkyl$_{(C1-6)}$, aryl$_{(C6-8)}$, aralkyl$_{(C7-12)}$, alkyl$_{(C1-6)}$-O—C(O)-alkyl$_{(C1-6)}$, alkyl$_{(C1-6)}$-O—C(O)-aryl$_{(C6-8)}$, or

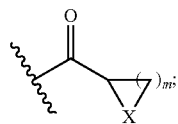

wherein m=1-8; wherein X is —CH$_2$—, —O—, —S—, or —NH—; provided that $R_{10}$ and $R_{10'}$ are not both hydrogen;
  $R_{22}$ is hydrogen or alkyl$_{(C1-6)}$;
  $R_{23}$ is hydrogen, alkyl$_{(C1-12)}$, or aryl$_{(C6-12)}$;
  $R_{24}$ is aryl$_{(C\le12)}$;
  wherein if an alkyl, aryl, or aralkyl group is substituted then one or more hydrogen atom on the alkyl, aryl or aralkyl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$;
or a pharmaceutically acceptable salt thereof.

2. The compound of claim 1, wherein the $R_{21}$ is -alkyl$_{(C1-6)}$-P(O)(OR$_{10}$)(OR$_{10'}$) or substituted -alkyl$_{(C1-6)}$-P(O)(OR$_{10}$)(OR)(OR$_{10'}$).

3. The compound of claim 2, wherein $R_{21}$ is —CF$_2$—P(O)(OCH$_2$OC(O)C(CH$_3$)$_3$)$_2$.

4. The compound of claim 1, wherein $R_{22}$ is hydrogen.

5. The compound of claim 1, wherein $R_{23}$ is aryl$_{(C6-12)}$.

6. The compound of claim 5, wherein $R_{23}$ is phenyl.

7. The compound of claim 1, wherein $R_{24}$ is aryl$_{(C8-C12)}$.

8. The compound of claim 7, wherein $R_{24}$ is biphenyl.

9. The compound of claim 1, wherein the compound has the formula:

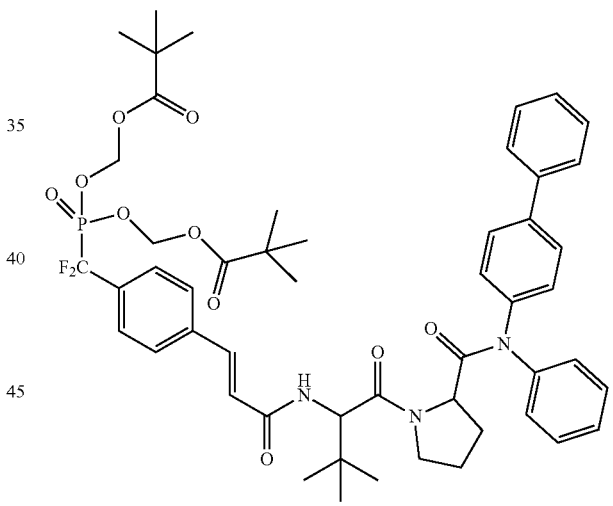

or a pharmaceutically acceptable salt thereof.

10. A pharmaceutical composition comprising an effective amount of a compound of formula (I) of claim 1, or a pharmaceutically acceptable salt thereof, and a pharmaceutically acceptable excipient.

11. The pharmaceutical composition of claim 10, wherein the pharmaceutical composition is formulated for oral, intravenous, intranasal, or inhalational administration.

12. The pharmaceutical composition of claim 11, wherein the pharmaceutical composition is comprised in a nebulizer, an inhaler, or a nasal spray.

13. The pharmaceutical composition of claim 12, wherein the pharmaceutical composition further comprises a bronchodialator.

14. The pharmaceutical composition of claim 13, wherein the bronchodialator is a long-acting β2 agonist.

15. A method of treating an allergic or inflammatory lung disease in a subject comprising administering to the subject a therapeutically effective amount of a compound of claim 1 to the subject.

16. The method of claim 15, wherein the lung disease is asthma or airway hyperresponsiveness.

17. The method of claim 15, wherein the lung disease is an allergic disease, allergic rhinitis, emphysema, chronic obstructive pulmonary disease (COPD), reactive airway disease, or chronic rhinosinusitis.

18. The method of claim 15, further comprising administering to the subject a second therapeutic compound to the subject.

19. The method of claim 18, wherein the second therapeutic compound is a bronchodialator, an anti-inflammatory steroid, an antihistamine, or an anti-fungal antibiotic.

20. The method of claim 19, wherein the second therapeutic compound is a bronchodialator, and wherein the bronchodialator is a short-acting β-2 agonist, a long-acting β2 agonist, or an anticholinergic.

21. A method of inhibiting STAT6 in a subject comprising administering to the subject a compound of claim 1 to the subject in an amount an effective to inhibit STAT6, wherein the subject has lung inflammation.

22. The compound of claim 1, wherein $R_{23}$ is hydrogen or $alkyl_{(C1-12)}$.

* * * * *